US012133890B2

(12) United States Patent
Shang et al.

(10) Patent No.: US 12,133,890 B2
(45) Date of Patent: Nov. 5, 2024

(54) ANTIGEN-BINDING POLYPEPTIDE TARGETING B7H3 AND APPLICATION THEREOF

(71) Applicant: NINGBO T-MAXIMUM BIOPHARMACEUTICALS CO., LTD., Ningbo (CN)

(72) Inventors: Xiaoyun Shang, Ningbo (CN); Haijuan Jiang, Ningbo (CN); Dan Wang, Ningbo (CN); Jialu Li, Ningbo (CN); Shaowen Ma, Ningbo (CN); Hui Shen, Ningbo (CN); Li Ma, Ningbo (CN); Weijie Chen, Ningbo (CN)

(73) Assignee: NINGBO T-MAXIMUM BIOPHARMACEUTICALS CO., LTD., Ningbo (CN)

( * ) Notice: Subject to any disclaimer, the term of this patent is extended or adjusted under 35 U.S.C. 154(b) by 0 days.

(21) Appl. No.: 18/575,650

(22) PCT Filed: Jun. 30, 2022

(86) PCT No.: PCT/CN2022/103070
§ 371 (c)(1),
(2) Date: Dec. 29, 2023

(87) PCT Pub. No.: WO2023/274384
PCT Pub. Date: Jan. 5, 2023

(65) Prior Publication Data
US 2024/0269283 A1    Aug. 15, 2024

(30) Foreign Application Priority Data

Jul. 1, 2021 (CN) .......................... 202110749481.6

(51) Int. Cl.
*A61K 39/00* (2006.01)
*C07K 14/705* (2006.01)
*C07K 14/725* (2006.01)
*C07K 16/28* (2006.01)
*C12N 5/0783* (2010.01)

(52) U.S. Cl.
CPC ...... *A61K 39/4643* (2023.05); *A61K 39/4611* (2023.05); *A61K 39/4631* (2023.05); *A61K 39/464411* (2023.05); *A61K 39/464412* (2023.05); *C07K 14/7051* (2013.01); *C07K 14/70517* (2013.01); *C07K 14/70578* (2013.01); *C07K 16/2827* (2013.01); *C12N 5/0636* (2013.01); *A61K 2239/26* (2023.05); *A61K 2239/31* (2023.05); *A61K 2239/38* (2023.05); *C07K 2317/53* (2013.01); *C07K 2319/02* (2013.01); *C07K 2319/03* (2013.01); *C12N 2510/00* (2013.01)

(58) Field of Classification Search
None
See application file for complete search history.

(56) References Cited

U.S. PATENT DOCUMENTS

2023/0124851 A1* 4/2023 Eckelman .......... C07K 16/2809
424/136.1

FOREIGN PATENT DOCUMENTS

| CN | 113061580 A | 7/2021 |
|---|---|---|
| WO | WO 02/48193 A2 | 6/2002 |
| WO | WO 2009/068631 A1 | 6/2009 |
| WO | WO 2020/076970 A1 | 4/2020 |
| WO | WO 2021/081052 A1 | 4/2021 |

OTHER PUBLICATIONS

International Search Report & Written Opinion issued Sep. 28, 2022 in PCT/CN2022/103070, filed on Jun. 30, 2022, 21 pages (with English Translation).
Chinese Office Action issued May 25, 2023 in CN 202280004519. X, 7 pages.
Lee et al. "Advanced genetic engineering to achieve in vivo targeting of adenovirus utilizing camelid single domain antibody", Journal of Controlled Release 334 (2021) pp. 106-113.
Tang et al. "Administration of B7-H3 targeted chimeric antigen receptor-Tcells induce regression of glioblastoma", Signal Transduction and Targeted Therapy, vol. 6 No. 1, 2021, 3 pages.
Zhang et al. "Progress in B7-H3 targeted CAR-T cells for immunotherapy of solid tumors", Chinese Journal of Immunology, 2021, 6 pages (With English Abstract).

* cited by examiner

*Primary Examiner* — Jessica H Roark
(74) *Attorney, Agent, or Firm* — Merchant & Gould, P.C.; Daniel J. Pereira

(57) ABSTRACT

The present application relates to an antigen-binding polypeptide that specifically binds to B7H3, comprising at least one complementarity-determining region (CDR) of an antibody heavy chain variable region (VH), wherein the VH comprises an amino acid sequence set forth in SEQ ID NO: 25. The present application further relates to a chimeric antigen receptor comprising the antigen-binding polypeptide and a universal CAR-T cell comprising the chimeric antigen receptor. The CAR-T cell recognizes a surface antigen of a tumor cell and knocks out TCR and HLA-A genes expressed by the cell at the same time, so that the immune rejection caused by an allogeneic CAR-T therapy is reduced, the survival time of the cell is prolonged, and the anti-tumor effect is improved.

26 Claims, 24 Drawing Sheets
Specification includes a Sequence Listing.

Off-target display after removal of control background

Off-target display after removal of control background

T1: TRAC upper strand:HLA-A02 upper strand linked together
T2: TRAC upper strand:HLA-A02 lower strand linked together
$10^{-4}$: not detected

- A: CD3⁺T
- B: TRAC and HLA-A double-knockout CAR-T cells
- C: TRAC, HLA-A, and CIITA triple-gene knockout CAR-T cells
- D: TRAC, B2M, and CIITA triple-gene knockout CAR-T cells

ANTIGEN-BINDING POLYPEPTIDE TARGETING B7H3 AND APPLICATION THEREOF

CROSS REFERENCE TO RELATED APPLICATIONS

This application is a National Stage entry under 35 U.S.C. § 371 of PCT/CN2022/103070, filed on Jun. 30, 2022, and claims priority to CN patent application Ser. No. 20/211, 0749481.6, filed on Jul. 1, 2021, the entire contents of which are incorporated herein by reference.

SEQUENCE STATEMENT

This application contains a Sequence Listing, which has been submitted electronically in .TXT format and is hereby incorporated by reference in its entirety. Said .TXT copy, created and filed herewith, is named 20240718_0131-PA-025US_sequence listing.txt and is 135000 bytes in size.

TECHNICAL FIELD

The present application relates to the field of biomedicine, and in particular to an antigen-binding polypeptide targeting B7H3 and use thereof.

BACKGROUND

Glioblastomas account for 15% of all brain tumors, and may originate from common brain cells or develop from low-grade astrocytomas. Generally, the survival time after diagnosis is 12 to 15 months, and only 3% to 7% of patients survive more than five years. Without treatment, the survival time is generally 3 months. About 3 out of every 100 thousand people are newly diagnosed with glioblastoma every year, which is the most common cancer of brain origin and the second most common brain tumor after meningioma.

With the development of tumor immunity theory and the progress of technology, the cell immunotherapy for tumors attracts more and more attention. CAR-T cell technology is a cell-based therapeutic approach that has produced excellent results in tumor immunotherapy, especially in the treatment of hematologic tumors. Genetically engineered T cells used in CAR-T immunotherapy can specifically recognize and kill tumor cells expressing specific antigens without being restricted by MHC. The CAR-T immunotherapy has achieved good effects in the treatment of various B-cell malignant tumors, for example, CD19-targeted CAR-T cells for the treatment of acute lymphocytic leukemia (ALL), chronic lymphocytic leukemia (CLL), and non-Hodgkin's lymphoma (NHL). At the same time, clinical use of CAR-T cells for multiple myeloma and relapsed/refractory multiple myeloma is in progress and shows encouraging results.

B7H3, also referred to as CD276, belongs to the immunomodulatory protein B7 family and is a type I membrane protein with an extracellular domain sequence similar to those of other B7 family members. The B7H3 gene is located on human chromosome 15 and consists of ten exons, of which exons 4 to 7 encode extracellular IgV-IgC domains. mRNA of B7H3 is expressed in various normal tissues and some tumor cell lines, and is not detectable in peripheral blood mononuclear cells (PBMCs). However, the expression of B7H3 can be induced on dendritic cells and monocytes by inflammatory cytokines (IFNγ) and compositions of PMA and ionomycin. Although B7H3 mRNA is widely expressed in normal tissues, the expression level of B7H3 protein is extremely low or absent in normal tissues, indicating that the expression of B7H3 protein is subjected to strict post-transcriptional regulation. In contrast, the B7H3 protein is overexpressed in various malignant tumors and is associated with poor prognosis, relatively high tumor grade and tumor metastasis, drug resistance, and low overall survival.

The differential expression of B7H3 between tumors and healthy tissues makes it very suitable as a therapeutic target, since targeting this antigen results in very limited side effects. The results of preclinical studies have shown that the inhibition or reduction of B7H3 protein expression in tumor cells can reduce cell proliferation and glycolysis, and increase drug sensitivity of tumor cells.

A CAR-T cell therapy targeting B7H3 has been studied. One preclinical study demonstrated that anti-B7H3 CAR-T cells exhibit significant antitumor activity in vivo and can enable the established solid sarcomas in various xenograft models (including osteosarcoma, medulloblastoma, and Ewing's sarcoma) to be regressed.

However, autologous T cells of patients have difficulty expanding in vitro or reduced functions, resulting in an insufficient amount or poor quality of the CAR-T cell products prepared. Universal CAR-T cells are T cells isolated from healthy donors, and the prepared CAR-T cells not only have high amplification efficiency and strong activity, but also have an improved infection positive rate. However, the universal CAR-T also faces the problems of graft versus host disease (GVHD) and immune rejection. The CRISPR/Cas9 system is the most commonly used gene editing method, and can be used for producing T cells with TCR deficiency and HLA class I molecule deficiency, and for reducing immune rejection caused by allogeneic cell therapy.

SUMMARY

The present invention aims to prepare a universal CAR-T cell targeting B7H3, which recognizes a surface antigen of a tumor cell and knocks out TCR and HLA-A genes expressed by the cell at the same time, so that the immune rejection caused by an allogeneic CAR-T therapy is reduced, the survival time of the cell is prolonged, and the anti-tumor effect is improved.

In one aspect, the present application provides an antigen-binding polypeptide that binds to B7H3 and comprises at least one complementarity-determining region (CDR) of an antibody heavy chain variable region (VH), wherein the VH comprises an amino acid sequence set forth in SEQ ID NO: 25.

In certain embodiments, the VH comprises an amino acid sequence set forth in SEQ ID NO: 26, SEQ ID NO: 27, SEQ ID NO: 28, or SEQ ID NO: 29.

In certain embodiments, the antigen-binding polypeptide comprises a VH, wherein the VH comprises a heavy chain complementarity-determining region 1 (HCDR1), a heavy chain complementarity-determining region 2 (HCDR2), and a heavy chain complementarity-determining region 3 (HCDR3), and the HCDR3 comprises an amino acid sequence set forth in SEQ ID NO: 7.

In certain embodiments, the HCDR3 comprises an amino acid sequence set forth in SEQ ID NO: 8 or SEQ ID NO: 9.

In certain embodiments, the HCDR2 comprises an amino acid sequence set forth in SEQ ID NO: 4.

In certain embodiments, the HCDR2 comprises an amino acid sequence set forth in SEQ ID NO: 5 or SEQ ID NO: 6.

In certain embodiments, the HCDR1 comprises an amino acid sequence set forth in SEQ ID NO: 1.

In certain embodiments, the HCDR1 comprises an amino acid sequence set forth in SEQ ID NO: 2 or SEQ ID NO: 3.

In certain embodiments, the VH comprises: the HCDR1 comprising the amino acid sequence set forth in SEQ ID NO: 1, the HCDR2 comprising the amino acid sequence set forth in SEQ ID NO: 4, and the HCDR3 comprising the amino acid sequence set forth in SEQ ID NO: 7.

In certain embodiments, the VH comprises:
i) the HCDR1 comprising the amino acid sequence set forth in SEQ ID NO: 2, the HCDR2 comprising the amino acid sequence set forth in SEQ ID NO: 5, and the HCDR3 comprising the amino acid sequence set forth in SEQ ID NO: 8; or
ii) the HCDR1 comprising the amino acid sequence set forth in SEQ ID NO: 3, the HCDR2 comprising the amino acid sequence set forth in SEQ ID NO: 6, and the HCDR3 comprising the amino acid sequence set forth in SEQ ID NO: 9.

In certain embodiments, the VH comprises a heavy chain framework region 1 (HFR1), a heavy chain framework region 2 (HFR2), a heavy chain framework region 3 (HFR3), and a heavy chain framework region 4 (HFR4), and the HFR1 comprises an amino acid sequence set forth in SEQ ID NO: 10.

In certain embodiments, the HFRl comprises an amino acid sequence set forth in SEQ ID NO: 11, SEQ ID NO: 12, SEQ ID NO: 13, or SEQ ID NO: 14.

In certain embodiments, the HFR2 comprises an amino acid sequence set forth in SEQ ID NO: 15.

In certain embodiments, the HFR2 comprises an amino acid sequence set forth in SEQ ID NO: 16 or SEQ ID NO: 17.

In certain embodiments, the HFR3 comprises an amino acid sequence set forth in SEQ ID NO: 18.

In certain embodiments, the HFR3 comprises an amino acid sequence set forth in SEQ ID NO: 19, SEQ ID NO: 20, or SEQ ID NO: 21.

In certain embodiments, the HFR4 comprises an amino acid sequence set forth in SEQ ID NO: 22.

In certain embodiments, the HFR4 comprises an amino acid sequence set forth in SEQ ID NO: 23 or SEQ ID NO: 24.

In certain embodiments, the VH comprises HFR1, HFR2, HFR3, and HFR4, and the HFR1, HFR2, HFR3, and HFR4 are selected from:
i) the HFR1 comprising the amino acid sequence set forth in SEQ ID NO: 11, the HFR2 comprising the amino acid sequence set forth in SEQ ID NO: 16, the HFR3 comprising the amino acid sequence set forth in SEQ ID NO: 19, and the HFR4 comprising the amino acid sequence set forth in SEQ ID NO: 23;
ii) the HFR1 comprising the amino acid sequence set forth in SEQ ID NO: 12, the HFR2 comprising the amino acid sequence set forth in SEQ ID NO: 16, the HFR3 comprising the amino acid sequence set forth in SEQ ID NO: 20, and the HFR4 comprising the amino acid sequence set forth in SEQ ID NO: 24;
iii) the HFR1 comprising the amino acid sequence set forth in SEQ ID NO: 13, the HFR2 comprising the amino acid sequence set forth in SEQ ID NO: 17, the HFR3 comprising the amino acid sequence set forth in SEQ ID NO: 21, and the HFR4 comprising the amino acid sequence set forth in SEQ ID NO: 23; and
vi) the HFR1 comprising the amino acid sequence set forth in SEQ ID NO: 14, the HFR2 comprising the amino acid sequence set forth in SEQ ID NO: 17, the HFR3 comprising the amino acid sequence set forth in SEQ ID NO: 20, and the HFR4 comprising the amino acid sequence set forth in SEQ ID NO: 24.

In certain embodiments, the VH comprises an amino acid sequence set forth in SEQ ID NO: 25.

In certain embodiments, the VH comprises an amino acid sequence set forth in SEQ ID NO: 26, SEQ ID NO: 27, SEQ ID NO: 28, or SEQ ID NO: 29.

In certain embodiments, the antigen-binding polypeptide includes an antibody or an antigen-binding fragment thereof.

In certain embodiments, the antibody includes a monoclonal antibody, a polyclonal antibody, a dimer, a polymer, a multispecific antibody, an intact antibody, an antibody fragment, a human antibody, a humanized antibody, or a chimeric antibody.

In certain embodiments, the antigen-binding fragment includes a Fab fragment, an Fv fragment, F(ab')$_2$, a single-chain Fv (scFv), or a single-domain antibody (VHH).

In another aspect, the present application provides a chimeric antigen receptor (CAR) comprising a targeting moiety, wherein the targeting moiety comprises the aforementioned antigen-binding polypeptide.

In certain embodiments, the targeting moiety includes a VHH.

In certain embodiments, the chimeric antigen receptor comprises a transmembrane domain, wherein the transmembrane domain comprises a transmembrane domain derived from one or more proteins selected from the group consisting of: CD8A, CD8B, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4 (CD244), FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, and SLAM.

In certain embodiments, the transmembrane domain comprises a transmembrane domain derived from CD8A.

In certain embodiments, the transmembrane domain comprises an amino acid sequence set forth in any one of SEQ ID NO: 42 to SEQ ID NO: 90.

In certain embodiments, the chimeric antigen receptor comprises an intracellular co-stimulatory signaling domain, wherein the intracellular co-stimulatory signaling domain comprises an intracellular co-stimulatory signaling domain derived from one or more proteins selected from the group consisting of: CD28, CD137, CD27, CD2, CD7, CD8A, CD8B, OX40, CD226, DR3, SLAM, CDS, ICAM-1, NKG2D, NKG2C, B7H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, and MyD88.

In certain embodiments, the intracellular co-stimulatory signaling domain is derived from a co-stimulatory signaling domain of 4-1BB.

In certain embodiments, the intracellular co-stimulatory signaling domain comprises an amino acid sequence set forth in any one of SEQ ID NO: 91 to SEQ ID NO: 123.

In certain embodiments, the chimeric antigen receptor comprises an intracellular signaling domain, wherein the intracellular signaling domain comprises an intracellular signaling domain derived from one or more proteins selected from the group consisting of: CD3ζ, CD3δ, CD3γ, CD3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

In certain embodiments, the intracellular signaling domain comprises a signaling domain derived from CD3ζ.

In certain embodiments, the intracellular signaling domain comprises an amino acid sequence set forth in any one of SEQ ID NO: 107, SEQ ID NO: 111, SEQ ID NO: 112, and SEQ ID NO: 124 to SEQ ID NO: 134.

In certain embodiments, the chimeric antigen receptor comprises a hinge region between the targeting moiety and the transmembrane domain, wherein the hinge region comprises a hinge region derived from one or more proteins selected from the group consisting of: CD28, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, and LIGHT.

In certain embodiments, the hinge region comprises a hinge region derived from CD8A.

In certain embodiments, the hinge region comprises an amino acid sequence set forth in any one of SEQ ID NO: 135 to SEQ ID NO: 156.

In certain embodiments, a non-targeting moiety of the chimeric antigen receptor comprises a transmembrane domain of CD8A molecule, a hinge region of CD8A, an intracellular co-stimulatory signaling domain of 4-1BB, and an intracellular signaling domain of CD3ζ.

In certain embodiments, the non-targeting moiety of the chimeric antigen receptor comprises an amino acid sequence set forth in SEQ ID NO: 30.

In certain embodiments, the chimeric antigen receptor further comprises a signal peptide fragment, wherein the C-terminus of the signal peptide fragment is linked to the N-terminus of the targeting moiety.

In certain embodiments, the signal peptide fragment includes a CD8A signal peptide fragment.

In certain embodiments, the signal peptide fragment comprises an amino acid sequence set forth in SEQ ID NO: 31.

In certain embodiments, the chimeric antigen receptor comprises an amino acid sequence set forth in any one of SEQ ID NO: 32, SEQ ID NO: 33, SEQ ID NO: 34, and SEQ ID NO: 35.

In another aspect, the present application provides one or more isolated nucleic acid molecules encoding the aforementioned antigen-binding polypeptide or the aforementioned chimeric antigen receptor.

In certain embodiments, the isolated nucleic acid molecule comprises a nucleotide sequence set forth in any one of SEQ ID NO: 36, SEQ ID NO: 37, SEQ ID NO: 38, and SEQ ID NO: 39.

In another aspect, the present application provides a vector comprising the aforementioned isolated nucleic acid molecule.

In certain embodiments, the vector is an expression vector.

In certain embodiments, the vector is selected from a DNA vector, an RNA vector, a plasmid, a lentiviral vector, an adenoviral vector, an adeno-associated viral vector, and a retroviral vector.

In another aspect, the present application provides a cell i) comprising the aforementioned isolated nucleic acid molecule or the aforementioned vector; and/or ii) expressing the aforementioned antigen-binding polypeptide or chimeric antigen receptor.

In another aspect, the present application provides an immune effector cell comprising the aforementioned nucleic acid molecule or the aforementioned vector, and/or expressing the aforementioned CAR.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

In certain embodiments, the immune effector cell includes an autologous or non-autologous immune effector cell.

In certain embodiments, the immune effector cell includes a modified immune effector cell.

In certain embodiments, the modified immune effector cell includes a cell that reduces immune rejection caused by allogeneic cell therapy.

In certain embodiments, the functions of a T cell antigen receptor (TCR) and major histocompatibility complexes (MHCI, MHCII) in the modified immune effector cell are inhibited in a T cell.

In certain embodiments, the modification comprises down-regulation of the expression and/or activity of one or more of immune rejection-related genes.

In certain embodiments, the immune rejection-related gene is selected from one or more of the following groups: TRAC, TRBC, HLA-A, HLA-B, B2M, and CIITA.

In certain embodiments, the expression and/or activity of the TRAC gene and the HLA-A gene in the modified immune effector cell is down-regulated as compared to a corresponding unmodified cell.

In certain embodiments, the expression and/or activity of the CIITA gene in the modified immune effector cell is not down-regulated as compared to the corresponding unmodified cell.

In certain embodiments, the expression and/or activity of the B2M gene in the modified immune effector cell is not down-regulated as compared to the corresponding unmodified cell.

In certain embodiments, the expression and/or activity of the TRAC gene and the HLA-A gene in the modified immune effector cell is down-regulated as compared to a corresponding wild-type cell.

In certain embodiments, the expression and/or activity of the B2M gene in the modified immune effector cell is not down-regulated as compared to the corresponding wild-type cell.

In certain embodiments, the expression and/or activity of the CIITA gene in the modified immune effector cell is not down-regulated as compared to the corresponding wild-type cell.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene knockout, gene mutation, and/or gene silencing.

In certain embodiments, the modification comprises knocking out either of two TRAC alleles and knocking out either of two HLA-A alleles in the immune effector cell.

In certain embodiments, the modification comprises knocking out the two TRAC alleles and knocking out either of the two HLA-A alleles in the immune cell.

In certain embodiments, the modification comprises knocking out an exon of the TRAC gene and knocking out an exon of the HLA-A gene in the immune cell.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification further comprises administering to the immune effector cell sgRNA targeting an exon portion of the TRAC gene.

In certain embodiments, the sgRNA targeting the exon portion of the TRAC gene comprises a nucleotide sequence set forth in any one of SEQ ID NO: 157 to SEQ ID NO: 171.

In certain embodiments, the modification comprises administering to the immune effector cell sgRNA targeting an exon portion of the HLA-A gene.

In certain embodiments, the sgRNA targeting the exon portion of the HLA-A gene comprises a nucleotide sequence set forth in any one of SEQ ID NO: 172 to SEQ ID NO: 212.

In certain embodiments, the modification further comprises administering to the cell a Cas enzyme.

In certain embodiments, the Cas enzyme includes a Cas9 protein.

In certain embodiments, the antisense RNA comprises a nucleotide sequence set forth in any one of SEQ ID NO: 213 to SEQ ID NO: 216.

In certain embodiments, the immune effector cell is an HLA-B homozygous cell.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the immune effector cell is an HLA-A homozygous or heterozygous cell.

In certain embodiments, the HLA-A homozygote or heterozygote includes HLA-A*02 homozygote, HLA-A*11 homozygote, HLA-A*02/A*11 heterozygote, or HLA-A*24 homozygote.

In another aspect, the present application provides a method for preparing an immune effector cell, which comprises introducing the aforementioned nucleic acid molecule or the aforementioned vector into the immune effector cell.

In certain embodiments, the method further comprises: modifying the immune effector cell before/after introducing the nucleic acid molecule according to the present disclosure or the vector according to the present disclosure into the immune effector cell, wherein the modification comprises down-regulation of the expression and/or activity of one or more of immune rejection-related genes.

In certain embodiments, the immune rejection-related gene is selected from one or more of the following groups: TRAC, TRBC, HLA-A, HLA-B, B2M, and CIITA.

In certain embodiments, the expression and/or activity of the TRAC gene and the HLA-A gene in the immune effector cell is down-regulated as compared to the expression and/or activity of a corresponding gene in a corresponding unmodified cell.

In certain embodiments, the expression and/or activity of the CIITA gene is not down-regulated as compared to the expression and/or activity of the corresponding gene in the corresponding unmodified cell.

In certain embodiments, the expression and/or activity of the B2M gene is not down-regulated as compared to the expression and/or activity of the corresponding gene in the corresponding unmodified cell.

In certain embodiments, the expression and/or activity of the TRAC gene and the HLA-A gene in the immune effector cell is down-regulated as compared to a corresponding wild-type cell.

In certain embodiments, the expression and/or activity of the CIITA gene is not down-regulated as compared to the corresponding wild-type cell.

In certain embodiments, the expression and/or activity of the B2M gene is not down-regulated as compared to the corresponding wild-type cell.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene knockout, gene mutation, and/or gene silencing.

In certain embodiments, the modification comprises knocking out either of two TRAC alleles and knocking out either of two HLA-A alleles in the immune effector cell.

In certain embodiments, the modification comprises knocking out the two TRAC alleles and knocking out either of the two HLA-A alleles in the immune cell.

In certain embodiments, the modification comprises knocking out an exon of the TRAC gene and knocking out an exon of the HLA-A gene in the immune cell.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification comprises administering to the immune effector cell sgRNA targeting an exon portion of the TRAC gene.

In certain embodiments, the sgRNA targeting the exon portion of the TRAC gene comprises a nucleotide sequence set forth in any one of SEQ ID NO: 157 to SEQ ID NO: 171.

In certain embodiments, the modification comprises administering to the immune effector cell sgRNA targeting an exon portion of the HLA-A gene.

In certain embodiments, the sgRNA targeting the exon portion of the HLA-A gene comprises a nucleotide sequence set forth in any one of SEQ ID NO: 172 to SEQ ID NO: 212.

In certain embodiments, the modification further comprises administering to the cell a Cas enzyme.

In certain embodiments, the Cas enzyme includes a Cas9 protein.

In certain embodiments, the antisense RNA comprises a nucleotide sequence set forth in any one of SEQ ID NO: 213 to SEQ ID NO: 216.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

In certain embodiments, the immune effector cell includes an autologous or non-autologous immune effector cell.

In certain embodiments, the cell is an HLA-B homozygous cell.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the cell is an HLA-A homozygous or heterozygous cell.

In certain embodiments, the HLA-A homozygote or heterozygote includes HLA-A*02 homozygote, HLA-A*11 homozygote, HLA-A*02/A*11 heterozygote, or HLA-A*24 homozygote.

In another aspect, the present application provides use of the aforementioned chimeric antigen receptor, the aforementioned isolated nucleic acid molecule, the aforementioned vector, the aforementioned cell, or the aforementioned immune effector cell in the preparation of a CAR-T cell.

In another aspect, the present application provides a pharmaceutical composition comprising the aforementioned antigen-binding polypeptide, the aforementioned chimeric antigen receptor, the aforementioned isolated nucleic acid molecule, the aforementioned vector, the aforementioned cell, and/or the aforementioned immune effector cell, and optionally a pharmaceutically acceptable carrier.

In another aspect, the present application provides use of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition in the treatment of a disease or disorder associated with the expression of B7H3.

In certain embodiments, the disease or disorder associated with the expression of B7H3 includes a disease or disorder associated with up-regulation of the expression of B7H3.

In certain embodiments, the disease or disorder associated with the expression of B7H3 includes cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

In another aspect, the present application provides use of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition in the preparation of a medicament for treating cancer.

In certain embodiments, the cancer includes a B7H3-positive cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

In another aspect, the present application provides a method for preventing or treating a disease or disorder associated with the expression of B7H3, comprising administering to a subject in need thereof an effective amount of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition.

In certain embodiments, the disease or disorder associated with the expression of B7H3 includes a disease or disorder associated with up-regulation of the expression of B7H3.

In certain embodiments, the disease or disorder associated with the expression of B7H3 includes cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

Other aspects and advantages of the present application will be readily apparent to those skilled in the art from the following detailed description. Only exemplary embodiments of the present application have been shown and described in the following detailed description. As will be recognized by those skilled in the art, the content of the present application enables those skilled in the art to make changes to the specific embodiments disclosed without departing from the spirit and scope of the invention to which the present application pertains. Accordingly, descriptions in the drawings and specification are only illustrative rather than restrictive.

BRIEF DESCRIPTION OF THE DRAWINGS

Specific features of the invention to which the present application pertains are set forth in appended claims. Features and advantages of the invention to which the present application pertains will be better understood by reference to the exemplary embodiments and drawings described in detail below. The drawings are briefly described as follows:

Figures 14, 15:
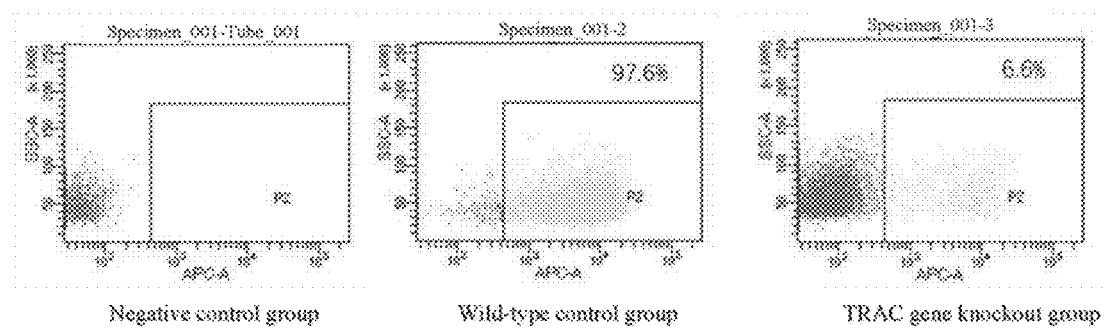
Figure 16:
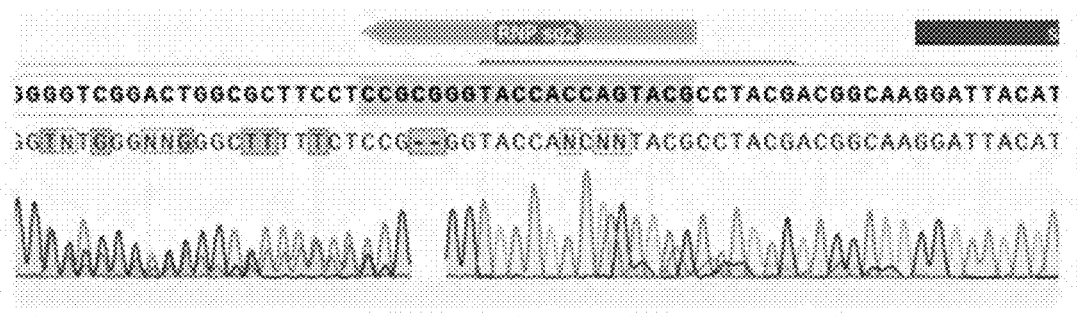
Figure 17:
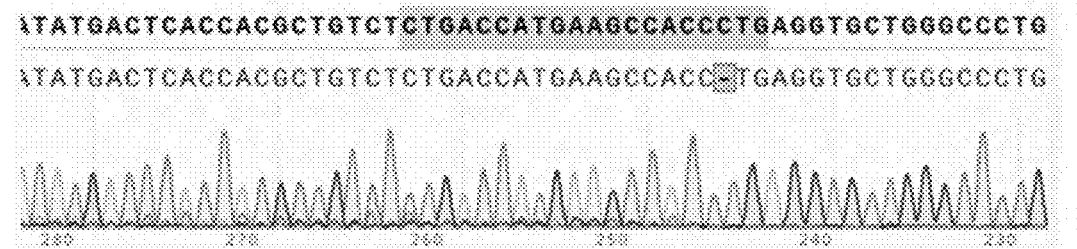
Figure 18:
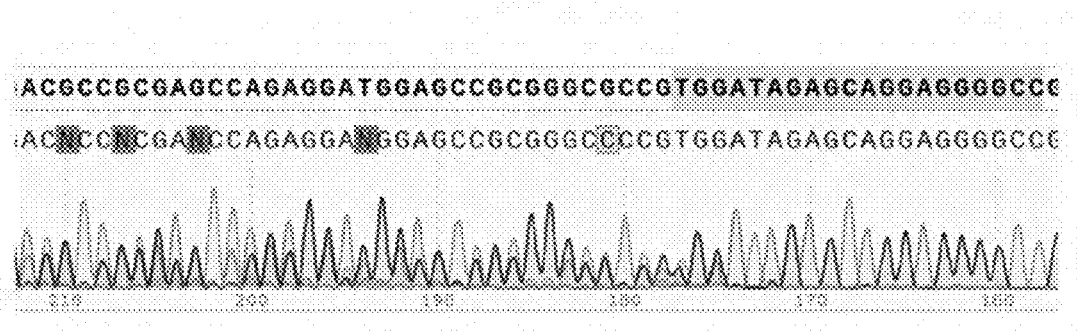
Figure 19:
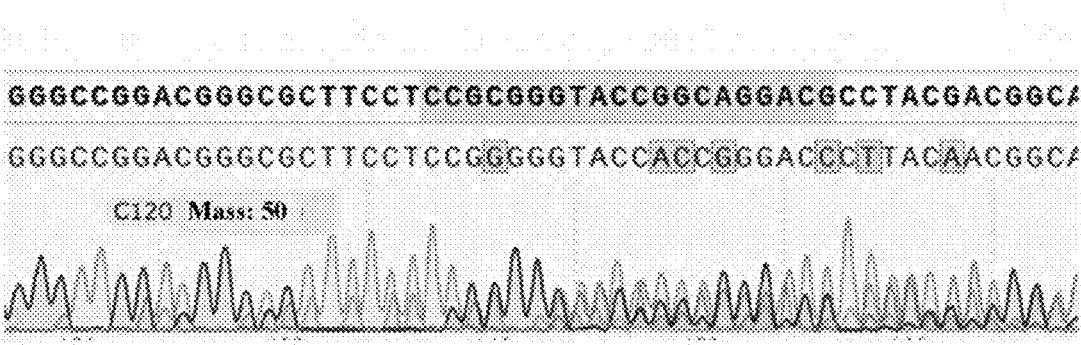
Figure 20A:
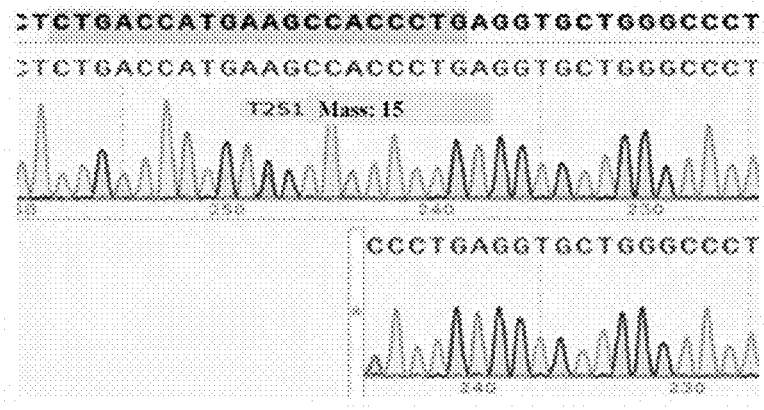
Figure 20B:
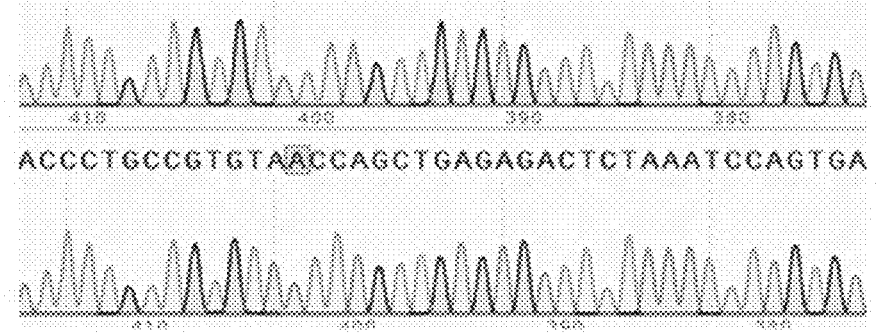
Figure 21A:
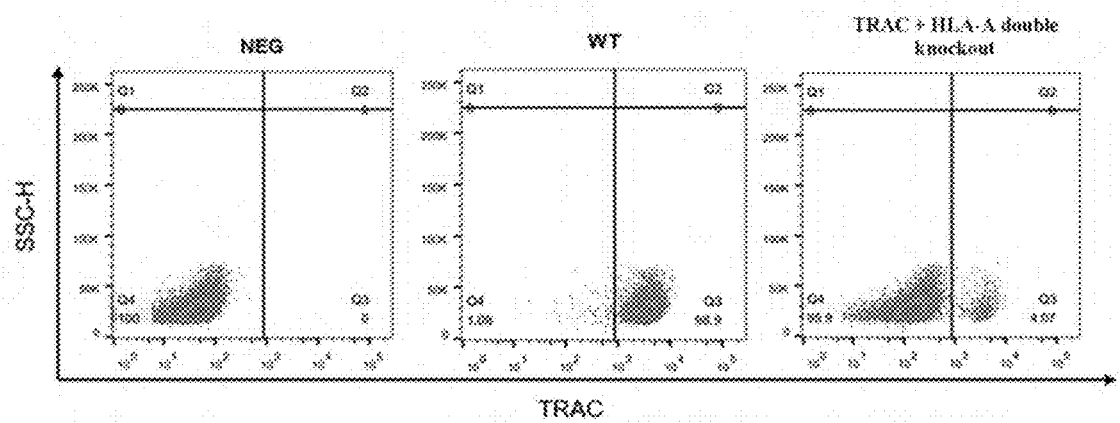
Figure 21B:
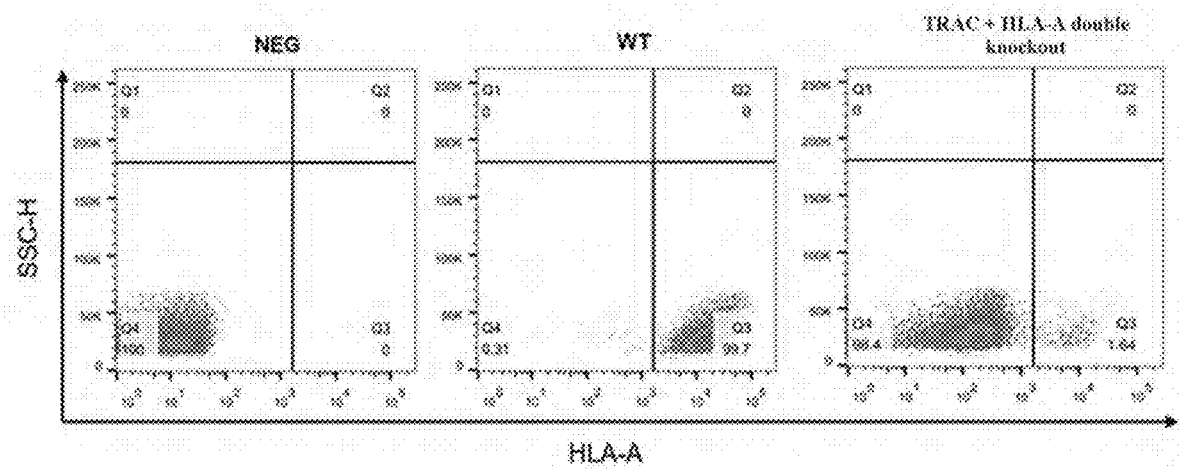
Figure 22:
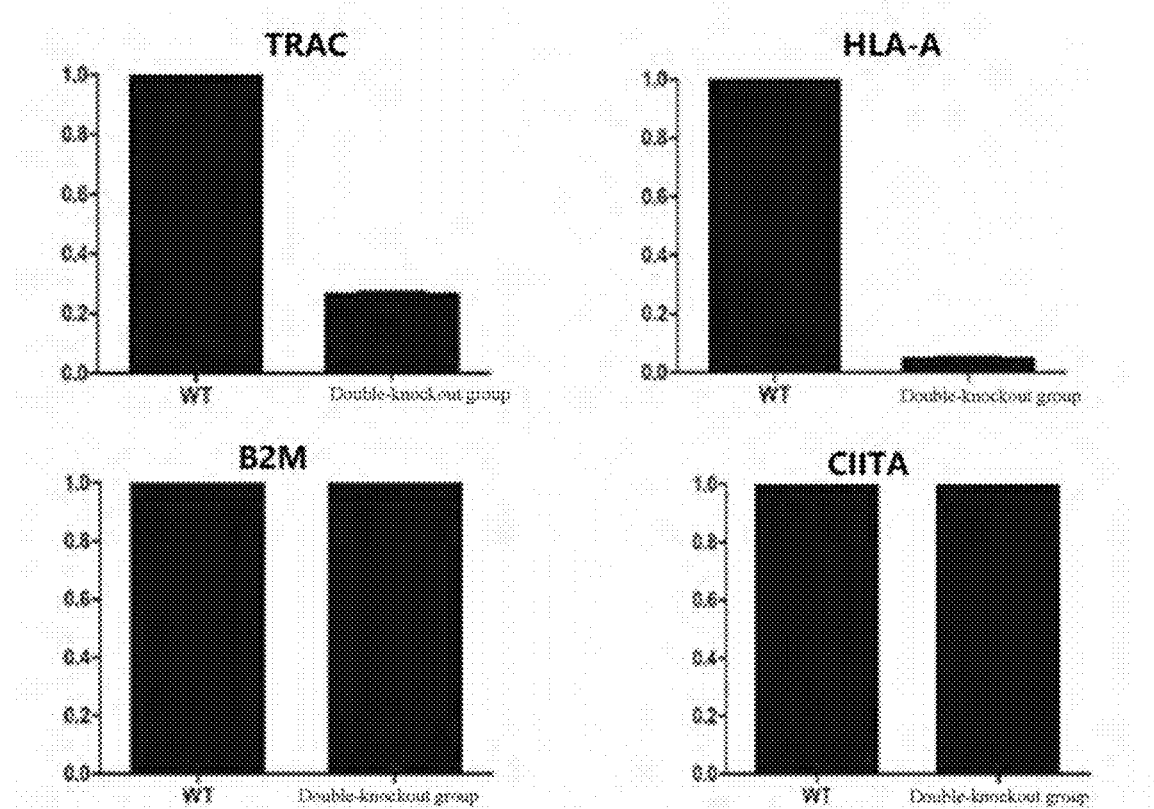
Figure 23A:
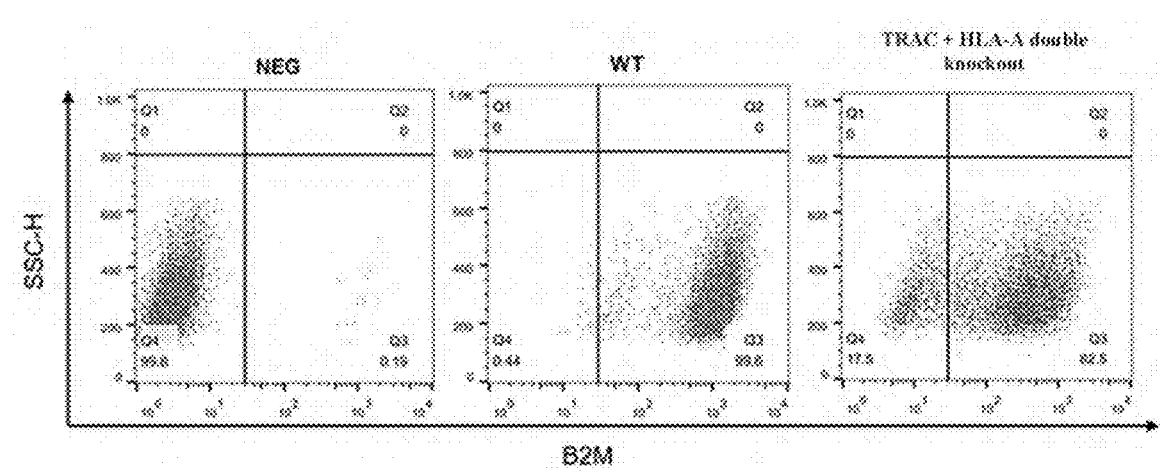
Figure 23B:
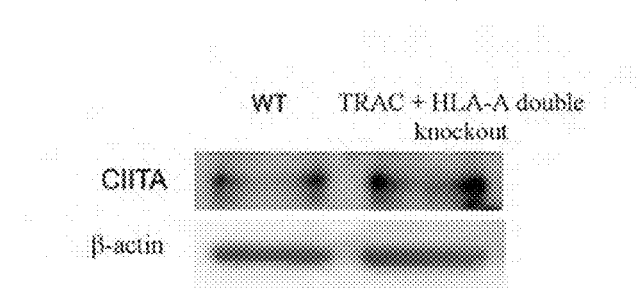
Figure 25A:
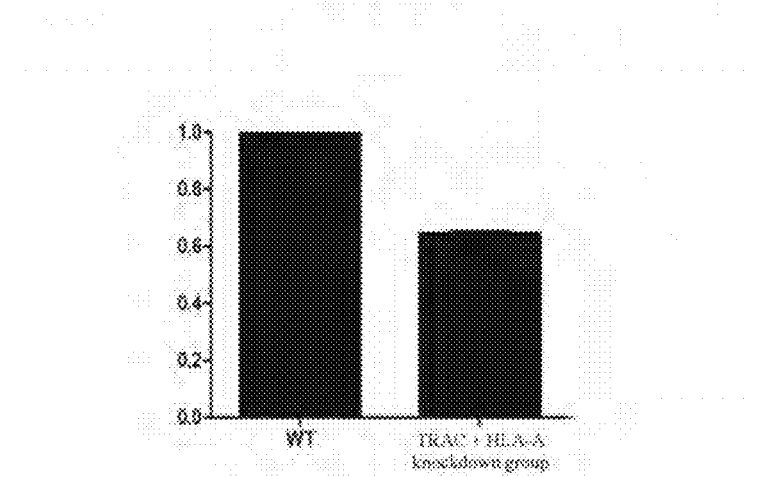
Figure 25B:
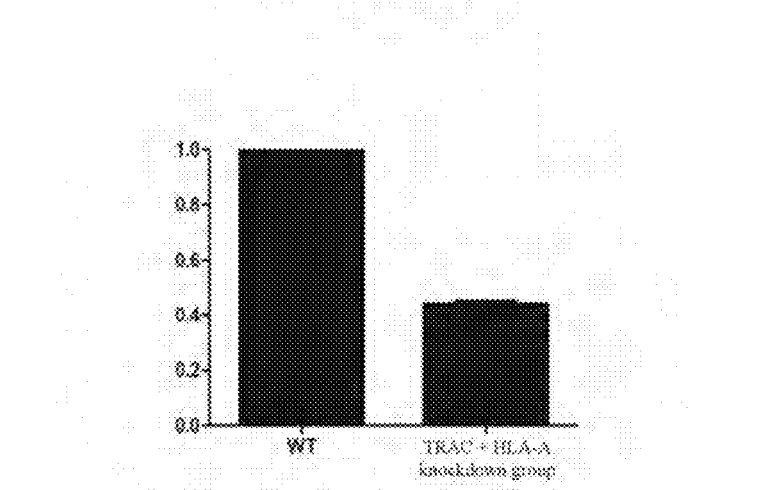
Figure 26A:
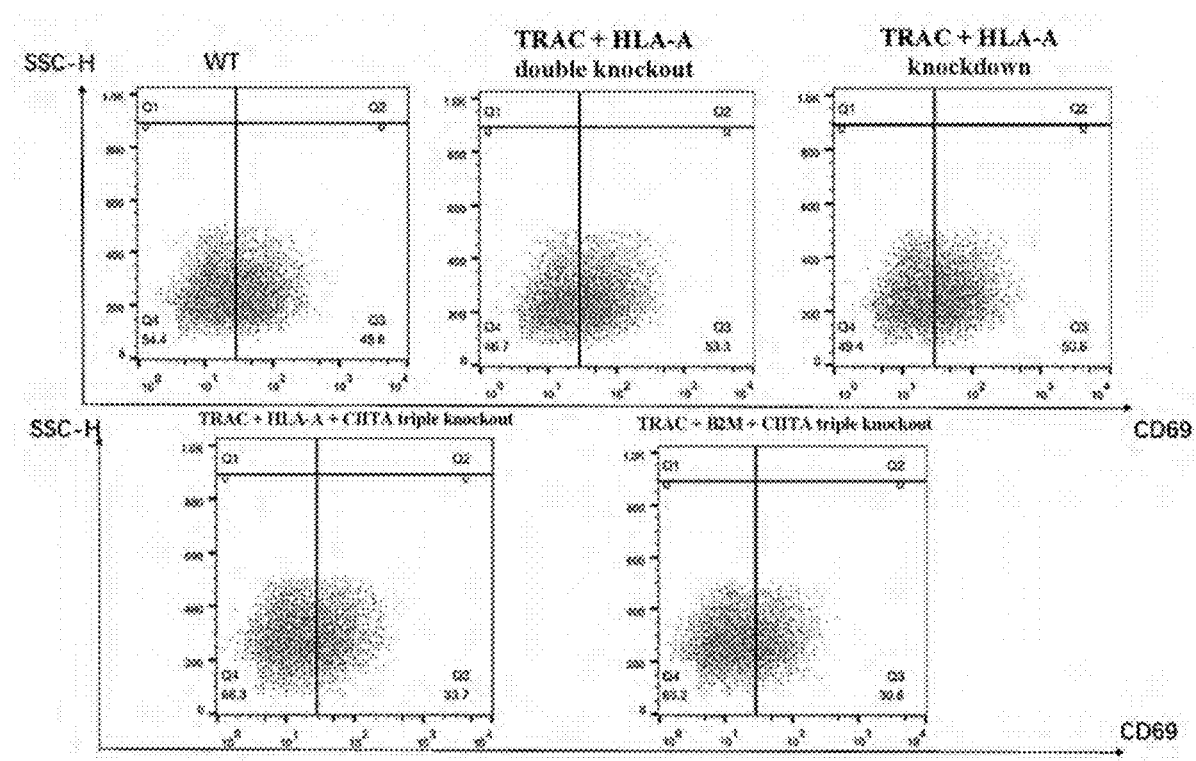
Figure 26B:
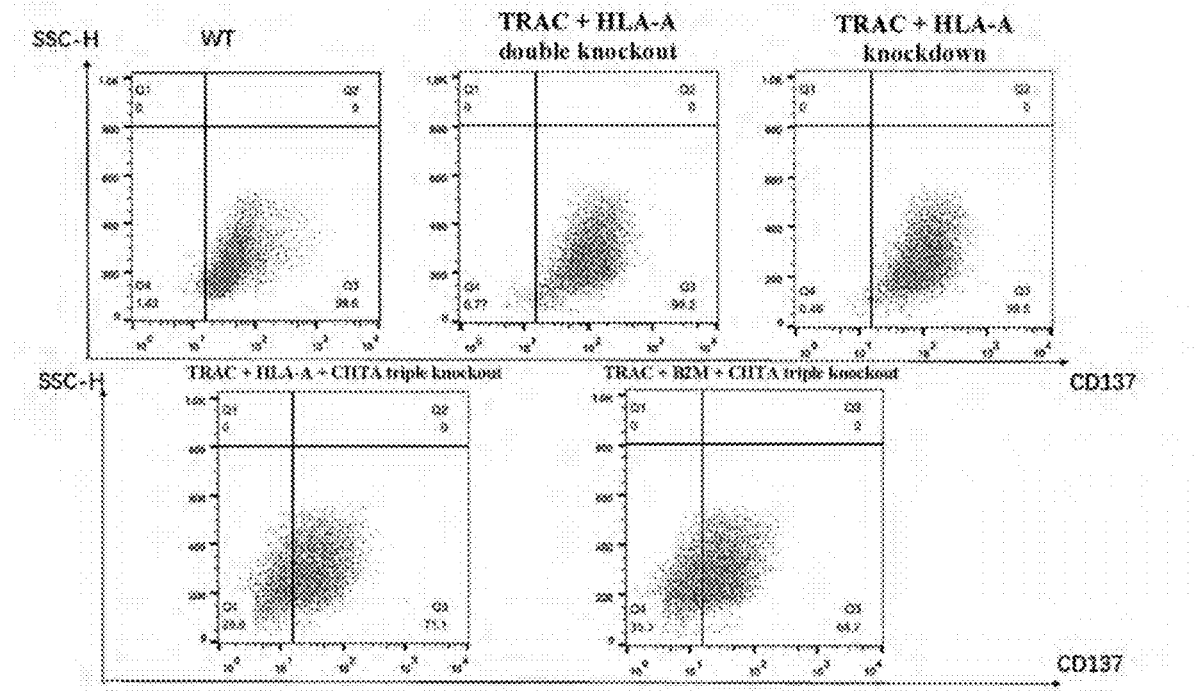
Figure 27:
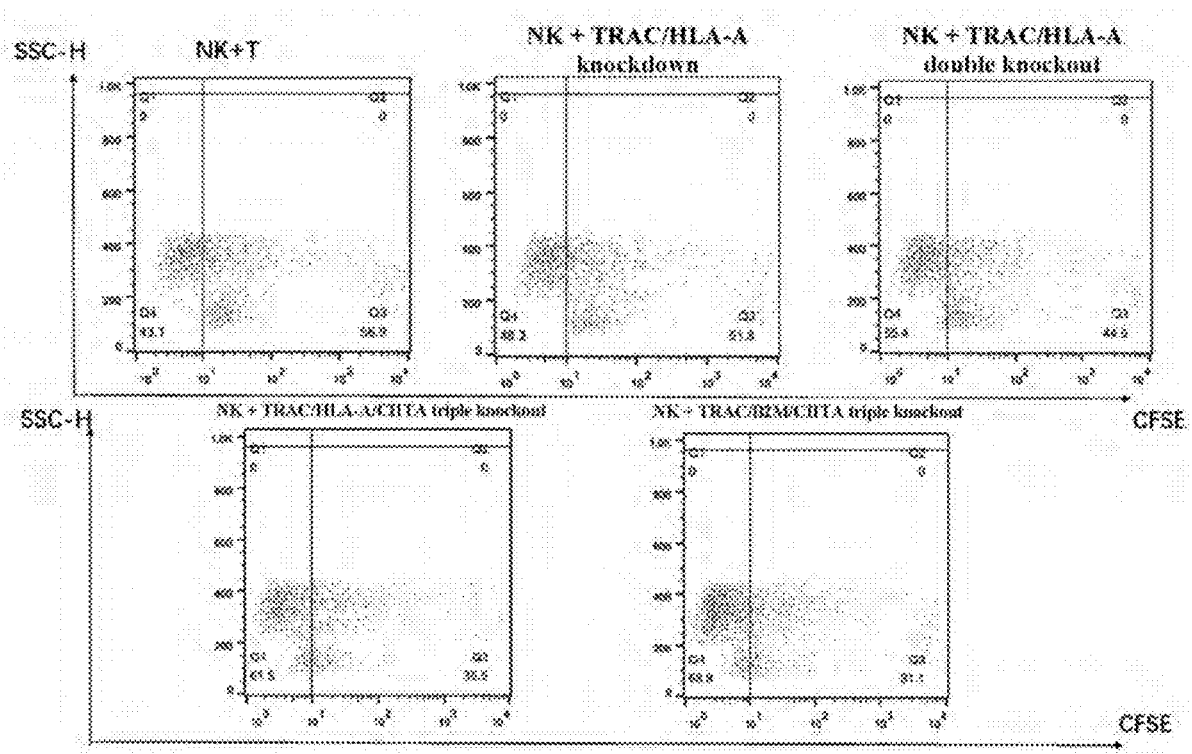
Figure 28:
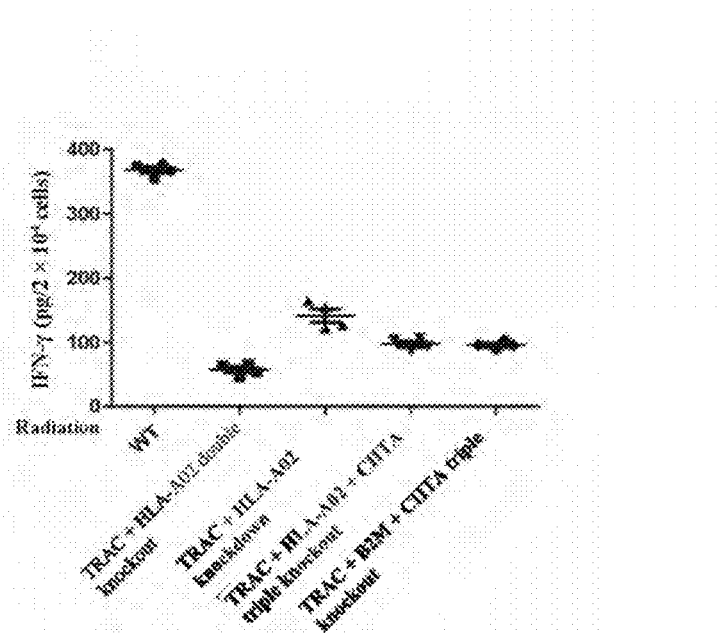
Figure 30:
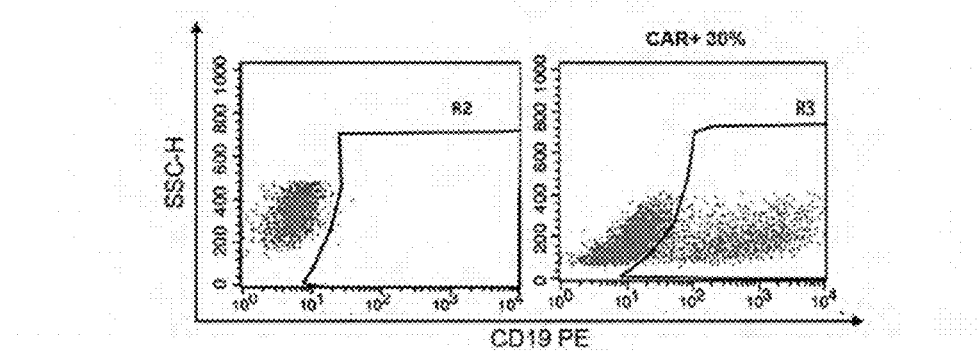
Figure 31:
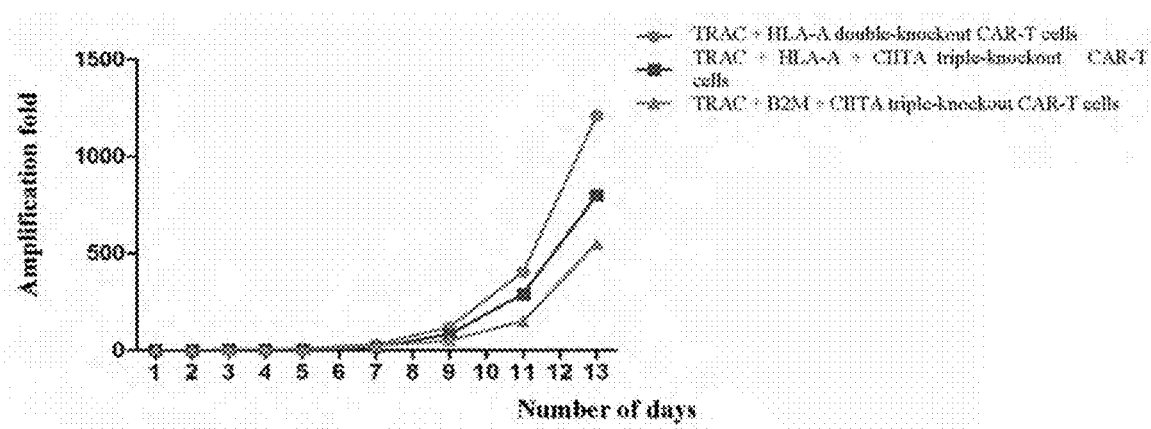
Figure 32:
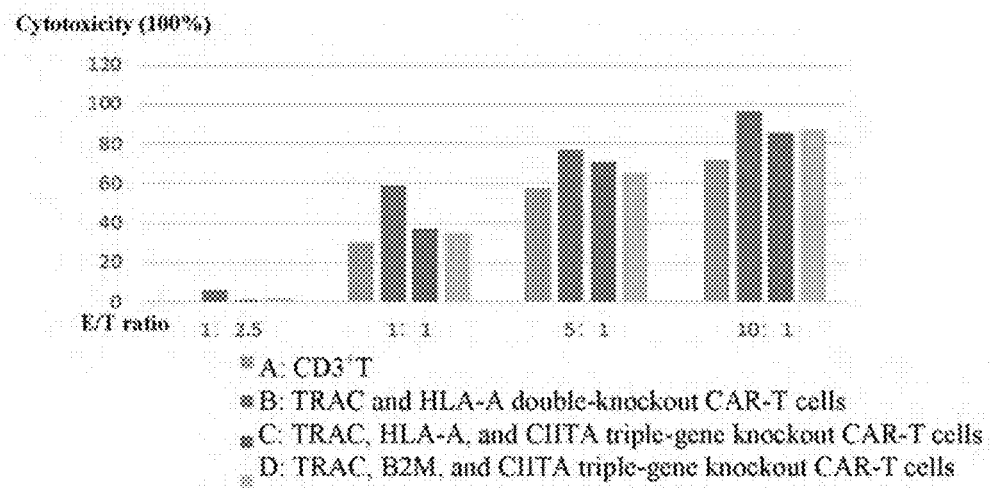
Figure 33:
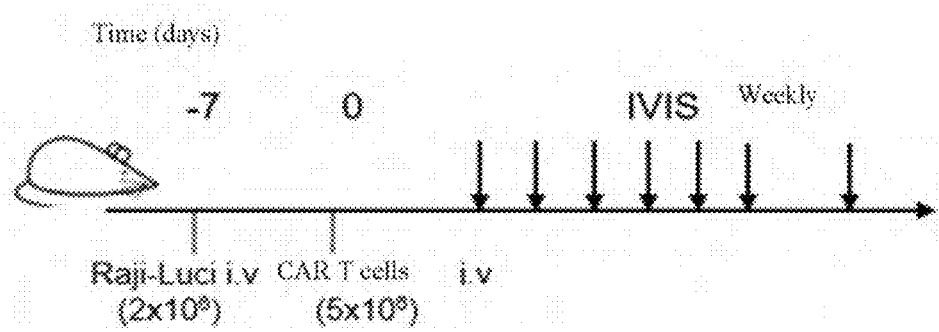
Figure 34:
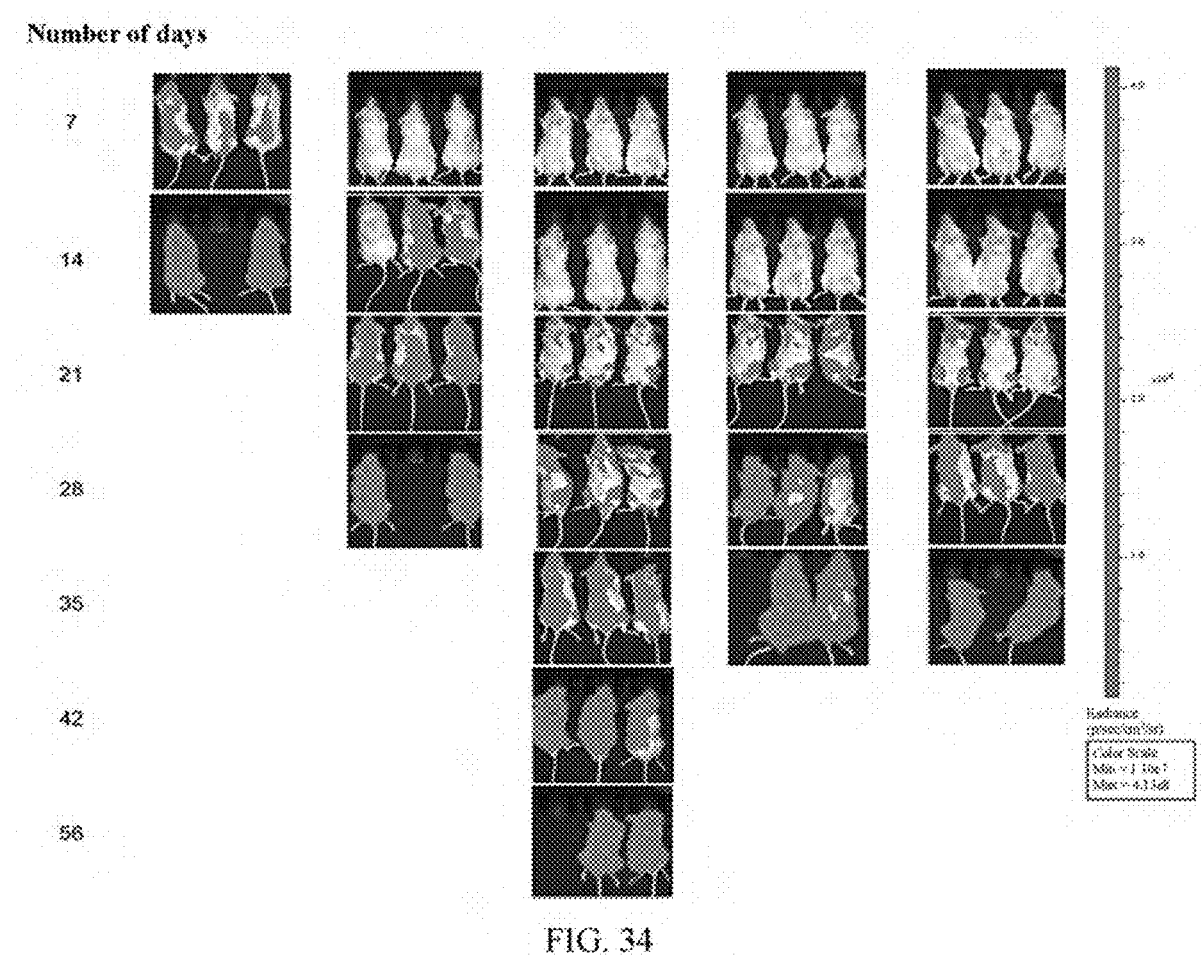

FIG. 14 shows TA cloning assay results of the TRAC gene after Sg9RNA editing in the present application, FIG. 14 comprises nucleotide sequences set forth in SEQ ID NO: 219 (line 1 and line 3). SEQ ID NO: 220(line 2), SEQ ID NO: 221(line 4), SEQ ID NO: 222(line 5, line 7, line 9, line 11 and line 13), SEQ ID NO: 223(line 6), SEQ ID NO: 224(line 8), SEQ ID NO: 225(10), SEQ ID NO: 226(line 12), SEQ ID NO: 227(line 14) and SEQ ID NO: 228(line 15);

FIG. 15 shows flow cytometry assay results of the TRAC gene after Sg9RNA editing in the present application;

FIG. 16 shows the Sanger sequencing results of HLA-A02 gene after Sg2RNA editing in the present application, FIG. 16 comprises nucleotide sequences set forth in SEQ ID NO: 229(line 1) and SEQ ID NO: 230(line 2);

FIG. 17 shows the Sanger sequencing results of HLA-A02 gene after Sg5RNA editing in the present application, FIG. 17 comprises nucleotide sequences set forth in SEQ ID NO: 231(line 1) and SEQ ID NO: 232(line 2);

FIG. 18 shows the Sanger sequencing results of HLA-A11 gene after Sg21RNA editing in the present application, FIG. 18 comprises nucleotide sequences set forth in SEQ ID NO: 233(line 1) and SEQ ID NO: 234(line 2);

FIG. 19 shows the Sanger sequencing results of HLA-A11 gene after Rsg2RNA editing in the present application, FIG. 19 comprises nucleotide sequences set forth in SEQ ID NO: 235(line 1) and SEQ ID NO: 236(line 2);

FIGS. 20A-20B show results of simultaneous knockout of HLA-A02 and TRAC in the modified immune effector cells of the present application, FIG. 20A comprises nucleotide sequences set forth in SEQ ID NO: 237(line 1 and line 2) and SEQ ID NO: 238(line 3), FIG. 20B comprises nucleotide sequences set forth in SEQ ID NO: 239(line 1 and line 2) and SEQ ID NO: 240(line 3);

FIGS. 21A-21B show protein levels of HLA-A02 and TRAC in the modified immune effector cells of the present application;

FIG. 22 shows mRNA levels of TRAC, HLA-A, B2M, and CIITA in the modified immune effector cells of the present application;

FIGS. 23A-23B show protein levels of B2M and CIITA in the modified immune effector cells of the present application;

FIGS. 24A-24D show protein levels of TRAC, HLA-A, B2M, and CIITA in the modified immune effector cells of the present application;

FIGS. 25A-25B show the knockout of TRAC and HLA-A at mRNA levels in the modified immune effector cells of the present application;

FIGS. 26A-26B show protein levels of CD69 and CD137 in the modified immune effector cells of the present application;

FIG. 27 shows the co-culture of the modified immune effector cells of the present application and NK cells;

FIG. 28 shows the expression level of IFN-γ in the modified immune effector cells of the present application;

FIGS. 29A-29D show protein levels of TRAC, HLA-A, B2M, and CIITA in the modified immune effector cells of the present application;

FIG. 30 shows the infection efficiency of the modified immune effector cells of the present application on CARs;

FIG. 31 shows amplification folds of the modified immune effector cells of the present application;

FIG. 32 shows a killing effect of the modified immune effector cells of the present application on CD19-positive target cells;

FIG. 33 shows a dosing regimen for administering the modified immune effector cells of the present application; and FIG. 34 shows a killing effect of the modified immune effector cells of the present application on tumors in mice.

DETAILED DESCRIPTION

The embodiments of the present invention are described below with reference to specific examples, and other advantages and effects of the present invention will be readily apparent to those skilled in the art from the disclosure of the present specification.

Definitions of Terms

In the present application, the term "chimeric antigen receptor" or "CAR" generally refers to a group of polypeptides, generally two types in the simplest embodiment, which, when in an immune effector cell, provide the cell with specificity for a target cell (generally a cancer cell) and produce an intracellular signal. In some embodiments, the CAR comprises at least one extracellular antigen-binding domain (such as a VHH, scFv, or a portion thereof), a transmembrane domain, and a cytoplasmic signaling domain (also referred to herein as an "intracellular signaling domain") that comprises a functional signaling domain derived from a stimulatory molecule and/or a co-stimulatory molecule as defined below. In some embodiments, the group of polypeptides are in the same polypeptide chain (e.g., comprise a chimeric fusion protein). In some embodiments, the group of polypeptides are not contiguous with each other, e.g., in different polypeptide chains. In some aspects, the group of polypeptides includes a dimerization switch that can couple the polypeptides to each other in the presence of a dimerization molecule, e.g., can couple an antigen-binding domain to an intracellular signaling domain. In one aspect, the stimulatory molecule of the CAR is a ζ chain associated with a T cell receptor complex. In one aspect, the cytoplasmic signaling domain comprises a primary signaling domain (e.g., a primary signaling domain of CD3-ζ). In one aspect, the cytoplasmic signaling domain further comprises one or more functional signaling domains derived from at least one co-stimulatory molecule as defined below. In one aspect, the co-stimulatory molecule may be selected from 4-1BB (i.e., CD137), CD27, ICOS, and/or CD28. In one aspect, the CAR comprises a chimeric fusion protein, which may comprise an extracellular antigen recognition domain, a transmembrane domain, and an intracellular signaling domain comprising a functional signaling domain derived from a stimulatory molecule. In one aspect, the CAR comprises a chimeric fusion protein, which may comprise an extracellular antigen recognition domain, a transmembrane domain, and an intracellular signaling domain comprising a functional signaling domain derived from a co-stimulatory molecule and a functional signaling domain derived from a stimulatory molecule. In one aspect, the CAR comprises a chimeric fusion protein, which may comprise an extracellular antigen recognition domain, a transmembrane domain, and an intracellular signaling domain comprising a functional signaling domain derived from one or more co-stimulatory molecules and a functional signaling domain derived from a stimulatory molecule. In one aspect, the CAR comprises a chimeric fusion protein, which may comprise an extracellular antigen recognition domain, a transmembrane domain, and an intracellular signaling domain comprising at least two functional signaling domains derived from one or more co-stimulatory molecules and a functional signaling domain derived from a stimulatory molecule. In one aspect, the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., VHH) during cell processing and localizes the CAR to the cell membrane.

In the present application, the term "antibody" is generally meant to be used in the broadest sense and specifically encompasses monoclonal antibodies, polyclonal antibodies, dimers, polymers, multispecific antibodies (e.g., bispecific antibodies), and antibody fragments so long as they exhibit the desired biological activity (Miller et al., (2003) *Jour. of Immunology* 170: 4854-4861). The antibody may be a murine antibody, a human antibody, a humanized antibody, or a chimeric antibody, or derived from other species.

A full-length antibody typically refers to an antibody that consists of two "full-length antibody heavy chains" and two "full-length antibody light chains". The "Full-length antibody heavy chain" generally refers to a polypeptide consisting of, from the N-terminus to the C-terminus, an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and, in the case of antibodies of the IgE subclass, optionally further comprising an antibody heavy chain constant domain 4 (CH4). In some embodiments, the "full-length antibody heavy chain" is a polypeptide consisting of, from the N-terminus to the C-terminus, VH, CH1, HR, CH2, and CH3. The "full-length antibody light chain" is generally a polypeptide consisting of, from the N-terminus to the C-terminus, an antibody light chain variable domain (VL) and an antibody light chain constant domain (CL), abbreviated as VL-CL. The antibody light chain constant domain (CL) may be κ(kappa) or λ(lambda). The two full-length antibody chains are linked together by inter-polypeptide disulfide bonds between the CL domain and the CH1 domain and between the hinge regions of the full-length antibody heavy chains. Examples of typical full-length antibodies are natural antibodies such as IgG (e.g., IgG1 and IgG2), IgM, IgA, IgD, and IgE.

In the present application, the term "antigen-binding fragment" (also referred to herein as a "targeting moiety" or "antigen-binding moiety") generally refers to a portion of an antibody molecule, which comprises amino acids responsible for specific binding between an antibody and an antigen. The portion of the antigen specifically recognized and bound by the antibody is referred to as an "epitope" described above. The antigen-binding domain may typically comprise an antibody light chain variable region (VL) and an antibody heavy chain variable region (VH); however, it does not necessarily comprise both. An Fd fragment, for example, has two VH regions and generally retains some of the antigen-binding functions of the intact antigen-binding domain. Examples of antigen-binding fragments of antibodies include: (1) a Fab fragment, a monovalent fragment having a VL, a VH, a constant light chain (CL) and a CH1 domain; (2) an F(ab')$_2$ fragment, a bivalent fragment having two Fab fragments linked by a disulfide bridge at the hinge region; (3) an Fd fragment, having two VH and CH1 domains; (4) an Fv fragment, having VL and VH domains of a single arm of an antibody; (5) a dAb fragment (Ward et al., "Binding Activities of a Repertoire of Single Immunoglobulin Variable Domains Secreted From Escherichia coli", *Nature* 341: 544-546 (1989), which is incorporated herein by reference in its entirety), having a VH domain; (6) an isolated complementarity-determining region (CDR); (7) a single-chain Fv (scFv), e.g., derived from an scFV-library. Although the two domains of the Fv fragment, VL and VH, are encoded by separate genes, they may be joined by a recombinant method using a synthetic linker that allows them to be prepared as a single protein chain in which the VL and VH regions pair to form monovalent molecules (referred to as single-chain Fv (scFv)) (see, e.g., Huston et al., "Protein Engineering of Antibody Binding Sites: Recovery of Specific Activity in an Anti-Digoxin Single-Chain Fv Analogue Produced in Escherichia coli", *Proc. Natl. Acad. Sci. USA* 85: 5879-5883 (1988)); and (8) VHH, which relates to variable antigen-binding domains of heavy chain antibodies from Camelidae (camel, dromedary, llama, alpaca, etc.) (see Nguyen V. K. et al., 2000, *The EMBO Journal,* 19, 921-930; Muyldermans S., 2001, *J Biotechnol.,* 74, 277-302 and a review of Vanl and schoot P. et al., 2011, *Antiviral Research* 92, 389-407). VHH may also be referred to as nanobody (Nb) and/or single-domain antibody. These antibody fragments are obtained using conventional techniques known to those skilled in the art, and assessed for the function in the same manner as for intact antibodies. An antigen-binding fragment targeting IL13Rα2 is also described in International Patent Application Publications WO2014072888A1 and WO2021041725A1, each of which is incorporated herein by reference in its entirety.

In the present application, the term "single-domain antibody" or "VHH" generally refers to a class of antibodies that lack an antibody light chain and have only a heavy chain variable region. In certain cases, the single-domain antibody may be derived from Bactrian camels, dromedaries, alpacas, llamas, nurse sharks, smooth dogfishes or rays (see, e.g., Kang Xiaozhen et al., *Chinese Journal of Biotechnology,* 2018, 34(12): 1974-1984). For example, the single-domain antibody may be derived from alpacas. The single-domain antibody may consist of a heavy chain variable region (VH). The term "heavy chain variable region" generally refers to the amino-terminal domain of the heavy chain of an antigen-binding fragment. The heavy chain variable region may be further divided into hypervariable regions termed complementarity-determining regions (CDRs), which are scattered over more conserved regions termed framework regions (FRs). Each heavy chain variable region may consist of three CDRs and four FRs arranged from the amino-terminus to the carboxyl-terminus in the following order: FR1, CDR1, FR2, CDR2, FR3, CDR3, and FR4. The heavy chain variable region comprises a binding domain that interacts with an antigen.

In the present application, the term "complementarity-determining region" (CDR) generally refers to a complementarity-determining region within a variable region of an antigen-binding fragment. In the present application, there are 3 CDRs present in the heavy chain variable region, and the CDRs are designated HCDR1, HCDR2 and HCDR3 for each variable region. The exact boundaries of those CDRs have been defined differently according to different systems. The system described by Kabat (Kabat et al., Sequences of Proteins of Immunological Interest, National Institutes of Health, Bethesda, Md. (1987) and (1991)) provides not only a clear residue numbering system applicable to any variable region of an antigen-binding fragment, but also precise residue boundaries defining 3 CDRs. Those CDRs may be referred to as Kabat CDRs. Chothia and colleagues (Chothia and Lesk, *J. Mol. Biol.*, 196: 901-917 (1987) and Chothia et al., *Nature* 342: 877-883(1989)) found that although there is large diversity at the amino acid sequence level, certain sub-portions within Kabat CDRs take almost identical peptide backbone conformations. Those sub-portions were designated L1, L2 and L3 or H1, H2 and H3, wherein "L" and "H" refer to the light and heavy chain regions, respectively. Those regions may be referred to as Chothia CDRs, which have boundaries that overlap with Kabat CDRs. Other boundaries defining CDRs that overlap with Kabat CDRs have been described by Padlan (*FASEB J.* 9: 133-139 (1995)) and MacCallum (*J Mol Biol* 262 (5): 732-45 (1996)). In addition, other CDR boundary definitions may not strictly follow one of the above systems, but will nevertheless overlap with Kabat CDRs, although they may be shortened or lengthened according to predictions or experimental findings that a particular residue or a particular group of residues, or even the entire CDRs, do not significantly affect the antigen binding. In the present application, the IMGT numbering scheme is used.

In the present application, the term "FR" generally refers to the more highly conserved portions of antibody variable domains, which are referred to as framework regions. For example, the variable domains of natural heavy and light chains may each comprise four FR regions, namely four in VH (H-FR1, H-FR2, H-FR3, and H-FR4), and four in VL (L-FR1, L-FR2, L-FR3, and L-FR4). A "framework region" generally refers to a portion of the antibody variable region recognized in the art that is present between the more divergent (i.e., hypervariable) CDRs. Such framework regions are typically referred to as frameworks 1 to 4 (FR1, FR2, FR3, and FR4) and provide a backbone for presenting six CDRs (three from the heavy chain and three from the light chain) in the three-dimensional space to form an antigen-binding surface.

In the present application, the term "homology" may generally be equivalent to sequence "identity". A homologous sequence may include an amino acid sequence that may be at least 80%, 85%, 90%, 99.1%, 99.2%, 99.3%, 99.4%, 99.5%, 99.6%, 99.7%, 99.8%, or 99.9% identical to a subject sequence. Generally, the homolog will comprise the same active site, etc. as the subject amino acid sequence. Homology may be considered in terms of similarity (i.e., amino acid residues having similar chemical properties/functions), or may be expressed in terms of sequence identity. In the present application, reference to a sequence having a percent identity of any one of the SEQ ID NOs of an amino acid sequence or a nucleotide sequence refers to a sequence having the percent identity over the entire length of the referenced SEQ ID NO. To determine sequence identity, sequence alignments can be performed by various means known to those skilled in the art, e.g., using BLAST, BLAST-2, ALIGN, NEEDLE, or Megalign (DNASTAR) software, etc. Those skilled in the art can determine appropriate parameters for alignment, including any algorithms required to achieve optimal alignment over the full length of the sequences being compared.

In the present application, the term "specific binding" when referring to the interaction of a binding molecule (e.g., an antibody) with its binding partner (e.g., an antigen) generally means that the interaction is dependent on the presence of a specific structure (e.g., an antigenic determinant or epitope) on the binding partner. In other words, the antibody will preferentially bind to or recognize a binding partner even when the binding partner is present in a mixture of other molecules or organisms. The binding may be mediated by covalent or non-covalent interactions or a combination of both. In other words, the term "specific binding" generally refers to immunospecific binding to an antigenic determinant or epitope and non-immunospecific binding to other antigenic determinants or epitopes. A binding molecule that immunospecifically binds to an antigen may bind to other peptides or polypeptides with relatively low affinity as determined by, for example, radioimmunoassay (RIA), enzyme-linked immunosorbent assay (ELISA), BIACORE, or other assays known in the art. The binding molecule or the fragment thereof that immunospecifically binds to an antigen may cross-react with a related antigen with the same epitope. In some cases, the binding molecule or the fragment thereof that immunospecifically binds to an antigen does not cross-react with other antigens.

In the present application, the term "KD" is used interchangeably with "KD" and generally refers to a dissociation equilibrium constant, in M (mol/L), of a particular antibody-antigen interaction. KD may be calculated from the concentration of substance AB and the concentration of substance A and substance B resulting from its dissociation: $KD=c(A) \times c(B)/c(AB)$. It can be seen from this equation that a larger KD indicates more dissociation and weaker affinity between substances A and B; conversely, a smaller KD indicates less dissociation and stronger affinity between substances A and B.

In the present application, the term "isolated nucleic acid molecule" generally refers to an isolated form of nucleotides, deoxyribonucleotides or ribonucleotides or analogs thereof of any length, isolated from their natural environment, or artificially synthesized.

In the present application, the term "vector" generally refers to a nucleic acid molecule capable of self-replicating in a suitable host, which transfers an inserted nucleic acid molecule into a host cell and/or between host cells. The vector may include vectors primarily for the insertion of DNA or RNA into a cell, vectors primarily for the replication of DNA or RNA, and vectors primarily for the expression of transcription and/or translation of DNA or RNA. The vector also includes vectors having a variety of the above-described functions. The vector may be a polynucleotide capable of being transcribed and translated into a polypeptide when introduced into a suitable host cell. Generally, the vector can produce the desired expression product by culturing an appropriate host cell containing the vector.

In the present application, the term "viral vector" is used broadly to refer to a nucleic acid molecule (e.g., transfer plasmid) or viral particle that mediates the transfer of nucleic acids. The nucleic acid molecule includes virus-derived nucleic acid elements that generally facilitate the transfer or integration of the nucleic acid molecules into the genome of a cell. The viral particle generally includes various viral components and sometimes further includes host cell components in addition to nucleic acids. The viral vector may refer to a virus or viral particle capable of transferring nucleic acids into a cell, or the transferred nucleic acid itself.

In the present application, the term "lentivirus" generally refers to a group (or genus) of complex retroviruses. Exemplary lentiviruses include, but are not limited to: human immunodeficiency virus (HIV; including HIV type 1 and HIV type 2); visna-maedivirus (VMV); caprine arthritis-encephalitis virus (CAEV); equine infectious anemia virus (EIAV); feline immunodeficiency virus (FIV); bovine immunodeficiency virus (BIV); and simian immunodeficiency virus (SIV). In one embodiment, an HIV-based vector backbone (i.e., HIV cis-acting sequence element) is preferred. In particular embodiments, the lentivirus is used to deliver a polynucleotide comprising the CAR to a cell.

In the present application, the term "host cell" or "cell" generally refers to an individual cell, cell line, or cell culture that may contain or has contained a vector comprising the isolated nucleic acid molecule described in the present application, or that is capable of expressing the isolated antigen-binding fragment described in the present application. The host cell may comprise progeny of a single host cell. Due to natural, accidental or deliberate mutations, progeny cells may not necessarily be identical in morphology or in genome to the original parent cell, but are capable of expressing the isolated antigen-binding fragment described herein. The host cell may be obtained by transfecting cells with the vector described herein in vitro. The host cell may be a prokaryotic cell (e.g., *E. coli*) or a eukaryotic cell (e.g., a yeast cell, a COS cell, a Chinese hamster ovary (CHO) cell, a HeLa cell, an HEK293 cell, a COS-1 cell, an NS0 cell, or a myeloma cell). For example, the host cell may be an *E. coli* cell. For example, the host cell may be a yeast cell. For example, the host cell may be a mammalian cell. For example, the mammalian cell may be a CHO-K1 cell.

In the present application, the term "T cell" or "T lymphocyte" may be any T cell, such as a cultured T cell, e.g., a primary T cell, or a T cell from the cultured T cell line, or a T cell obtained from a mammal (preferably a primate, species including monkey, dog, or human). If obtained from a mammal, the T cells may be obtained from a number of sources including, but not limited to, blood, bone marrow, lymph nodes, thymus, or other tissues or fluids. The T cell may also be enriched or purified. The T cell may be obtained by maturing a hematopoietic stem cell into a T cell in vitro or in vivo. In exemplary aspects, the T cell is a human T cell. In exemplary aspects, the T cell is a T cell isolated from a human. The T cell may be any type of T cell, including NKT cells, and may have any developmental stage, including but not limited to CD4+/CD8+ double positive T cells; CDA+ helper T cells; e.g., Th1 and Th2 cells, $CD8^+$ T cells (e.g., cytotoxic T cells); peripheral blood mononuclear cells (PBMCs); peripheral blood leukocytes (PBLs); tumor infiltrating cells (TILs); memory T cells; untreated T cells, and the like. Preferably, the T cell is a $CD8^+$ T cell or a $CD4^+$ T cell. In some alternatives, the T cell is allogeneic (from different donors of the same species) to the recipient subject that receives the cell or cell to be received (e.g., the cells are in the form of a therapeutic composition); in some alternatives, the T cell is autologous (the donor and recipient are the same); in some alternatives, the T cell is syngeneic (the donor and recipient are different, but are homozygotic twins).

In the present application, the term "immune effector cell" generally refers to an immune cell involved in an immune response and performing an effector function. For example, the performing an effector function may include clearing foreign antigens, promoting an immune effector response, or the like. The immune effector cell may include plasma cells, T cells, B cells, natural killer (NK) cells, natural killer T (NKT) cells, mast cells, and myeloid-derived phagocytes.

The immune effector cell of the present application may be autologous/autogeneic ("self") or non-autologous ("non-self", e.g., allogeneic, syngeneic, or xenogeneic). In the present application, the term "autologous" generally refers to cells from the same subject. "Allogeneic" generally means that cells are of the same species as but genetically different from the cells to which they are compared. "Syngeneic" generally means that cells are from different subjects but genetically identical to the cells to which they are compared. "Xenogeneic" generally means that cells are of different species from the cell to which they are compared. In some embodiments, the cells of the present application are autologous or allogeneic.

In the present application, the term "modification" generally refers to changing the state or structure of the cell and/or a change in the state or structure of the cell. The change is generally compared to the state or structure of the corresponding unmodified cell. The change may include a change in endogenous gene expression level or function, for example, a down-regulation, up-regulation, or non-expression of the endogenous gene expression level of the cell by genetic engineering means, which may include homologous recombination, CRISPR/Cas9 system gene editing, or the like; the change may also include a change in cellular protein expression, structure, or function, for example, a change in the expression, structure, or function of the corresponding protein achieved by the change in the expression level or function of the endogenous gene, such as a change in the expression, structure or function of a protein achieved by the regulation of protein translation and post-translational modification; the change may also include the introduction of foreign genes, the expression of foreign proteins, and the like.

In the present application, the term "TRAC" generally refers to a T cell receptor a chain constant region (T cell receptor alpha constant). A T cell receptor (TCR) generally refers to a specific receptor located on the surface of the T cell, which is capable of recognizing antigens that bind to major histocompatibility complex (MHC) molecules. TCRs are generally composed of two different protein chains (i.e., heterodimers). In humans, TCRs in most T cells are composed of one a chain and one β chain (encoded by TRA and TRB, respectively), and this class of T cells is referred to as αβ T cells; and in a few T cells, TCRs are composed of γ chain and δ chain (encoded by TRG and TRD, respectively), and this class of T cells is referred to as γδ T cells. Generally, αβ T cells account for about 95% of the total T cells, γδ T cells account for about 5% of the total T cells, and the ratios vary during ontogenesis and in diseased states (e.g., leukemia), and also differ among species. Each chain constituting TCRs comprises a variable region and a constant region. In humans, the gene encoding α chain (TRA, e.g., information as shown by HGNC:12027) is located on chromosome 14 and consists of multiple gene fragments, including a variable fragment (V), a joining fragment (J), and a constant fragment (C). The TRAC gene generally refers to a gene sequence encoding the T cell receptor α chain constant region (C) (e.g., information as shown by HGNC:12029) and is located on chromosome 14 (14q11.2; 14:22,547,505-22,552,131). Generally, one of the genes of the variable fragments (V) encoding the N-fragment of the antigen recognition domain is rearranged with one of the joining fragments (J) to produce a functional V-region exon, which is transcribed and linked to the constant region (C) by splicing, thereby forming a coding sequence of the T cell receptor α chain.

In the present application, the term "major histocompatibility complex antigen" ("MHC", also referred to as "human leukocyte antigen" ("HLA") in humans) generally refers to a protein expressed on the surface of a cell that confers a unique antigenic identity to the cell. MHC/HLA antigens are target molecules that are recognized by T cells and NK cells as being derived from the same source of hematopoietic stem cells as immune effector cells ("self") or as being derived from another source of hematopoietic repopulating cells ("non-self"). Two major classes of HLA antigens are recognized: HLA class I and HLA class II. HLA class I antigens (A, B, and C in humans) allow each cell to be recognized as "self", while HLA class II antigens (DR, DP, and DQ in humans) are involved in reactions between lymphocytes and antigen-presenting cells. Both have been implicated in the rejection of transplanted organs. An important aspect of the HLA gene system is its polymorphism. Each gene for MHC class I (A, B, and C) and MHC class II (DP, DQ, and DR) exists in different alleles. HLA alleles are designated by numbers and subscripts. For example, two unrelated individuals may carry class I HLA-B genes B5 and Bw41, respectively. Allelic products differ in one or more amino acids of the α and/or β domains. A number of specific antibodies or nucleic acid reagents are used to type HLA haplotypes of individuals using leukocytes that express class I and class II molecules. Genes commonly used for HLA typing are six MHC class I and II proteins, i.e., two alleles for each of HLA-A, HLA-B, and HLA-DR. The HLA genes are clustered in a "super locus" present on chromosome position 6p21, wherein the "super locus" encodes 6 classical transplantation HLA genes and at least 132 protein-coding genes that play important roles in the regulation of the immune system as well as some other fundamental molecular and cellular processes. The complete locus measures roughly 3.6 Mb with at least 224 loci. One effect of such clustering is that a "haplotype", i.e., a group of alleles present on a single chromosome, is inherited from one parent and tends to be inherited as a group. The group of alleles inherited from each parent form a haplotype, in which some alleles tend to be associated together. Identifying haplotypes of a patient may help predict the probability of finding a matching donor and help formulate a search strategy, because some alleles and haplotypes are more common than others and they are distributed at different frequencies in different racial and ethnic groups.

In the present application, "HLA-A" generally refers to a class of human leukocyte antigen polypeptide chains encoded by an HLA-A gene located on human chromosome 6p21.3 (e.g., information as shown by HGNC:4931). HLA-A is one of the three major polypeptide types that constitute MHC class I molecules on the surface of human cells, and others further include HLA-B and HLA-C. A heterodimer composed of an α chain encoded by the HLA-A gene and a β chain encoded by a B2M gene (β2-microglobulin) is an HLA-A class MHC I molecule. The α chain encoded by the HLA-A gene may comprise an α1 domain, an α2 domain, an α3 domain, a transmembrane region, and a cytoplasmic region, wherein the α1 domain and the α2 domain may bind to a peptide fragment so as to present the peptide fragment to an immune cell by the MHC I molecule (e.g., HLA-A class). In humans, similar to most mammals, the α chain of the MHC I molecule is polymorphic, and there are many variations in the primary structure thereof. As of December 2013, there are 2432 known HLA-A alleles in total, which encode 1740 active proteins and 117 inactive proteins. In the present application, HLA-A alleles may include sequence information on different HLA-A alleles recorded in the IMGT/HLA database version 3.38.0 (https://www.ebi.ac.uk/ipd/imgt/hla/) and designated by the WHO HLA Factor Nomenclature Committee.

In the present application, the term "HLA-B" generally refers to a part of the gene family of human leukocyte antigen (HLA) complexes. HLA is a human version of the major histocompatibility complex (MHC), and MHC is a gene family present in many species. The complex genes are divided into three basic groups: class I, class II, and class III. In humans, the HLA-B gene and the two related genes HLA-A and HLA-C are the major genes of MHC class I. The HLA-B gene is located in the cell band 21.3 of the short (p) arm of chromosome 6 from base pairs 31,353,871 to 31,357,211. HLA-B is one of the three major HLAs that should be matched between the donor and recipient. They are HLA-A, HLA-B (both are MHC class I), and HLA-DR (MHC class II). If two tissues have the same genes encoding the three HLAs, the possibility and severity of rejection are minimized. Hundreds of versions (alleles) of HLA-B are known, each version having a specific number (e.g., HLA-B27). Closely related alleles are grouped together, for example, at least 28 very similar alleles are subtypes of HLA-B27. These subtypes are designated as HLA-B*2701 to HLA-B*2728.

In the present application, the term "HLA-matched" refers to a donor-recipient pair in which none of the HLA antigens are mismatched between the donor and recipient, such as a donor providing a hematopoietic stem cell graft to a recipient in need of hematopoietic stem cell transplantation therapy. HLA-matched (i.e., in which all 6 alleles are matched) donor-recipient pairs have a reduced risk of graft rejection, because endogenous T cells and NK cells are less likely to recognize the incoming graft as foreign, and are thus less likely to generate an immune response against the graft.

In the present application, the term "HLA-mismatched" refers to a donor-recipient pair in which at least one HLA antigen (particularly with respect to HLA-A, HLA-B, and HLA-DR) is mismatched between the donor and recipient, such as a donor providing a hematopoietic stem cell graft to a recipient in need of hematopoietic stem cell transplantation therapy. In some embodiments, one haplotype is matched, and the other is mismatched. HLA-mismatched donor-recipient pairs may have an increased risk of graft rejection relative to HLA-matched donor-recipient pairs, because endogenous T cells and NK cells are more likely to recognize the incoming graft as foreign in the case of HLA-mismatched donor-recipient pairs, and such T cells and NK cells are thus more likely to generate an immune response against the graft.

In the present application, the term "B2M" generally refers to β2-microglobulin, which is one of the components of MHC class I molecules. β2 microglobulin (also referred to as β chain) may form an MHC class I molecule with an α chain encoded by HLA. B2M is generally expressed in all nucleated cells. In humans, β2 microglobulin is encoded by the B2M gene located at 15q21.1 (e.g., information as shown by HGNC:914).

In the present application, the term "CIITA" generally refers to a transactivator of a class II major histocompatibility complex (MHC II). The transactivator may be a protein having an acidic transcriptional activation domain, 4 LRRs (leucine-rich repeats), and a GTP binding domain. The protein may be located in the cell nucleus, act as a positive regulator of the gene transcription of the class II major histocompatibility complex (MHC II), and be referred to as a "master control factor" for the expression of these genes. The protein may also bind to GTP and utilize the binding to GTP to transport itself into the cell nucleus, where it generally functions by acetyltransferase (AT) activity in a coactivator-like manner. In humans, the protein is encoded by a gene located at 16p13.13 (e.g., information as shown by HGNC:7067), and several transcript variants encoding different isoforms can be produced.

In the present application, the term "wild-type cell" generally refers to a cell that naturally occurs or is of natural origin.

In the present application, the term "nucleic acid" or "polynucleotide" or "nucleic acid molecule" generally refers to deoxyribonucleic acid (DNA) or ribonucleic acid (RNA) and polymers thereof in either single-stranded or double-stranded form. Unless specifically limited, the term may include nucleic acids comprising analogs of natural nucleotides that have similar binding properties as the reference nucleic acid (e.g., with sequence information shown) and are metabolized in a manner similar to naturally occurring nucleotides. Unless otherwise indicated, the sequence of a nucleic acid may include conservatively modified variants thereof (e.g., degenerate codon substitutions), alleles, orthologs, SNPs, and complementary sequences, as well as the sequences explicitly indicated.

In the present application, the term "expression" generally refers to the transcription and/or translation of a particular nucleotide sequence.

In the present application, the term "gene mutation" generally refers to a change in the composition or arrangement order of base pairs occurring in the structure of genes, such as a point mutation caused by a single base change, or deletion, duplication, insertion, and the like of a plurality of bases.

In the present application, the term "gene silencing" generally refers to the prevention of the expression of certain genes by regulatory mechanisms. The gene silencing may primarily include two types: one is transcriptional gene silencing (TGS) caused by factors such as DNA methylation, heterochromatization, and position effect at the transcriptional level, and the other is post-transcriptional gene silencing (PTGS), which is the effect on gene expression at the post-transcriptional level by specific intervention on the target RNA. Generally, when a gene is silenced, the expression of the corresponding gene is down-regulated/reduced. When a gene is knocked out, it is generally not expressed. For example, the expression of a specific gene in a cell disappears when all alleles of the specific gene are knocked out. Gene silencing is generally considered to be a gene knockdown mechanism, and methods commonly used to silence genes may be, for example, RNAi and the like.

In the present application, the term "endogenous" refers to any substance derived from or produced within an organism, a cell, a tissue, or a system.

In the present application, the term "exogenous" refers to any substance introduced from or produced outside of an organism, a cell, a tissue, or a system.

In the present application, the term "antisense RNA" generally refers to a single-stranded RNA complementary to a transcript mRNA (messenger RNA). The antisense RNA may inhibit the expression of genes by binding to mRNA. For example, the binding of the antisense RNA to the target mRNA results in an increased sensitivity of the double-stranded RNA molecule to RNA enzyme III, and causes the degradation of the double-stranded RNA molecule. For example, the antisense RNA binds to an upstream non-coding region of mRNA, thereby directly inhibiting the translation of the target mRNA.

In the present application, the term "siRNA" generally refers to the abbreviation of small interfering RNA or short interfering RNA. siRNA is a class of double-stranded, non-coding RNA molecules that are about 18-28 base pairs in length and may cause the degradation of mRNA by the complementary binding to mRNA, thereby interfering with the expression of a specific gene. In certain embodiments, siRNA may be a product obtained by treating a long double-stranded RNA or shRNA with Dicer enzyme. In certain embodiments, siRNA enters a cell to form an RNA-induced silencing complex (RISC) with other proteins, the sense strand is degraded, and the antisense strand may bind to a complementary targeting sequence, thereby achieving gene silencing.

In the present application, the term "shRNA" generally refers to the abbreviation of short hairpin RNA, i.e., "short hairpin RNA". shRNA generally comprises two short inverted repeats separated by a stem-loop sequence to form a hairpin structure. Generally, shRNA may further comprise 5-6 T bases as transcription terminators for RNA polymerase III. In certain embodiments, shRNA may enter a cell via a viral vector or plasmid, and be transcribed under the action of polymerase II or polymerase III. The transcripts are exported from the cell nucleus (generally via Exportin 5), and then transported to RISC after Dicer treatment. The sense strand is degraded, and the antisense strand may bind to a complementary targeting sequence, thereby achieving gene silencing.

In the present application, the term "CRISPR/Cas system" generally refers to a group of molecules comprising an RNA-guided nuclease or other effector molecules and a gRNA molecule, and the molecules are capable of directing and realizing modification of a nucleic acid by the RNA-guided nuclease or other effector molecules at a target sequence, e.g., causing degradation of the target sequence. In certain embodiments, the CRISPR system comprises gRNA and a Cas protein, e.g., Cas9 protein. A system comprising Cas9 or a functional mutant thereof is referred to herein as "Cas9 system" or "CRISPR/Cas9 system". In certain embodiments, the gRNA molecule and Cas molecule may be complexed to form a ribonucleoprotein (RNP) complex.

In the present application, the terms "gRNA molecule", "guide RNA", "instruction RNA", "direct RNA", "guide RNA molecule", and "gRNA" can be used interchangeably and generally refer to a nucleic acid molecule capable of facilitating the specific guidance of the RNA-guided nuclease or other effector molecules (generally complexed with a gRNA molecule) onto the target sequence. In certain embodiments, the guidance is achieved by the hybridization of a portion of gRNA with DNA (e.g., via a gRNA guide domain) and by the binding of a portion of the gRNA molecule to the RNA-guided nuclease or other effector molecules (e.g., at least via gRNAtracr). In certain embodiments, the gRNA molecule consists of a single, contiguous polynucleotide molecule, referred to herein as a "single guide RNA", "sgRNA", or the like. In other embodiments, the gRNA molecule consists of multiple (e.g., two) polynucleotide molecules that are themselves capable of association (typically by hybridization), referred to herein as a "dual guide RNA", "dgRNA", or the like.

In the present application, the term "Cas protein" generally refers to an enzyme responsible for cleaving DNA in the CRISPR/Cas system. The enzyme may include enzymes from types I, II, and III CRISPR/Cas systems, e.g., Cas3, Cas9, and Cas10.

In the present application, the term "Cas9 protein" generally refers to an enzyme responsible for cleaving DNA, which is from the bacterial type II CRISPR/Cas system. Cas9 may include wild-type proteins and functional mutants thereof.

In the present application, "allele" generally refers to a form of a gene sequence at a locus that may have different variations. The locus is also referred to as a gene site or site and refers to a fixed position on a chromosome, e.g., where a gene is located. The arrangement of a locus in the genome is referred to as a genetic map.

In the present application, the term "homozygote" generally refers to a genotype individual in which two alleles of homologous chromosomes are identical at the same locus. A pair of opposing genes may have individuals with two genotypes, AA and aa.

In the present application, the term "heterozygote" generally refers to a genotype individual in which two alleles at the same site on homologous chromosomes in a diploid are not identical, such as Aa. Heterozygous genotypes are generally more adaptive than homozygous dominant or homozygous recessive genotypes, and such phenomenon is referred to as heterozygote advantage.

In the present application, the terms "tumor" and "cancer" are used interchangeably and generally refer to a disease characterized by rapid and uncontrolled growth of abnormal cells. Cancer cells can spread to other parts of the body locally or through the bloodstream and lymphatic system. Examples of various cancers are described herein and include, but are not limited to, breast cancer, prostate cancer, ovarian cancer, cervical cancer, skin cancer, pancreatic cancer, colorectal cancer, kidney cancer, liver cancer, brain cancer, lymphoma, leukemia, lung cancer, and the like. The term "cancer" or "tumor" includes premalignant and malignant cancers and tumors, and also encompasses solid tumors and non-solid tumors.

In the present application, the term "pharmaceutically acceptable" generally refers to those compounds, materials, compositions, and/or dosage forms which are, commensurate with a reasonable benefit/risk ratio, and suitable, within the scope of sound medical judgment, for use in contact with the tissues of human beings and animals without excessive toxicity, irritation, allergic response, or other problems or complications.

In the present application, the term "pharmaceutically acceptable carrier" generally refers to any of those carriers conventionally used and is limited only by physical or chemical factors (such as solubility and lack of reactivity with active binding agents) and by the route of administration. The pharmaceutically acceptable carrier, such as a vehicle, an adjuvant, an excipient, and a diluent, described herein is well known to those skilled in the art and readily available to the public. In one aspect, the pharmaceutically acceptable carrier is one that is chemically inert to an active ingredient of a pharmaceutical composition and one that does not have adverse side effects or toxicity under the conditions of use. In some embodiments, the carrier does not produce an adverse, allergic, or other untoward reaction when administered to an animal or human. In some aspects, the pharmaceutical composition does not comprise pyrogens and other impurities that may be harmful to humans or animals. The pharmaceutically acceptable carrier includes any and all solvents, dispersion media, coatings, antibacterial and antifungal agents, isotonic and absorption delaying agents, and the like; the use of the pharmaceutically acceptable carrier is well known in the art.

The acceptable carriers, excipients, or stabilizers are non-toxic to recipients and are preferably inert at the doses and concentrations employed, and include buffers, such as phosphate, citrate, or other organic acids; antioxidants, such as ascorbic acid; low molecular weight polypeptides; proteins, such as serum albumin, gelatin, or immunoglobulin; hydrophilic polymers, such as polyvinylpyrrolidone; amino acids, such as glycine, glutamine, asparagine, arginine, or lysine; monosaccharides, disaccharides, and other carbohydrates including glucose, mannose, or dextrin; chelating agents, such as EDTA; sugar alcohols, such as mannitol or sorbitol; salt-forming counter-ions, such as sodium; and/or non-ionic surfactants, such as Tween, Pluronics, or polyethylene glycol (PEG).

In the present application, the term "effective amount" or "effective dose" generally refers to an amount sufficient to achieve, or at least partially achieve, a desired effect. "Therapeutically effective amount" or "therapeutically effective dose" of a drug or therapeutic agent is generally any amount of drug that promotes the regression of a disease (as evidenced by a decrease in the severity of symptoms of the disease, an increase in the frequency and duration of the asymptomatic phase of the disease, or the prevention of damage or disability due to the development of the disease) when used alone or in combination with another therapeutic agent.

"Therapeutically effective amount" or "effective amount" of an anti-B7H3 CAR-T cell is also an amount or dose that has a therapeutically beneficial effect over any toxic or deleterious effects, such as CRS, of the anti-B7H3 CAR-T cell. The term "therapeutically effective amount" includes an amount effective to "treat" a subject (e.g., a patient). In one embodiment, the therapeutically effective dose is the minimum effective dose (MED) of the anti-B7H3 CAR-T cell for treating multiple myeloma in the subject. In one embodiment, the therapeutically effective dose is the maximum tolerated dose (MTD) of the anti-B7H3 CAR-T cell that does not cause the subject to have unresolved CRS.

In the present application, the term "comprise" or "comprising" generally means including, summarizing, containing or encompassing. In certain cases, the term also means "being" or "consisting of . . . ".

In the present application, the term "about" generally means varying by 0.5%-10% above or below the stated value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the stated value.

In the present application, the term "subject" generally refers to a human or non-human animal, including but not limited to cats, dogs, horses, pigs, cows, sheep, rabbits, mice, rats, monkeys, and the like.

DETAILED DESCRIPTION OF THE INVENTION

Antigen-Binding Polypeptide

In one aspect, the present application provides an antigen-binding polypeptide comprising at least one complementarity-determining region (CDR) of an antibody heavy chain variable region (VH), wherein the VH comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 25.

In certain embodiments, the VH comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 26, SEQ ID NO: 27, SEQ ID NO: 28, or SEQ ID NO: 29.

In certain embodiments, the antigen-binding polypeptide comprises a VH, wherein the VH comprises a heavy chain complementarity-determining region 1 (HCDR1), a heavy chain complementarity-determining region 2 (HCDR2), and a heavy chain complementarity-determining region 3

(HCDR3), and the HCDR3 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 7. For example, the HCDR3 may comprise an amino acid sequence set forth in SEQ ID NO: 7.

In certain embodiments, the HCDR3 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 8 or SEQ ID NO: 9. For example, the HCDR3 may comprise an amino acid sequence set forth in SEQ ID NO: 8 or SEQ ID NO: 9.

In certain embodiments, the HCDR2 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 4. For example, the HCDR2 may comprise an amino acid sequence set forth in SEQ ID NO: 4.

In certain embodiments, the HCDR2 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 5 or SEQ ID NO: 6. For example, the HCDR2 may comprise an amino acid sequence set forth in SEQ ID NO: 5 or SEQ ID NO: 6.

In certain embodiments, the HCDRI comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 1. For example, the HCDR1 may comprise an amino acid sequence set forth in SEQ ID NO: 1.

In certain embodiments, the HCDR1 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 2 or SEQ ID NO: 3. For example, the HCDR1 may comprise an amino acid sequence set forth in SEQ ID NO: 2 or SEQ ID NO: 3.

In certain embodiments, the VH comprises: HCDR1 comprising an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 1, HCDR2 comprising an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 4, and HCDR3 comprising an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 7.

For example, the VH may comprise: the HCDR1 comprising the amino acid sequence set forth in SEQ ID NO: 1, the HCDR2 comprising the amino acid sequence set forth in SEQ ID NO: 4, and the HCDR3 comprising the amino acid sequence set forth in SEQ ID NO: 7.

In certain embodiments, the VH comprises:
i) the HCDR1 comprising the amino acid sequence set forth in SEQ ID NO: 2, the HCDR2 comprising the amino acid sequence set forth in SEQ ID NO: 5, and the HCDR3 comprising the amino acid sequence set forth in SEQ ID NO: 8; or
ii) the HCDR1 comprising the amino acid sequence set forth in SEQ ID NO: 3, the HCDR2 comprising the amino acid sequence set forth in SEQ ID NO: 6, and the HCDR3 comprising the amino acid sequence set forth in SEQ ID NO: 9.

In certain embodiments, the VH comprises a heavy chain framework region 1 (HFR1), a heavy chain framework region 2 (HFR2), a heavy chain framework region 3 (HFR3), and a heavy chain framework region 4 (HFR4), wherein the HFR1 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 10. For example, the HFR1 may comprise an amino acid sequence set forth in SEQ ID NO: 10.

In certain embodiments, the HFR1 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 11, SEQ ID NO: 12, SEQ ID NO: 13, or SEQ ID NO: 14. For example, the HFRI comprises an amino acid sequence set forth in SEQ ID NO: 11, SEQ ID NO: 12, SEQ ID NO: 13, or SEQ ID NO: 14.

In certain embodiments, the HFR2 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 15. For example, the HFR2 may comprise an amino acid sequence set forth in SEQ ID NO: 15.

In certain embodiments, the HFR2 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 16 or SEQ ID NO: 17. For example, the HFR2 may comprise an amino acid sequence set forth in SEQ ID NO: 16 or SEQ ID NO: 17.

In certain embodiments, the HFR3 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 18. For example, the HFR3 may comprise an amino acid sequence set forth in SEQ ID NO: 18.

In certain embodiments, the HFR3 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 19, SEQ ID NO: 20, or SEQ ID NO: 21. For example, the HFR3 may comprise an amino acid sequence set forth in SEQ ID NO: 19, SEQ ID NO: 20, or SEQ ID NO: 21.

In certain embodiments, the HFR4 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 22. For example, the HFR4 may comprise an amino acid sequence set forth in SEQ ID NO: 22.

In certain embodiments, the HFR4 comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 23 or SEQ ID NO: 24. For example, the HFR4 may comprise an amino acid sequence set forth in SEQ ID NO: 23 or SEQ ID NO: 24.

In certain embodiments, the VH comprises HFR1, HFR2, HFR3, and HFR4, and the HFR1, HFR2, HFR3, and HFR4 are selected from:
  i) the HFR1 comprising the amino acid sequence set forth in SEQ ID NO: 11, the HFR2 comprising the amino acid sequence set forth in SEQ ID NO: 16, the HFR3 comprising the amino acid sequence set forth in SEQ ID NO: 19, and the HFR4 comprising the amino acid sequence set forth in SEQ ID NO: 23;
  ii) the HFR1 comprising the amino acid sequence set forth in SEQ ID NO: 12, the HFR2 comprising the amino acid sequence set forth in SEQ ID NO: 16, the HFR3 comprising the amino acid sequence set forth in SEQ ID NO: 20, and the HFR4 comprising the amino acid sequence set forth in SEQ ID NO: 24;
  iii) the HFR1 comprising the amino acid sequence set forth in SEQ ID NO: 13, the HFR2 comprising the amino acid sequence set forth in SEQ ID NO: 17, the HFR3 comprising the amino acid sequence set forth in SEQ ID NO: 21, and the HFR4 comprising the amino acid sequence set forth in SEQ ID NO: 23; and
  vi) the HFR1 comprising the amino acid sequence set forth in SEQ ID NO: 14, the HFR2 comprising the amino acid sequence set forth in SEQ ID NO: 17, the HFR3 comprising the amino acid sequence set forth in SEQ ID NO: 20, and the HFR4 comprising the amino acid sequence set forth in SEQ ID NO: 24.

In certain embodiments, the VH comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 25. For example, the VH may comprise an amino acid sequence set forth in SEQ ID NO: 25.

In certain embodiments, the VH comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 26, SEQ ID NO: 27, SEQ ID NO: 28, or SEQ ID NO: 29. For example, the VH may comprise an amino acid sequence set forth in SEQ ID NO: 26, SEQ ID NO: 27, SEQ ID NO: 28, or SEQ ID NO: 29.

In certain embodiments, the antigen-binding polypeptide includes an antibody or an antigen-binding fragment thereof.

In certain embodiments, the antibody includes a monoclonal antibody, a polyclonal antibody, a dimer, a polymer, a multispecific antibody, an intact antibody, an antibody fragment, a human antibody, a humanized antibody, or a chimeric antibody.

In certain embodiments, the antigen-binding fragment includes a Fab fragment, an Fv fragment, F(ab')$_2$, a single-chain Fv (scFv), or a single-domain antibody (VHH).

Chimeric Antigen Receptor

In one aspect, the present application provides a chimeric antigen receptor (CAR) targeting B7H3, which comprises a targeting moiety, wherein the targeting moiety comprises the aforementioned antigen-binding polypeptide.

In certain embodiments, the targeting moiety includes a VHH.

For example, the targeting moiety comprises a VHH, wherein the VHH may comprise: HCDR1 comprising an amino acid sequence set forth in SEQ ID NO: 1, HCDR2 comprising an amino acid sequence set forth in SEQ ID NO: 4, and HCDR3 comprising an amino acid sequence set forth in SEQ ID NO: 7.

As another example, the targeting moiety comprises a VHH, wherein the VHH may comprise an amino acid sequence set forth in SEQ ID NO: 25.

In certain embodiments, the chimeric antigen receptor comprises a transmembrane domain, wherein the transmembrane domain comprises a transmembrane domain derived from one or more proteins selected from the group consisting of: CD8A, CD8B, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4 (CD244), FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, and SLAM.

In certain embodiments, the transmembrane domain comprises a transmembrane domain derived from CD8A.

In certain embodiments, the transmembrane domain comprises an amino acid sequence having at least about 90%, about 91%, about 92%, about 93%, about 94%, about 95%, about 96%, about 97%, about 98%, about 99%, or about 99.5% identity to the amino acid sequence set forth in any one of SEQ ID NO: 42 to SEQ ID NO: 90.

In certain embodiments, the chimeric antigen receptor comprises an intracellular co-stimulatory signaling domain, wherein the intracellular co-stimulatory signaling domain comprises an intracellular co-stimulatory signaling domain derived from one or more proteins selected from the group consisting of: CD28, CD137, CD27, CD2, CD7, CD8A, CD8B, OX40, CD226, DR3, SLAM, CDS, ICAM-1, NKG2D, NKG2C, B7H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, and MyD88.

In certain embodiments, the intracellular co-stimulatory signaling domain is derived from a co-stimulatory signaling domain of 4-1BB.

In certain embodiments, the intracellular co-stimulatory signaling domain comprises an amino acid sequence having at least about 90%, about 91%, about 92%, about 93%, about 94%, about 95%, about 96%, about 97%, about 98%, about 99%, or about 99.5% identity to the amino acid sequence set forth in any one of SEQ ID NO: 91 to SEQ ID NO: 123.

In certain embodiments, the chimeric antigen receptor comprises an intracellular signaling domain, wherein the intracellular signaling domain comprises an intracellular signaling domain derived from one or more proteins selected from the group consisting of: CD3ζ, CD3δ, CD3γ, CD3ε, CD79a, CD79b, FceIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

In certain embodiments, the intracellular signaling domain comprises a signaling domain derived from CD3ζ.

In certain embodiments, the intracellular signaling domain comprises an amino acid sequence having at least about 90%, about 91%, about 92%, about 93%, about 94%, about 95%, about 96%, about 97%, about 98%, about 99%, or about 99.5% identity to the amino acid sequence set forth in any one of SEQ ID NO: 107, SEQ ID NO: 111, SEQ ID NO: 112, and SEQ ID NO: 124 to SEQ ID NO: 134.

In certain embodiments, the chimeric antigen receptor comprises a hinge region between the targeting moiety and the transmembrane domain, wherein the hinge region comprises a hinge region derived from one or more proteins selected from the group consisting of: CD28, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, and LIGHT.

In certain embodiments, the hinge region comprises a hinge region derived from CD8A.

In certain embodiments, the hinge region comprises an amino acid sequence having at least about 90%, about 91%, about 92%, about 93%, about 94%, about 95%, about 96%, about 97%, about 98%, about 99%, or about 99.5% identity to the amino acid sequence set forth in any one of SEQ ID NO: 135 to SEQ ID NO: 156.

In certain embodiments, a non-targeting moiety of the chimeric antigen receptor comprises a hinge region, a transmembrane domain, an intracellular co-stimulatory signaling domain, and an intracellular signaling domain.

In certain embodiments, a non-targeting moiety of the chimeric antigen receptor comprises a transmembrane domain of CD8A molecule, a hinge region of CD8A, an intracellular co-stimulatory signaling domain of 4-1BB, and an intracellular signaling domain of CD3ζ.

For example, the chimeric antigen receptor uses an anti-B7H3 single-domain antibody as an extracellular antigen-binding domain linked to an intracellular signaling domain via a hinge region and a transmembrane domain of the CD8A molecule, the intracellular signaling domain consisting of a 4-1BB intracellular co-stimulatory signaling domain and a CD3ζ intracellular signaling domain.

In certain embodiments, the non-targeting moiety of the chimeric antigen receptor comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 30.

In certain embodiments, the chimeric antigen receptor further comprises a signal peptide fragment, wherein the C-terminus of the signal peptide fragment is linked to the N-terminus of the targeting moiety. For example, the chimeric antigen receptor may include a CAR comprising a signal peptide, an anti-B7H3 VHH, a CD8A hinge domain, a CD8A transmembrane domain, a 4-1BB co-stimulatory domain, and a CD3ζ primary signaling domain.

In certain embodiments, the signal peptide fragment includes a CD8A signal peptide fragment.

In certain embodiments, the signal peptide fragment of the chimeric antigen receptor comprises an amino acid sequence having at least about 90%, about 91%, about 92%, about 93%, about 94%, about 95%, about 96%, about 97%, about 98%, about 99%, or about 99.5% identity to the amino acid sequence set forth in SEQ ID NO: 31.

Nucleic Acid Molecule, Vector, and Cell

In another aspect, the present application provides one or more isolated nucleic acid molecules encoding the aforementioned antigen-binding polypeptide or the aforementioned chimeric antigen receptor.

In certain embodiments, the isolated nucleic acid molecule comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 36, SEQ ID NO: 37, SEQ ID NO: 38, and SEQ ID NO: 39.

In another aspect, the present application provides a vector comprising the aforementioned isolated nucleic acid molecule.

In certain embodiments, the vector is an expression vector.

In certain embodiments, the vector is selected from a DNA vector, an RNA vector, a plasmid, a lentiviral vector, an adenoviral vector, an adeno-associated viral vector, and a retroviral vector. For example, the vector may be a lentiviral vector.

In another aspect, the present application provides a cell i) comprising the aforementioned isolated nucleic acid molecule or the aforementioned vector; and/or ii) expressing the aforementioned antigen-binding polypeptide or chimeric antigen receptor.

Immune Effector Cell

In another aspect, the present application provides an immune effector cell comprising the aforementioned nucleic acid molecule or the aforementioned vector, and/or expressing the aforementioned CAR.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell. For example, the immune effector cell may be a T cell. As another example, the immune effector cell may be a human T cell.

In certain embodiments, the immune effector cell includes an autologous or non-autologous immune effector cell.

In certain embodiments, the immune effector cell includes a modified immune effector cell.

In certain embodiments, the modified immune effector cell includes a cell that reduces immune rejection caused by allogeneic cell therapy.

In certain embodiments, the functions of a T cell antigen receptor (TCR) and major histocompatibility complexes (MHCI, MHCII) in the modified immune effector cell are inhibited in a T cell.

In certain embodiments, the modification comprises down-regulation of the expression and/or activity of one or more of immune rejection-related genes.

In certain embodiments, the immune rejection-related gene is selected from one or more of the following groups: TRAC, TRBC, HLA-A, HLA-B, B2M, and CIITA.

In certain embodiments, the immune rejection-related gene is selected from one or more of the following groups: TRAC, TRBC, HLA-A, and HLA-B.

In certain embodiments, the immune rejection-related gene is selected from one or more of the following groups: TRAC, TRBC, and HLA-A.

In certain embodiments, the immune rejection-related gene is selected from one or more of the following groups: TRAC and HLA-A.

In certain embodiments, the expression and/or activity of the TRAC gene and the HLA-A gene in the modified immune effector cell is down-regulated as compared to a corresponding unmodified cell.

In certain embodiments, the expression and/or activity of the CIITA gene in the modified immune effector cell is not down-regulated as compared to the corresponding unmodified cell.

In certain embodiments, the expression and/or activity of the B2M gene in the modified immune effector cell is not down-regulated as compared to the corresponding unmodified cell.

In certain embodiments, the expression and/or activity of the TRAC gene and the HLA-A gene in the modified immune effector cell is down-regulated as compared to a corresponding wild-type cell.

In certain embodiments, the expression and/or activity of the B2M gene in the modified immune effector cell is not down-regulated as compared to the corresponding wild-type cell.

In certain embodiments, the expression and/or activity of the CIITA gene in the modified immune effector cell is not down-regulated as compared to the corresponding wild-type cell.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene knockout, gene mutation, and/or gene silencing.

In certain embodiments, the modification comprises knocking out either of two TRAC alleles and knocking out either of two HLA-A alleles in the immune effector cell.

In certain embodiments, the modification comprises knocking out the two TRAC alleles and knocking out either of the two HLA-A alleles in the immune cell.

In certain embodiments, the modification comprises knocking out an exon of the TRAC gene and knocking out an exon of the HLA-A gene in the immune cell.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification further comprises administering to the immune effector cell sgRNA targeting an exon portion of the TRAC gene.

In certain embodiments, the sgRNA targeting the exon portion of the TRAC gene comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 157 to SEQ ID NO: 171.

In certain embodiments, the modification comprises administering to the immune effector cell sgRNA targeting an exon portion of the HLA-A gene.

In certain embodiments, the sgRNA targeting the exon portion of the HLA-A gene comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 172 to SEQ ID NO: 212.

In certain embodiments, the modification further comprises administering to the cell a Cas enzyme.

In certain embodiments, the Cas enzyme includes a Cas9 protein.

In certain embodiments, the antisense RNA comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 213 to SEQ ID NO: 216.

In certain embodiments, the immune effector cell is an HLA-B homozygous cell.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the immune effector cell is an HLA-A homozygous or heterozygous cell.

In certain embodiments, the HLA-A homozygote or heterozygote includes HLA-A*02 homozygote, HLA-A*11 homozygote, HLA-A*02/A*11 heterozygote, or HLA-A*24 homozygote.

In another aspect, the present application provides a method for preparing an immune effector cell, which comprises introducing the aforementioned nucleic acid molecule or the aforementioned vector into the immune effector cell.

In certain embodiments, the method further comprises: modifying the immune effector cell before/after introducing the aforementioned nucleic acid molecule or the aforementioned vector into the immune effector cell, wherein the modification comprises down-regulation of the expression and/or activity of one or more of immune rejection-related genes.

In certain embodiments, the method comprises: modifying the immune effector cell after introducing the aforementioned nucleic acid molecule or the aforementioned vector into the immune effector cell, wherein the modification comprises down-regulation of the expression and/or activity of one or more of immune rejection-related genes.

For example, the method for preparing an immune effector cell may comprise:
(1) introducing the aforementioned nucleic acid molecule or the aforementioned vector into an immune effector cell; and
(2) modifying the immune effector cell, wherein the modification comprises down-regulation of the expression and/or activity of one or more of immune rejection-related genes.

In certain embodiments, the immune rejection-related gene is selected from one or more of the following groups: TRAC, TRBC, HLA-A, HLA-B, B2M, and CIITA.

In certain embodiments, the expression and/or activity of the TRAC gene and the HLA-A gene in the immune effector cell is down-regulated as compared to the expression and/or activity of a corresponding gene in a corresponding unmodified cell.

In certain embodiments, the expression and/or activity of the CIITA gene is not down-regulated as compared to the expression and/or activity of the corresponding gene in the corresponding unmodified cell.

In certain embodiments, the expression and/or activity of the B2M gene is not down-regulated as compared to the expression and/or activity of the corresponding gene in the corresponding unmodified cell.

In certain embodiments, the expression and/or activity of the TRAC gene and the HLA-A gene in the immune effector cell is down-regulated as compared to a corresponding wild-type cell.

In certain embodiments, the expression and/or activity of the CIITA gene is not down-regulated as compared to the corresponding wild-type cell.

In certain embodiments, the expression and/or activity of the B2M gene is not down-regulated as compared to the corresponding wild-type cell.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene knockout, gene mutation, and/or gene silencing.

In certain embodiments, the modification comprises knocking out either of two TRAC alleles and knocking out either of two HLA-A alleles in the immune effector cell.

In certain embodiments, the modification comprises knocking out the two TRAC alleles and knocking out either of the two HLA-A alleles in the immune cell.

In certain embodiments, the modification comprises knocking out an exon of the TRAC gene and knocking out an exon of the HLA-A gene in the immune cell.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification comprises administering to the immune effector cell sgRNA targeting an exon portion of the TRAC gene.

In certain embodiments, the sgRNA targeting the exon portion of the TRAC gene comprises a nucleotide sequence set forth in any one of SEQ ID NO: 157 to SEQ ID NO: 171.

In certain embodiments, the modification comprises administering to the immune effector cell sgRNA targeting an exon portion of the HLA-A gene.

In certain embodiments, the sgRNA targeting the exon portion of the HLA-A gene comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 172 to SEQ ID NO: 212.

In certain embodiments, the modification further comprises administering to the cell a Cas enzyme.

In certain embodiments, the Cas enzyme includes a Cas9 protein.

In certain embodiments, the antisense RNA comprises an amino acid sequence having at least about 90%, about 91%, about 92%, about 93%, about 94%, about 95%, about 96%, about 97%, about 98%, about 99%, or about 99.5% identity to the nucleotide sequence set forth in any one of SEQ ID NO: 213 to SEQ ID NO: 216.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell. For example, the immune effector cell may be a T cell.

In certain embodiments, the immune effector cell includes an autologous or non-autologous immune effector cell.

In certain embodiments, the cell is an HLA-B homozygous cell.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the cell is an HLA-A homozygous or heterozygous cell.

In certain embodiments, the HLA-A homozygote or heterozygote includes HLA-A*02 homozygote, HLA-A*11 homozygote, HLA-A*02/A*11 heterozygote, or HLA-A*24 homozygote.

For example, the method for preparing an immune effector cell may comprise:
(1) collecting peripheral blood of healthy people, performing HLA typing assay, selecting typing meeting our requirements, separating PBMCs, adding CD3 magnetic beads according to a proportion for incubation, and sorting $CD3^+$ T cells; uniformly mixing CD3/CD28 antibody-coupled magnetic beads, measuring an appropriate amount of magnetic bead suspension according to the calculated amount, adding the magnetic bead suspension into a T cell culture system, activating T cells, and performing overnight culture;
(2) infecting the T cells according to the titer of anti-B7H3 CAR virus;
(3) simultaneously knocking out TRAC and HLA-A genes; and
(4) sorting CD3-negative T cells: adding CD3 magnetic beads according to a proportion, and collecting CD3-T cells (cells not bound to the magnetic beads).

Use, Pharmaceutical Composition, and Treatment Method

In another aspect, the present application provides use of the aforementioned chimeric antigen receptor, the aforementioned isolated nucleic acid molecule, the aforementioned vector, the aforementioned cell, or the aforementioned immune effector cell in the preparation of a CAR-T cell.

In another aspect, the present application provides a pharmaceutical composition comprising the aforementioned antigen-binding polypeptide, the aforementioned chimeric antigen receptor, the aforementioned isolated nucleic acid molecule, the aforementioned vector, the aforementioned cell, and/or the aforementioned immune effector cell, and optionally a pharmaceutically acceptable carrier.

For example, the pharmaceutical composition may include: buffers, such as neutral buffered saline, phosphate buffered saline, and the like; sugars, such as glucose, mannose, sucrose, dextran, or mannitol; proteins; polypeptides or amino acids such as glycine; antioxidants; chelating agents, such as EDTA or glutathione; adjuvants, such as aluminum hydroxide; and preservatives.

For example, the pharmaceutical composition comprises the aforementioned immune effector cell and optionally a pharmaceutically acceptable carrier.

In another aspect, the present application provides use of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition in the treatment of a disease or disorder associated with the expression of B7H3.

In certain embodiments, the disease or disorder associated with the expression of B7H3 includes a disease or disorder associated with up-regulation of the expression of B7H3.

In certain embodiments, the disease or disorder associated with the expression of B7H3 includes cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

In another aspect, the present application provides use of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition in the preparation of a medicament for treating a disease or disorder associated with the expression of B7H3.

In certain embodiments, the disease or disorder associated with the expression of B7H3 includes a disease or disorder associated with up-regulation of the expression of B7H3.

In certain embodiments, the disease or disorder associated with the expression of B7H3 includes cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

In another aspect, the present application provides a method for preventing or treating a disease or disorder associated with the expression of B7H3, comprising administering to a subject in need thereof an effective amount of the aforementioned antigen-binding polypeptide, the aforementioned antigen chimeric receptor, the aforementioned isolated nucleic acid molecule, the aforementioned vector, the aforementioned cell, the aforementioned immune effector cell, and/or the aforementioned pharmaceutical composition.

In certain embodiments, the disease or disorder associated with the expression of B7H3 includes a disease or disorder associated with up-regulation of the expression of B7H3.

In certain embodiments, the disease or disorder associated with the expression of B7H3 includes cancer.

In certain embodiments, the cancer includes adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, or endometrial cancer.

Modified Immune Effector Cell

In another aspect, the present application provides a modified immune effector cell, wherein the expression and/or activity of TRAC gene and HLA-A gene is down-regulated, the expression and/or activity of B2M gene is not down-regulated, and the expression and/or activity of CIITA gene is not down-regulated as compared to the expression and/or activity of corresponding genes in a corresponding unmodified cell; and the HLA-B typing of the modified immune effector cell is matched with the HLA-B typing of a subject.

In certain embodiments, the modified immune effector cell is HLA-B heterozygote and is consistent with two alleles of HLA-B of the subject, or the modified immune effector cell is HLA-B homozygote and is consistent with one of the alleles of HLA-B of the subject.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the modification enables the expression and/or activity of two genes to be down-regulated, wherein the two genes consist of TRAC gene and HLA-A gene.

In certain embodiments, the expression and/or activity of the TRAC gene and the HLA-A gene is down-regulated, the expression and/or activity of the B2M gene is not down-regulated, and the expression and/or activity of the CIITA gene is not down-regulated as compared to a corresponding wild-type cell.

In certain embodiments, the expression and/or activity of two genes is down-regulated as compared to the corresponding wild-type cell, wherein the two genes consist of TRAC gene and HLA-A gene.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene mutation and/or gene silencing.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification comprises administering to the immune effector cell sgRNA targeting an exon portion of the HLA-A gene.

In certain embodiments, the sgRNA targeting the exon portion of the HLA-A gene comprises a nucleotide sequence set forth in any one of SEQ ID NO: 172 to SEQ ID NO: 212.

In certain embodiments, the modification further comprises administering to the immune effector cell sgRNA targeting an exon portion of the TRAC gene.

In certain embodiments, the sgRNA targeting the exon portion of the TRAC gene comprises a nucleotide sequence set forth in any one of SEQ ID NO: 157 to SEQ ID NO: 171.

In certain embodiments, the modification further comprises administering to the cell a Cas enzyme.

In certain embodiments, the Cas enzyme includes a Cas9 protein.

In certain embodiments, the antisense RNA comprises a nucleotide sequence set forth in any one of SEQ ID NO: 213 to SEQ ID NO: 216.

In certain embodiments, the modified immune effector cell expresses a CAR.

In certain embodiments, the CAR comprises an antigen-binding domain, a hinge region, a transmembrane domain, an intracellular co-stimulatory signaling domain, and an intracellular signaling domain.

In certain embodiments, the antigen-binding domain specifically binds to a tumor antigen.

In certain embodiments, the tumor antigen is selected from the group consisting of: CD19, CD20, CD22, CD33, BCMA, IL13Ra2, EGFR, Her2, GD2, and B7H3.

In certain embodiments, the antigen-binding domain is selected from the group consisting of: a monoclonal antibody, a polyclonal antibody, a dimer, a polymer, a multi-specific antibody, an intact antibody, an antibody fragment, a human antibody, a humanized antibody, a chimeric antibody, an Fv fragment, F(ab')2, a single-chain Fv(scFv), and a single-domain antibody (VHH).

In certain embodiments, the transmembrane domain comprises a transmembrane domain derived from one or more proteins selected from the group consisting of: CD8A, CD8B, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4 (CD244), FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, and SLAM.

In certain embodiments, the intracellular co-stimulatory signaling domain comprises an intracellular co-stimulatory signaling domain derived from one or more proteins selected from the group consisting of: CD28, CD137, CD27, CD2, CD7, CD8A, CD8B, OX40, CD226, DR3, SLAM, CDS, ICAM-1, NKG2D, NKG2C, B7H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, and MyD88.

In certain embodiments, the intracellular signaling domain comprises an intracellular signaling domain derived from one or more proteins selected from the group consisting of: CD3ζ, CD3δ, CD3γ, CD3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

In certain embodiments, the hinge region comprises a hinge region derived from one or more proteins selected from the group consisting of: CD28, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, and LIGHT.

In certain embodiments, the CAR further comprises a signal peptide fragment, wherein the C-terminus of the signal peptide fragment is linked to the N-terminus of the targeting moiety.

In certain embodiments, the signal peptide fragment includes a CD8A signal peptide fragment.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

In certain embodiments, the immune effector cell includes a non-autologous immune effector cell.

In another aspect, the present application provides a method for preparing the aforementioned modified immune effector cell, comprising the following steps:
1) selecting an immune effector cell that matches HLA-B typing of a subject; and
2) down-regulating the expression and/or activity of TRAC gene and HLA-A gene in the immune effector cell, not down-regulating the expression and/or activity of B2M gene, and not down-regulating the expression and/or activity of CIITA gene as compared to the expression and/or activity of corresponding genes in a corresponding unmodified cell.

In certain embodiments, the modified immune effector cell is HLA-B heterozygote and is consistent with two alleles of HLA-B of the subject, or the modified immune effector cell is HLA-B homozygote and is consistent with one of the alleles of HLA-B of the subject.

In certain embodiments, the HLA-B homozygote includes HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

In certain embodiments, the modification enables the expression and/or activity of two genes to be down-regulated, wherein the two genes consist of TRAC gene and HLA-A gene.

In certain embodiments, the expression and/or activity of the TRAC gene and the HLA-A gene is down-regulated, the expression and/or activity of the B2M gene is not down-regulated, and the expression and/or activity of the CIITA gene is not down-regulated as compared to a corresponding wild-type cell.

In certain embodiments, the expression and/or activity of two genes is down-regulated as compared to the corresponding wild-type cell, wherein the two genes consist of TRAC gene and HLA-A gene.

In certain embodiments, the down-regulation of the expression level and/or activity of the gene includes down-regulating the expression and/or activity of a nucleic acid molecule encoding the gene; and/or down-regulating the expression and/or activity of a protein product encoded by the gene.

In certain embodiments, the modification comprises: gene mutation and/or gene silencing.

In certain embodiments, the modification comprises administering to the immune effector cell one or more substances selected from the group consisting of: antisense RNA, siRNA, shRNA, and a CRISPR/Cas9 system.

In certain embodiments, the modification comprises administering to the immune effector cell the CRISPR/Cas9 system.

In certain embodiments, the modification comprises administering to the immune effector cell sgRNA targeting an exon portion of the HLA-A gene.

In certain embodiments, the sgRNA targeting the exon portion of the HLA-A gene comprises a nucleotide sequence set forth in any one of SEQ ID NO: 172 to SEQ ID NO: 212.

In certain embodiments, the modification comprises administering to the immune effector cell sgRNA targeting an exon portion of the TRAC gene.

In certain embodiments, the sgRNA targeting the exon portion of the TRAC gene comprises a nucleotide sequence set forth in any one of SEQ ID NO: 157 to SEQ ID NO: 171.

In certain embodiments, the modification further comprises administering to the cell a Cas enzyme.

In certain embodiments, the Cas enzyme includes a Cas9 protein.

In certain embodiments, the antisense RNA comprises a nucleotide sequence set forth in any one of SEQ ID NO: 213 to SEQ ID NO: 216.

In certain embodiments, the immune effector cell includes a human cell.

In certain embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

In certain embodiments, the immune effector cell includes a non-autologous immune effector cell.

In another aspect, the present application provides a composition comprising the aforementioned modified immune effector cell and a pharmaceutically acceptable carrier.

In another aspect, the present application provides use of the aforementioned modified immune effector cell in the preparation of a CAR-T cell.

In another aspect, the present application provides use of the aforementioned modified immune effector cell in the preparation of a medicament for allogeneic therapy.

In another aspect, the present application provides use of the aforementioned modified immune effector cell in the preparation of a medicament for treating a tumor.

In certain embodiments, the tumor includes a solid tumor and a non-solid tumor.

In certain embodiments, the tumor is selected from the group consisting of: liver cancer, gastric cancer, lung cancer, breast cancer, non-small cell lung cancer, B-lymphomas, Hodgkin's lymphoma, gliomas, chronic myelogenous leukemia, and acute myeloid leukemia.

The present application further discloses the following embodiments:

128. A modified immune effector cell, wherein the expression and/or activity of TRAC gene and HLA-A gene is down-regulated, the expression and/or activity of B2M gene is not down-regulated, and the expression and/or activity of CIITA gene is not down-regulated as compared to the expression and/or activity of corresponding genes in a corresponding unmodified cell; and the HLA-B typing of the modified immune effector cell is matched with the HLA-B typing of a subject.

129. The modified immune effector cell according to claim 128, wherein the modified immune effector cell is HLA-B heterozygote and is consistent with two alleles of HLA-B of the subject, or the modified immune effector cell is HLA-B homozygote and is consistent with one of the alleles of HLA-B of the subject.

130. The modified immune effector cell according to claim 129, wherein the HLA-B homozygote comprises HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

131. The modified immune effector cell according to any one of claims 128-130, wherein the modification enables the expression and/or activity of two genes to be down-regulated, wherein the two genes consist of TRAC gene and HLA-A gene.

132. The modified immune effector cell according to any one of claims 128-131, wherein the expression and/or activity of the TRAC gene and the HLA-A gene is down-regulated, the expression and/or activity of the B2M gene is not down-regulated, and the expression and/or activity of the CIITA gene is not down-regulated as compared to a corresponding wild-type cell.

133. The modified immune effector cell according to any one of claims 128-132, wherein the expression and/or activity of two genes is down-regulated as compared to the corresponding wild-type cell, wherein the two genes consist of TRAC gene and HLA-A gene.

134. The modified immune effector cell according to any one of claims 128-133, wherein the down-regulation of the expression level and/or activity of the gene comprises down-regulating the expression and/or activity of a nucleic acid molecule encoding the gene; and/or down-regulating the expression and/or activity of a protein product encoded by the gene.

135. The modified immune effector cell according to any one of claims 128-134, wherein the modification comprises: gene mutation and/or gene silencing.

136. The modified immune effector cell according to any one of claims 128-135, wherein the modification comprises administering to the immune effector cell one or more substances selected from the group consisting of: antisense RNA, siRNA, shRNA, and a CRISPR/Cas9 system.

137. The modified immune effector cell according to any one of claims 128-136, wherein the modification comprises administering to the immune effector cell the CRISPR/Cas9 system.

138. The modified immune effector cell according to claim 137, wherein the modification comprises administering to the immune effector cell sgRNA targeting an exon portion of the HLA-A gene.

139. The modified immune effector cell according to claim 138, wherein the sgRNA targeting the exon portion of the HLA-A gene comprises a nucleotide sequence set forth in any one of SEQ ID NO: 172 to SEQ ID NO: 212.

140. The modified immune effector cell according to any one of claims 137-139, wherein the modification further comprises administering to the immune effector cell sgRNA targeting an exon portion of the TRAC gene.

141. The modified immune effector cell according to claim 140, wherein the sgRNA targeting the exon portion of the TRAC gene comprises a nucleotide sequence set forth in any one of SEQ ID NO: 157 to SEQ ID NO: 171.

142. The modified immune effector cell according to any one of claims 137-141, wherein the modification further comprises administering to the cell a Cas enzyme.

143. The modified immune effector cell according to claim 142, wherein the Cas enzyme comprises a Cas9 protein.

144. The modified immune effector cell according to claim 136, wherein the antisense RNA comprises a nucleotide sequence set forth in any one of SEQ ID NO: 213 to SEQ ID NO: 216.

145. The modified immune effector cell according to any one of claims 128-144, wherein the immune effector cell expresses a CAR.

146. The modified immune effector cell according to claim 145, wherein the CAR comprises an antigen-binding domain, a hinge region, a transmembrane domain, an intracellular co-stimulatory signaling domain, and an intracellular signaling domain.

147. The modified immune effector cell according to claim 146, wherein the antigen-binding domain specifically binds to a tumor antigen.

148. The modified immune effector cell according to claim 147, wherein the tumor antigen is selected from the group consisting of: CD19, CD20, CD22, CD33, BCMA, IL13Ra2, EGFR, Her2, GD2, and B7H3.

149. The modified immune effector cell according to any one of claims 146-148, wherein the antigen-binding domain is selected from the group consisting of: a monoclonal antibody, a polyclonal antibody, a dimer, a polymer, a multispecific antibody, an intact antibody, an antibody fragment, a human antibody, a humanized antibody, a chimeric antibody, an Fv fragment, F(ab')2, a single-chain Fv(scFv), and a single-domain antibody (VHH).

150. The modified immune effector cell according to any one of claims 146-149, wherein the transmembrane domain comprises a transmembrane domain derived from one or more proteins selected from the group consisting of: CD8A, CD8B, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4 (CD244), FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, and SLAM.

151. The modified immune effector cell according to any one of claims 146-150, wherein the intracellular co-stimulatory signaling domain comprises an intracellular co-stimulatory signaling domain derived from one or more proteins selected from the group consisting of: CD28, CD137, CD27, CD2, CD7, CD8A, CD8B, OX40, CD226, DR3, SLAM, CDS, ICAM-1, NKG2D, NKG2C, B7H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, and MyD88.

152. The modified immune effector cell according to any one of claims 146-151, wherein the intracellular signaling domain comprises an intracellular signaling domain derived from one or more proteins selected from the group consisting of: CD3ζ, CD3δ, CD3γ, CD3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

153. The modified immune effector cell according to any one of claims 146-152, wherein the hinge region comprises a hinge region derived from one or more proteins selected from the group consisting of: CD28, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, and LIGHT.

154. The modified immune effector cell according to any one of claims 146-153, wherein the CAR further comprises a signal peptide fragment, and the C-terminus of the signal peptide fragment is linked to the N-terminus of a targeting moiety.

155. The modified immune effector cell according to any one of claims 146-154, wherein the signal peptide fragment comprises a CD8A signal peptide fragment.

156. The modified immune effector cell according to any one of claims 128-155, wherein the immune effector cell comprises a human cell.

157. The modified immune effector cell according to any one of claims 128-156, wherein the immune effector cell comprises a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

158. The method according to any one of claims 128-157, wherein the immune effector cell comprises a non-autologous immune effector cell.

159. A method for preparing the modified immune effector cell according to any one of claims 128-158, comprising the following steps:
   1) selecting an immune effector cell that matches HLA-B typing of a subject; and
   2) down-regulating the expression and/or activity of TRAC gene and HLA-A gene in the immune effector cell, not down-regulating the expression and/or activity of B2M gene, and not down-regulating the expression and/or activity of CIITA gene as compared to the expression and/or activity of corresponding genes in a corresponding unmodified cell.

160. The method according to claim 159, wherein the modified immune effector cell is HLA-B heterozygote and is consistent with two alleles of HLA-B of the subject, or the modified immune effector cell is HLA-B homozygote and is consistent with one of the alleles of HLA-B of the subject.

161. The method according to claim 160, wherein the HLA-B homozygote comprises HLA-B*40 homozygote, HLA-B*15 homozygote, HLA-B*46 homozygote, HLA-B*13 homozygote, HLA-B*51 homozygote, HLA-B*58 homozygote, HLA-B*07 homozygote, HLA-B*35 homozygote, HLA-B*44 homozygote, HLA-B*52 homozygote, HLA-B*57 homozygote, HLA-B*54 homozygote, and HLA-B*55 homozygote.

162. The method according to any one of claims 159-161, wherein the modification enables the expression and/or activity of two genes to be down-regulated, wherein the two genes consist of TRAC gene and HLA-A gene.

163. The method according to any one of claims 159-162, wherein the expression and/or activity of the TRAC gene and the HLA-A gene is down-regulated, the expression and/or activity of the B2M gene is not down-regulated, and the expression and/or activity of the CIITA gene is not down-regulated as compared to a corresponding wild-type cell.

164. The method according to any one of claims 159-163, wherein the expression and/or activity of two genes is down-regulated as compared to the corresponding wild-type cell, wherein the two genes consist of TRAC gene and HLA-A gene.

165. The method according to any one of claims 159-164, wherein the down-regulation of the expression level and/or activity of the gene comprises down-regulating the expression and/or activity of a nucleic acid molecule encoding the gene; and/or down-regulating the expression and/or activity of a protein product encoded by the gene.

166. The method according to any one of claims 159-165, wherein the modification comprises: gene mutation and/or gene silencing.

167. The method according to any one of claims 159-166, wherein the modification comprises administering to the immune effector cell one or more substances selected from the group consisting of: antisense RNA, siRNA, shRNA, and a CRISPR/Cas9 system.

168. The method according to any one of claims 159-167, wherein the modification comprises administering to the immune effector cell the CRISPR/Cas9 system.

169. The method according to claim 168, wherein the modification comprises administering to the immune effector cell sgRNA targeting an exon portion of the HLA-A gene.

170. The method according to claim 169, wherein the sgRNA targeting the exon portion of the HLA-A gene comprises a nucleotide sequence set forth in any one of SEQ ID NO: 172 to SEQ ID NO: 212.

171. The method according to any one of claims 168-171, wherein the modification comprises administering to the immune effector cell sgRNA targeting an exon portion of the TRAC gene.
172. The method according to claim 171, wherein the sgRNA targeting the exon portion of the TRAC gene comprises a nucleotide sequence set forth in any one of SEQ ID NO: 157 to SEQ ID NO: 171.
173. The method according to any one of claims 168-172, wherein the modification further comprises administering to the cell a Cas enzyme.
174. The method according to claim 173, wherein the Cas enzyme comprises a Cas9 protein.
175. The method according to claim 167, wherein the antisense RNA comprises a nucleotide sequence set forth in any one of SEQ ID NO: 213 to SEQ ID NO: 216.
176. The method according to any one of claims 159-175, wherein the immune effector cell comprises a human cell.
177. The method according to any one of claims 159-176, wherein the immune effector cell comprises a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.
178. The method according to any one of claims 159-177, wherein the immune effector cell comprises a non-autologous immune effector cell.
179. A composition comprising the modified immune effector cell according to any one of claims 128-158 and a pharmaceutically acceptable carrier.
180. Use of the modified immune effector cell according to any one of claims 128-158 in the preparation of a CAR-T cell.
181. Use of the modified immune effector cell according to any one of claims 128-158 in the preparation of a medicament for allogeneic therapy.
182. Use of the immune effector cell according to any one of claims 128-158 in the preparation of a medicament for treating a tumor.
183. The use according to claim 182, wherein the tumor comprises a solid tumor and a non-solid tumor.
184. The use according to any one of claims 182-183, wherein the tumor is selected from the group consisting of: liver cancer, gastric cancer, lung cancer, breast cancer, non-small cell lung cancer, B-lymphomas, Hodgkin's lymphoma, gliomas, chronic myelogenous leukemia, and acute myeloid leukemia.

Without being bound by any theory, the following examples are intended only to illustrate the chimeric antigen receptor, immune effector cell, preparation method, use, etc., of the present application, and are not intended to limit the scope of the present application.

EXAMPLES

Example 1

1.1 Affinity Assay of Single-Domain Antibodies

The B7H3-Fc recombinant protein was immobilized to a CM5 chip with 10 mM acetate buffer, and the ability of each of the above-prepared single-domain antibodies obtained by screening to bind to the B7H3-Fc recombinant protein was measured with each of the single-domain antibodies as a mobile phase.

(1) Reagent Preparation

Running reagent: containing 10 mM N-(2-hydroxyethyl) piperazine-N-2 sulfonic acid (HEPES), 150 mM sodium chloride (NaCl), 3 mM ethylenediaminetetraacetic acid (EDTA), and 0.005% Tween-20, pH adjusted to 7.4.

A human IgG (Fc) capture kit comprising a mouse anti-human IgG (Fc) antibody, an immobilization reagent (sodium acetate, pH 5.0), and a regeneration reagent (magnesium chloride).

An amino coupling kit comprising N-hydroxysuccinimide (NHS), 1-ethyl-(3-dimethylaminopropyl)carbodiimide hydrochloride (EDC), and ethanolamine (pH 8.5). To each tube of EDC and NHS was added 10 mL of deionized water, and the mixed solutions were aliquoted and stored at −18° C. or lower, with a two-month shelf life.

(2) Chip Preparation

The mouse anti-human IgG (Fc) antibody was diluted with the immobilization reagent (sodium acetate, pH 5.0): 950 μL of the immobilization reagent was added to 50 μL of the mouse anti-human IgG (Fc) antibody. The dilution was used for immobilization in eight channels. First, the surface of the CM5 chip was activated for 360 s with EDC and NHS at a flow rate of 10 μL/min. Then, the mouse anti-human IgG (Fc) antibody was injected into the channels (channels 1-8, Fc1,2) at a flow rate of 10 μL/min for about 360 s, with the level of immobilization at about 7000 to 14,000 RU. Finally, the chip was blocked with ethanolamine at 10 μL/min for 420 s.

(3) Buffer Exchange

Buffer exchange was performed for human B7H3 protein using a desalting column and the corresponding running reagent, and the concentration of the sample after the exchange was determined.

(4) Ligand Capture

The antibody was diluted to 10 μg/mL with the running reagent, and the dilution was injected into the experimental channels (Fc2) for human IgG (Fc) capture at a flow rate of 10 μL/min at about 300 RU. The reference channels (Fc1) did not require ligand capture.

(5) Analyte Multicycle Analysis

The human B7H3 protein was diluted 2-fold with the running reagent. The diluted human B7H3 protein was injected into the experimental channels and the reference channels in sequence at a flow rate of 30 μL/min, and corresponding periods of association and dissociation were allowed. The association and dissociation steps were all performed in the running reagent. After each concentration analysis, the chip needed to be regenerated with magnesium chloride at a flow rate of 20 μL/min for 30 s to wash away the ligand and undissociated analyte. For the next concentration analysis, the experimental channels needed to recapture the same amount of ligand.

(6) Data Analysis

A KD value was calculated for each sample using Biacore 8K analysis software Biacore Insight Evaluation Software. The reference channels (Fc1) were used for background subtraction.

The results are shown in Table 1. The B7H3 single-domain antibodies 1A5 and 1G7 and humanized antibodies thereof of the present application all have relatively high affinity for the human B7H3 protein.

TABLE 1

The results of the binding of single-domain antibodies to B7H3-Fc recombinant protein

| | Ka ($M^{-1}s^{-1}$) | Kd ($s^{-1}$) | KD (M) |
|---|---|---|---|
| 1A5 | $6.09 \times 10^5$ | 0.004503 | $7.394 \times 10^{-9}$ |
| 1G7 | $1.150 \times 10^6$ | 0.006182 | $5.375 \times 10^{-9}$ |

1.2 Affinity Curves of Antibodies

Figure 2:
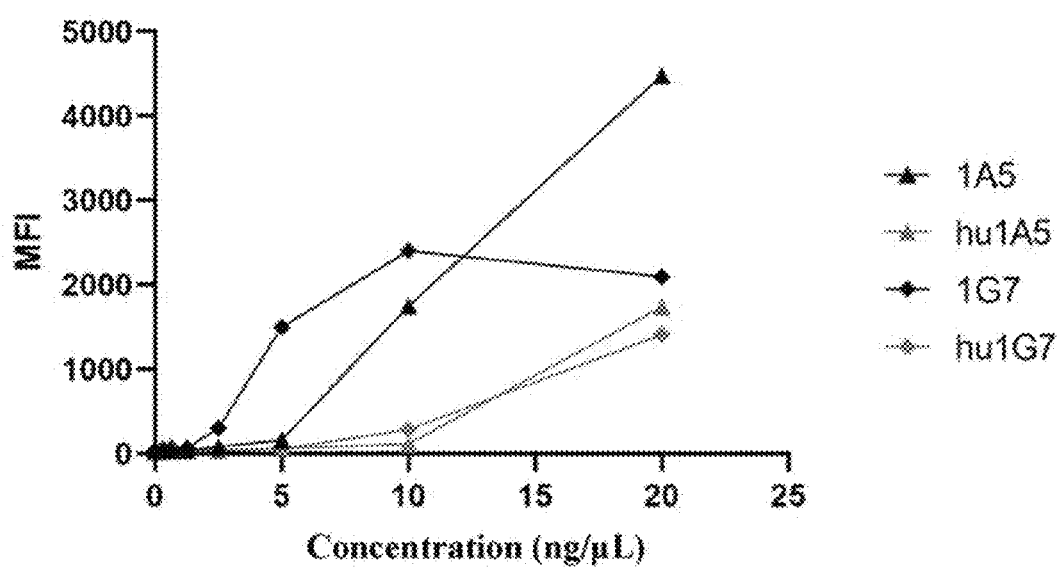
FIG. 2 shows affinity curves of anti-B7H3 VHH antibodies described in the present application.

Recombinant antibodies with different concentrations were incubated with U251 cells (expressing B7H3), and the binding of the antibodies to the cell surface was assayed by the mean fluorescence intensity (MFI) of the cells. From the results shown in FIG. 2, the 1A5 and 1G7 antibodies and the humanized antibodies thereof can effectively bind to the surface of the U251 cells.

1.3 ADCC Function of Antibodies

Figure 3:
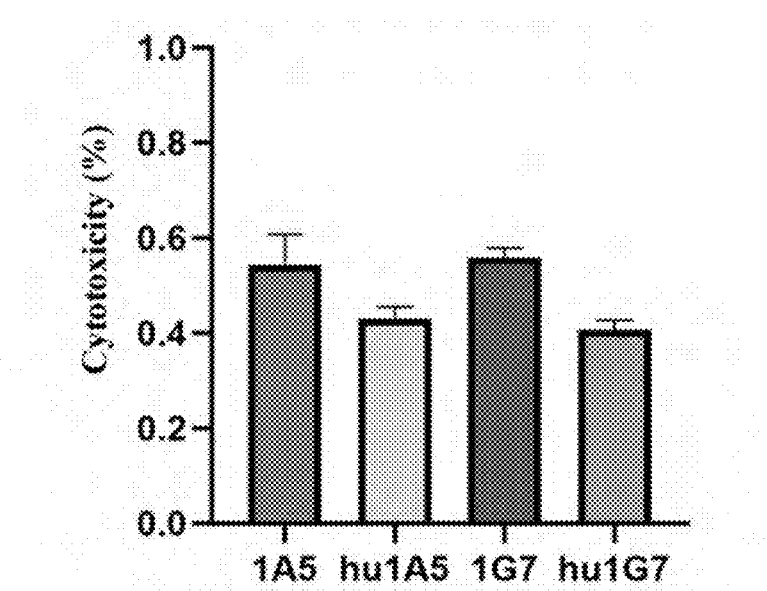
FIG. 3 shows ADCC function assay results of the anti-B7H3 VHH antibodies described in the present application.

The equivalent amount of NK cells and U251-LG cells were co-cultured, 200 ng/μL of recombinant antibody was added thereto, and a cytotoxicity effect mediated by the antibody was assayed after co-culturing for 24 h. From the results shown in FIG. 3, the 1A5 and 1G7 antibodies and the humanized antibodies thereof can effectively kill the U251-LG tumor cells by ADCC.

1.4 Design of Anti-B7H3 Chimeric Antigen Receptor (CAR)

The anti-B7H3 CAR structure comprised: a B7H3 antigen-binding region (derived from an anti-B7H3 single-domain antibody LAS and having an amino acid sequence set forth in SEQ ID NO: 28), a CD8A extracellular hinge region, a CD8A transmembrane region, a 4-1BB intracellular co-stimulatory domain, and a CD3ζ activation signal domain. The amino acid sequence of the non-antigen-binding domain of anti-B7H3 CAR is set forth in SEQ ID NO: 34, and the nucleotide sequence is set forth in SEQ ID NO: 38.

1.5 Construction of Anti-B7H3 CAR Lentiviral Vector

Figure 1A:
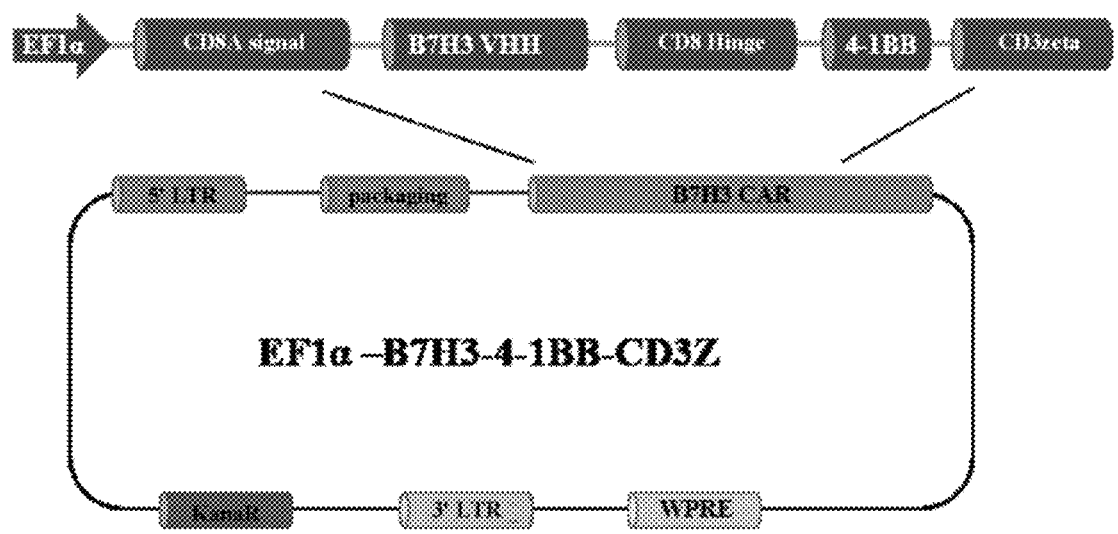
FIG. 1A shows an anti-B7H3 CAR gene lentiviral expression vector described in the present application.
Figure 1B:
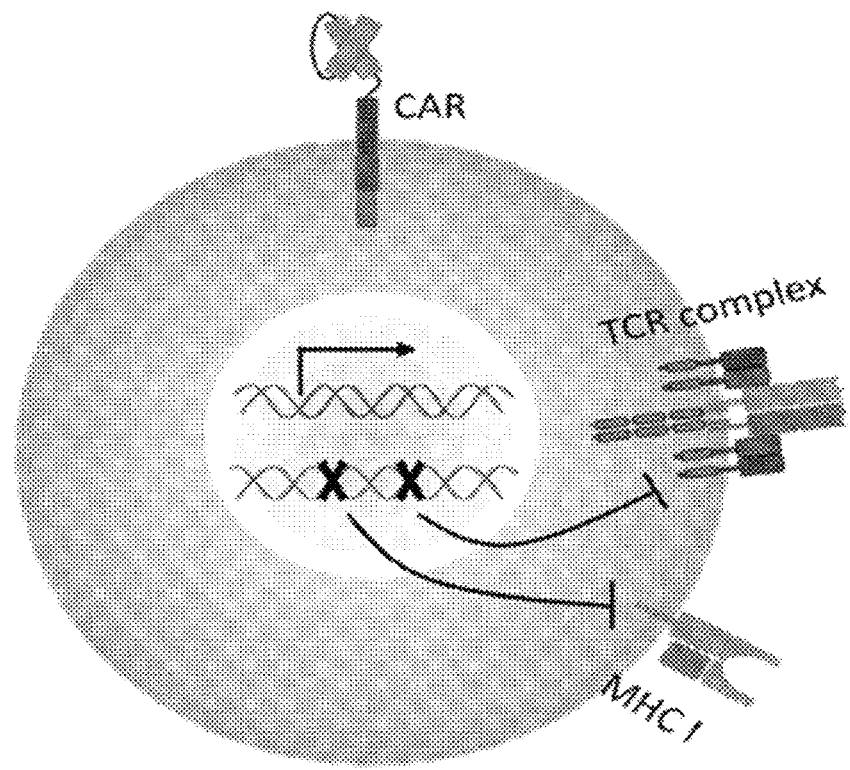
FIG. 1B shows a strategy for constructing the anti-B7H3 UCAR-T cell of the present application.

According to the sequence information on B7H3 and the structure of the CAR vector, an anti-B7H3 CAR lentiviral expression vector was constructed, with the vector schematic shown in FIG. 1. The optimization was performed: a commercial lentiviral expression vector pCDH-CMV-MCS-EF1-copGFP was selected as a backbone, and element modification was performed on the basis of the vector. First, an ampicillin resistance gene β-lactamase on the vector was replaced with aminoglycoside phosphotransferase derived from Tn5 to enable the vector to have kanamycin resistance. Secondly, we deleted the CMV promoter and its adjacent downstream multiple cloning site, which were potentially threatening in vivo applications. Finally, the copGFP gene that was started to express by the EF1 promoter in the original vector was deleted, a SalI enzyme digestion site was retained, and a SmaI enzyme digestion site was added to the 5' end of SalI for vector construction to form a final target vector. The added SmaI enzyme digestion site was a single enzyme digestion site of the final target vector, and other sequence portions of the vector did not have the enzyme digestion site. After the optimization, the chimeric antigen receptor lentiviral expression vector was constructed, and lentiviral packaging was performed after confirming that the sequence was correct by Sanger sequencing.

Example 2

2.1 Design of Guide RNA

Corresponding gene sequences were searched and downloaded through a website https://www.ncbi.nlm.nih.gov/, the gene sequences were opened by using SnapGene software, and sgRNAs could be designed on different exons of target genes. The sgRNA of the CRISPR/Cas9 system used in this example was designed following a non-restrictive principle of: 5'-NNN(20)-NGG-3', NGG being referred to as a protospacer adjacent motif (PAM), wherein N represented A, T, C, or G. Since many sgRNAs could be designed on the same exon and the sgRNA composed of 20 nucleotide sequences could repeatedly occur in a genome, the design and evaluation of sgRNAs were performed using the website http://crispr.cos.uni-heidelberg.de. An exon sequence was pasted to the website, and the sgRNAs were designed and subjected to a prediction evaluation. The higher the score in the evaluation was, the higher the editing efficiency and the lower the off-target risk could exist. The sgRNAs with higher scores were selected for assay. The sgRNAs targeting the TRAC gene were set forth in SEQ ID NO: 157 to SEQ ID NO: 171, the sgRNAs targeting the HLA-A02 gene were set forth in SEQ ID NO: 172 to SEQ ID NO: 193, the sgRNAs targeting the HLA-A11 gene were set forth in SEQ ID NO: 194 to SEQ ID NO: 204, and the sgRNAs targeting the HLA-A24 gene were set forth in SEQ ID NO: 205 to SEQ ID NO: 212, which were synthesized by GenScript Biotech Corporation.

2.2 Donor Selection

HLA-B homozygotes which matched with HLA-B typing of a receptor were selected based on the HLA-B typing of the receptor.

First, the donor source was based on HLA-B homozygotes in the population, and one of the alleles of HLA-B in the patient was consistent with the HLA-B homozygotes in the donor, so that cells from these donors could cover a high number of patient populations, and the rejection response caused by inconsistencies in HLA-B subtypes was reduced. HLA-B, such as B*40 homozygote, B*15 homozygote, B*46 homozygote, B*13 homozygote, B*51 homozygote, B*58 homozygote, B*07 homozygote, B*35 homozygote, B*44 homozygote, B*52 homozygote, B*57 homozygote, B*54 homozygote, and B*55 homozygote, was mainly selected, which had relatively high frequency in the population. HLA-A, such as A*02 homozygote, A*11 homozygote, and A*02/A11 heterozygote, was selected, which had relatively high frequency in the population.

2.3 Preparation of CD3+ T Cells (1) Isolation of PBMCs from Peripheral Blood Peripheral blood was collected from healthy donors and diluted with PBS buffer at a rate of 1:1. A cell isolation solution (Ficoll) with a blood volume of ⅓ after dilution was first added into a new 50 mL centrifuge tube, then the blood cell dilution was added very slowly along the tube wall, and the mixture was centrifuged at room temperature for 20 min at 800 g (for the centrifuge, the acceleration speed was set as 1, and the deceleration speed was set as 0). After centrifugation, the liquid in the centrifuge tube was divided into PBS, a serum layer, a leucocyte layer, a lymphocyte isolation solution, and a red blood cell layer from top to bottom. The PBS and serum layer were removed. The leucocyte layer was transferred to a new 50 mL centrifuge tube, PBS was added to 40 mL to wash the cells, and the mixture was centrifuged for 10 min at 450 g. The supernatant was discarded after centrifugation to obtain peripheral blood mononuclear cells. The cells were resuspended and then subjected to cell counting.

(2) Thawing of Cryopreserved Healthy Human PBMCs

Cryopreserved healthy human PBMC cells were thawed in a 37° C. water bath. After complete thawing, the cells were pipetted into a 15 mL centrifuge tube containing 10 mL of X-VIVO15 culture medium containing 10% FBS (purchased from LONZA), and centrifuged for 8 min at 400 g; the supernatant was discarded, 2 mL of X-VIVO15 culture medium (containing 10% FBS and DNase I with a final concentration of 100 μg/mL) was added, and the cells were incubated at room temperature for 15 min and shaken continuously during incubation; the solution after incubation was filtered by using a 40 μm filter; 10 mL of PBS buffer was pipetted to resuspend the cells at the bottom, and then the cells were added onto the filter; the cells were centrifuged for 8 min at 400 g after filtration, and the supernatant was discarded after centrifugation; the cells were resuspended and then subjected to cell counting.

(3) Sorting of CD3+ T Cells

T cells in the peripheral blood mononuclear cells (PBMCs) were extracted using a EasySep™ human T cell sorting kit (purchased from StemCell Technologies, Catalog No. 17951). The density of PBMCs was adjusted to $5\times10^7$ cells/mL, and a PBS buffer was added in a range of 0.25-2 mL; a cocktail was added firstly and mixed uniformly, and an isolation cocktail was then added at 50 μL/mL; after uniform mixing, the mixture was left at room temperature for 5 min; the RapidSpheres were vortexed by a vortex oscillator for 30 s, added into the cells at 40 μL/mL, and mixed uniformly; the mixture was supplemented with a buffer to the fold of 2.5 mL, and gently pipetted up and down for 2-3 times; the mixture was added into cryopreservation tubes with 2.5 mL in each tube, and the tubes were placed on a magnetic frame and left at room temperature for 3 min; the covers of the cryopreservation tubes were gently removed, and the magnetic frame was carefully picked up by holding two ends of the magnetic frame and inverted for 2-3 s; the cell liquids were pouring into new centrifuge tubes at one time; the cells were resuspended in 10-20 mL of a buffer (depending on the number of cells) and then centrifuged for 10 min at 300 g, and the supernatant was discarded to obtain CD3+ T cells.

(4) Activation of T Cells

An activating reagent was prepared according to a volume ratio of culture medium: Transact=99:1, the culture medium was X-VIVO15 culture medium (containing 5% FBS, 200 U/mL IL2, 10 ng/mL IL7, and 5 ng/ml IL15), and Transact was purchased from Miltenyi. The T cells were thoroughly resuspended in 1 mL of activating reagent (containing 10 μL of Transact) per $1\times10^6$ cells, and then incubated in an incubator with 5% $CO_2$ at 37° C. for 1 day.

Example 3

3.1 Virus Transfer

CD3+ T cells were obtained according to the method in Example 2 (D0) and activated with CD3/CD28 antibody magnetic beads. After activation, lentiviral vectors (anti-B7H3 CAR lentiviral expression vectors prepared in Example 1) were transfected on D1, the lentiviral vectors were washed off on D2, and electroporation was performed on D3.

3.2 Gene Knockout

RNP complexes were transferred to the activated T cells prepared in Example 3.1 (the CAR-T cells on D3 were used as starting cells) by electroporation using an electroporation kit (purchased from LONZA, Catalog No. V4XXP-3024). After sampling and counting, the cells were collected and centrifuged, and the cell pellet was resuspended in PBS. A culture medium (X-VIVO15 culture medium+10% FBS+ IL2 (200 U/mL)+IL7 (10 ng/mL)+IL15 (5 ng/ml)) was pre-heated for 30 min in advance in a well plate. An electroporation buffer was prepared according to a ratio of Nucleofector Solution:Supplement=82:18; the RNP complexes were distributed according to each electroporation system using $1\times10^7$ cells (Cas9:sgRNA=2:1). 10 μg of sgRNA was first added to a PCR tube (without RNase), 20 μg of Cas9 protein (purchased from Thermo, Catalog No. A36499) was then added, and the mixture was mixed gently and incubated at room temperature for 12 min. The cells described above were counted and centrifuged for 8 min at 300 g, and the supernatant was discarded. PBS was added to resuspend the cells, 1E7 cells were pipetted and centrifuged again for 8 min at 300 g, and the supernatant was discarded. The cells were resuspended in 100 μL of the prepared electroporation buffer. The incubated RNP complexes were added to the cell suspension described above. The mixture was gently mixed and gently transferred to an electroporation cuvette. The electroporation cuvette was placed on a Lonza-4D electroporation apparatus and subjected to electroporation using an EO-115 electroporation program. A pre-heated culture medium was added into the electroporation cuvette, the cells were transferred into the pre-heated culture medium in the well plate by using a matched pipette and then placed in an incubator with 5% $CO_2$ at 37° C. for 48 h, and then the cells were collected. The editing efficiency was assayed by Sanger sequencing, and the knockout efficiency of the collected cells was assayed by FACS.

sgRNA sequences were as follows: TRAC sgRNA: AGAGTCTCTCAGCTGGTACA (SEQ ID NO: 157), A02 sgRNA: CTGACCATGAAGCCACCCTG (SEQ ID NO: 174), and A11 sgRNA: GGCCCCTCCTGCTCTATCCA (SEQ ID NO: 204).

3.3 Sorting of CD3-Negative T Cells

CD3-negative T cells were sorted. The cells were counted and centrifuged, and the supernatant was discarded; the cells were resuspended in a buffer and mixed uniformly; CD3 magnetic beads were added according to 20 μL of CD3 magnetic beads per $10^7$ cells, and the mixture was mixed uniformly and incubated in a refrigerator at 4° C.; the cells were washed with the buffer and centrifuged, and then the magnetic beads were isolated; a column was first put on a magnetic pole, and a centrifuge tube was correspondingly put below the magnetic pole; the column (LD) was infiltrated in the buffer, and the cells were added onto the column without generating bubbles; the column was washed 2 times with the buffer, the washed liquid (CD3-T) was collected in a 15 mL centrifuge tube, and a part of the cells were subjected to cell counting.

3.4 Cell Culturing

The cell state was observed under a microscope. The cells were diluted, counted, and supplemented with a full culture medium to maintain the cell density at $3 \times 10^5$ to $1 \times 10^6$ cells/mL. Liquid was supplemented/changed in the middle time, and the cells were cultured at 37° C. with 5% $CO_2$. Cell harvesting: the cell suspension was collected in a cell centrifuge tube and centrifuged, and the supernatant was discarded. The cells were washed with normal saline again and centrifuged. A cryopreservation solution was prepared, and the centrifuged cells were resuspended in the cryopreservation solution. The cell suspension was pipetted to a cell cryopreservation bag for a final product by using a syringe, and the cell cryopreservation bag was labeled for the later cryopreservation.

3.5 Assay of Gene Knockout Efficiency (1) Sanger Sequencing Assay

The cells were counted. $3 \times 10^4$ to $5 \times 10^4$ cells were centrifuged for 5 min at 2000 r/min, and the supernatant was discarded as much as possible. 20 µL of DE lysis buffer was added into each tube. The lysed cells were added into a PCR tube, centrifuged instantaneously, and then placed into a PCR apparatus with the following conditions: 65° C. for 30 min, 4° C. for 30 s, 95° C. for 2 min, and 16° C. for infinite time. PCR was performed by using primer pairs TRAC-For/TRAC-Rev or HLA-A For/HLA-A Rev, and the lysed product was used as a template. The PCR product was sent to Genewiz for Sanger sequencing. After obtaining the Sanger sequencing results, the editing site and the editing efficiency were predicted with the EditR editor on the website: https://moriaritylab.shinyapps.io/editr_v10/.

(2) Cell Counting by Flow Cytometry

10E5 to 10E8 cells were centrifuged for 5 min at 2000 rpm, and the supernatant was discarded. 100 µL of PBS buffer was added to each tube to resuspend the cells, and 5 µL of anti-human AB TCR-APC antibody (purchased from eBioscience), 5 µL of HLA-A02 monoclonal antibody (BB7.2), APC, and eBioscince™ antibody (purchased from Invitrogen) were added. The mixture was mixed uniformly and incubated at room temperature for 10 min. After being centrifuged for 5 min at 2000 rpm, the cells were washed 2 times with the PBS buffer, resuspended, and assayed by a BD FACSAria flow cytometer. The positive expression rates of TCR and HLA-A02 on the cell surface could be obtained. Knockout efficiency=(A−B)/A×100%, wherein A was the positive expression rate of the control group; B was the positive expression rate of the knockout group.

Figure 4A:
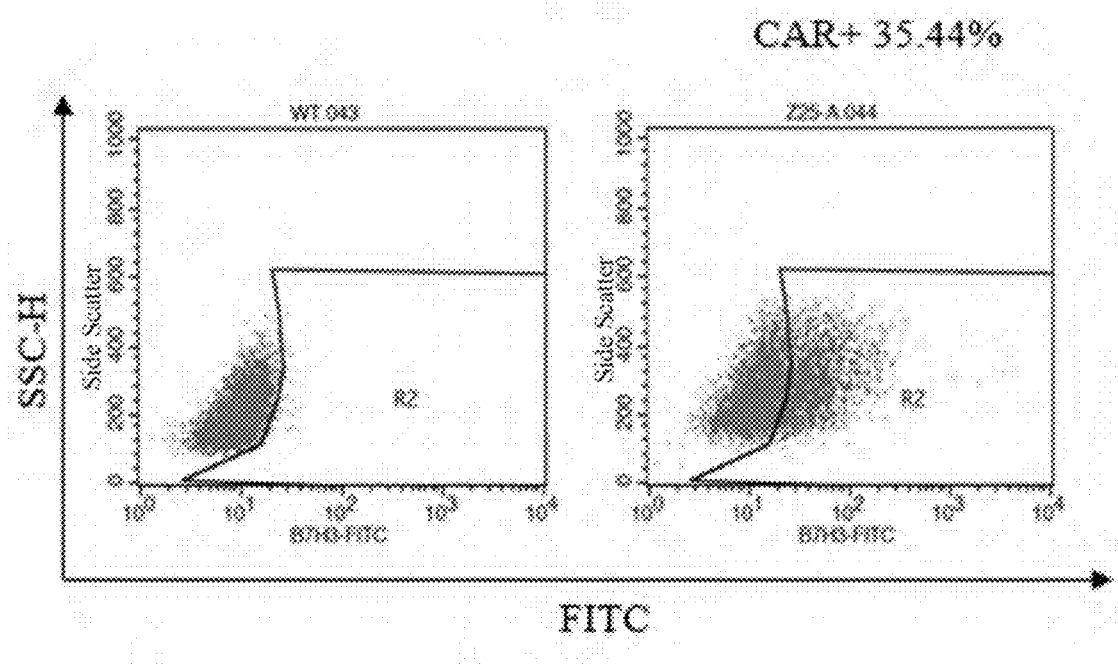
FIGS. 4A-4C show cell phenotype assay results of anti-B7H3 UCAR-T cells described in the present application.
Figure 4B:
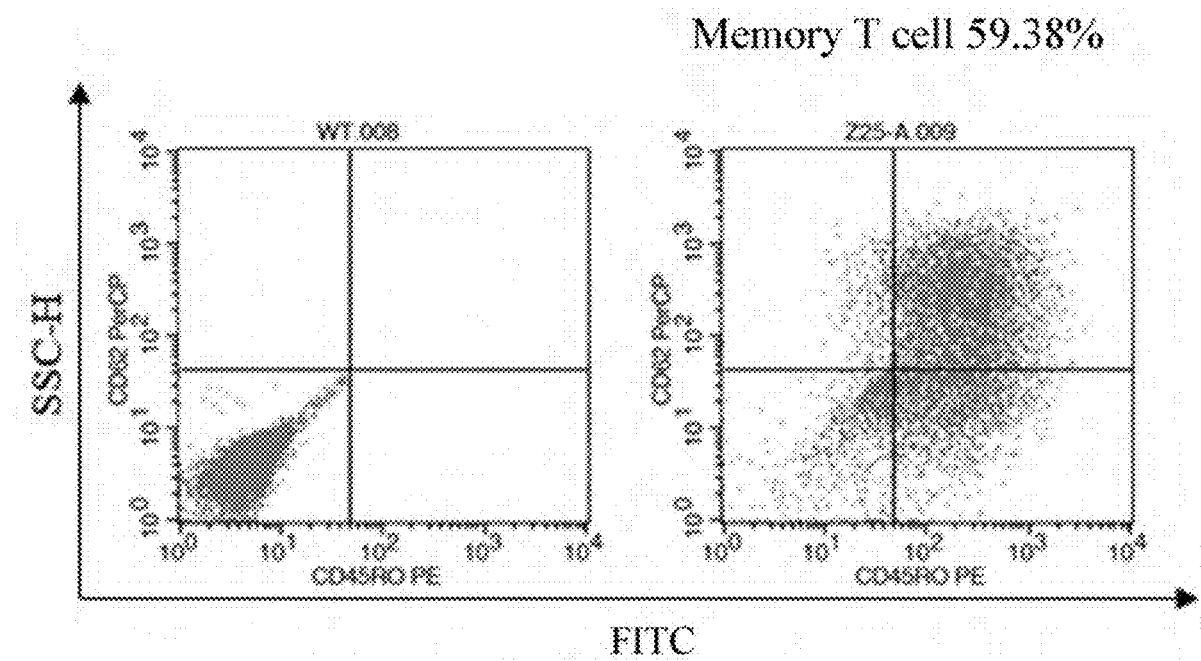
Figure 4C:
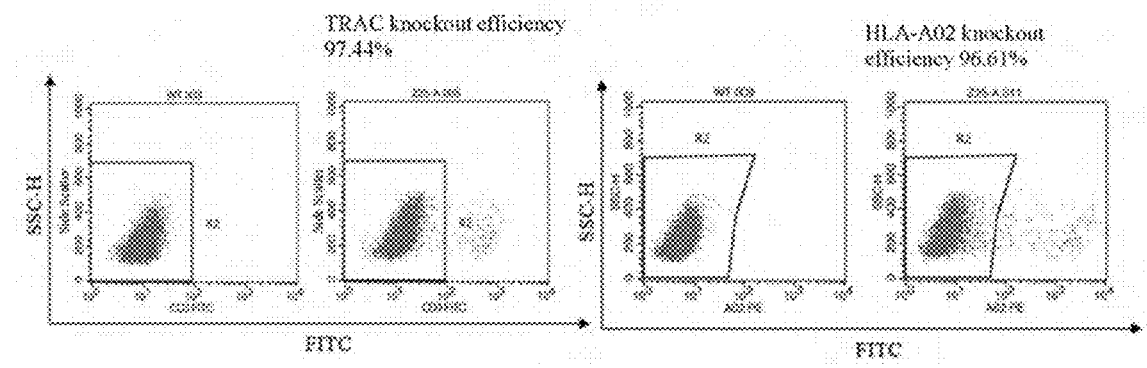

The results are shown in FIGs. 4A-4C. The CAR positive rate of anti-B7H3 UCAR-T cells can be more than 30% (FIG. 4A), the central memory ratio of the anti-B7H3 UCAR-T cells is about 50% (FIG. 4B), and the double knockout efficiency of the anti-B7H3 UCAR-T cells is up to 90% (FIG. 4C).

Example 4. In Vitro Cytotoxicity Analysis of Anti-B7H3 UCAR-T Cells

4.1 Killing of Anti-B7H3 UCAR-T Cells for Target Cells (1) B7H3 target cells: PANC-1-Luciferase; the state of the target cells was adjusted to the log phase, and the cells were continuously passaged 2 times before experiments;

(2) The anti-B7H3 UCAR-T cells and T cells in a control group anti-B7H3 CAR-T were prepared. The knockout efficiency, transfection efficiency, CD3-T sorting efficiency, and the proportion of memory T cells were assayed by flow cytometry, and the amplification fold was counted;

(3) several groups of prepared cells were collected by centrifugation, each group of $6 \times 10^6$ cells;

(4) the target cells were resuspended in 1640+10% FBS. For each target, three 24-well plates were taken, and the target cells were seeded at $2 \times 10^5$ cells/well (both target and effector cells were seeded at a density of $2 \times 10^6$ cells/mL). Effector cells were then added in an E/T (effector-to-target ratio, effector cell:target cell) ratio. Each well was supplemented to a maximum volume (e.g., 600 µL). The same amount of target cells were seeded in the control group, without effector cells (600 µL). The well plates were incubated in an incubator with 5% $CO_2$ at 37° C. for 24 h. The cells were plated in the following E/T: 1:2, 1:1, 2:1, 5:1, and 10:1 and repeated three times; and (5) After 24 h of culture, the well plates were taken out of the incubator, and 200 µL of supernatant was collected. The lysis capacity of the recombinant CAR-T cells on the target cells was then reflected by the assay of Luciferase activity.

The calculation formula for the lysis percentage of the target cells was as follows:

$$\text{Lysis \%} = \left(1 - \frac{Luc \text{ Activity}_{Mixed\,sample}}{Luc \text{ Activity}_{Control\,sample}}\right) \times 100\%$$

Figure 5:
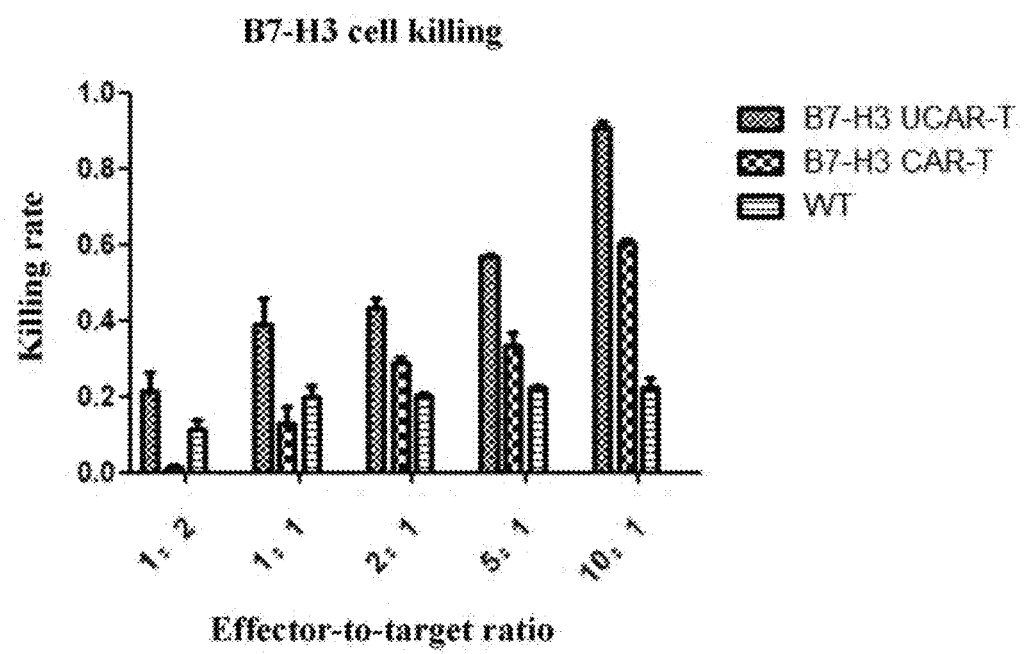
FIG. 5 shows a killing result of the anti-B7H3 UCAR-T cells described in the present application on target cells.

Analysis of results: the anti-B7H3 CAR-T cells and anti-B7H3 UCAR-T have a significant killing effect on the PANC-1-Luciferase cells. The anti-B7H3 UCAR-T cells can achieve more than 90% of killing efficiency when the effector-to-target ratio is 10:1 (see FIG. 5).

Figure 6A:
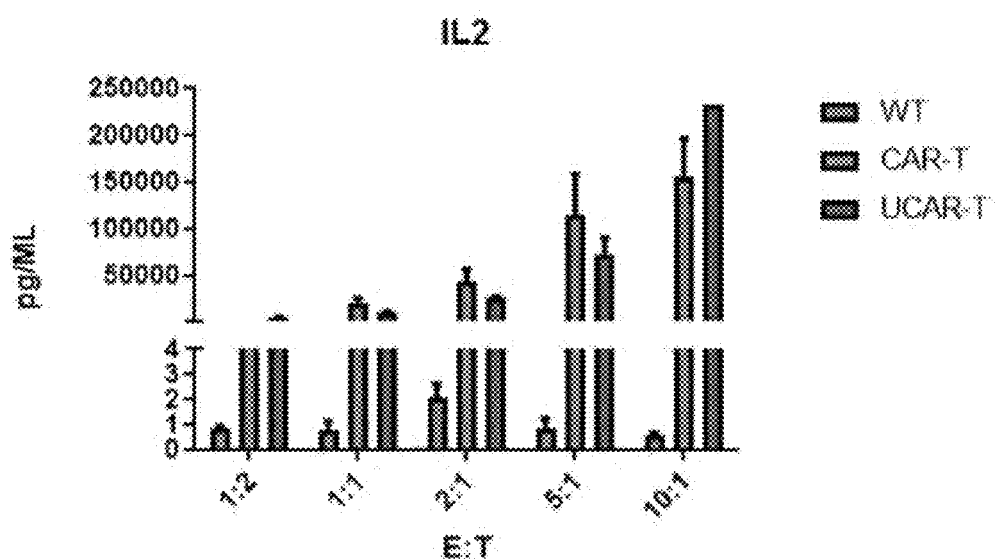
FIGS. 6A-6C show cytokine secretion assay results of the anti-B7H3 UCAR-T cells described in the present application co-cultured with the target cells.
Figure 6B:
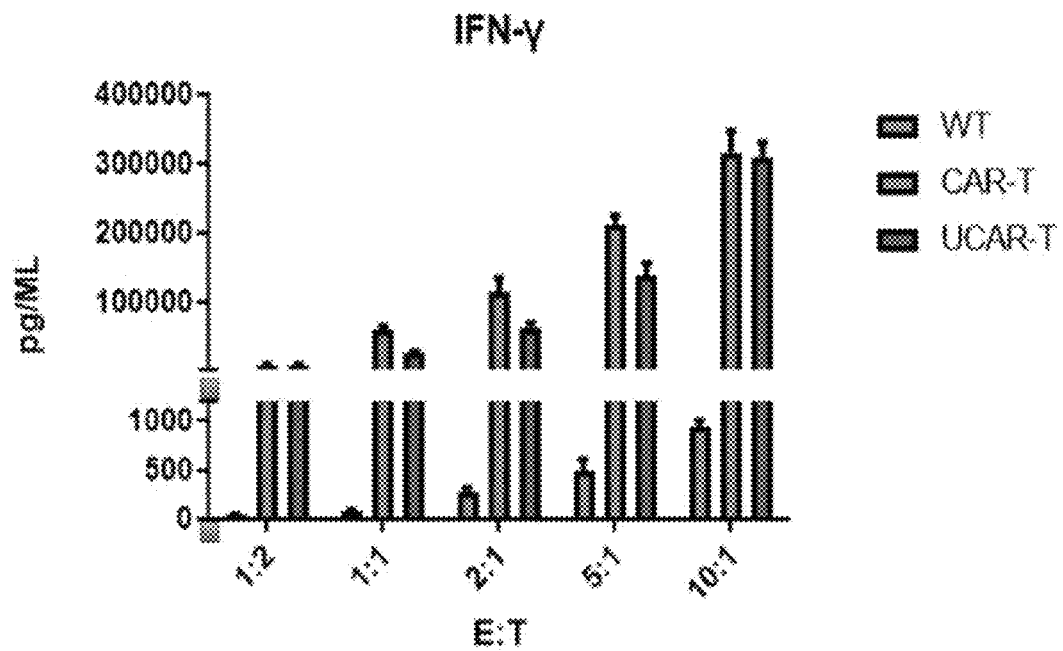
Figure 6C:
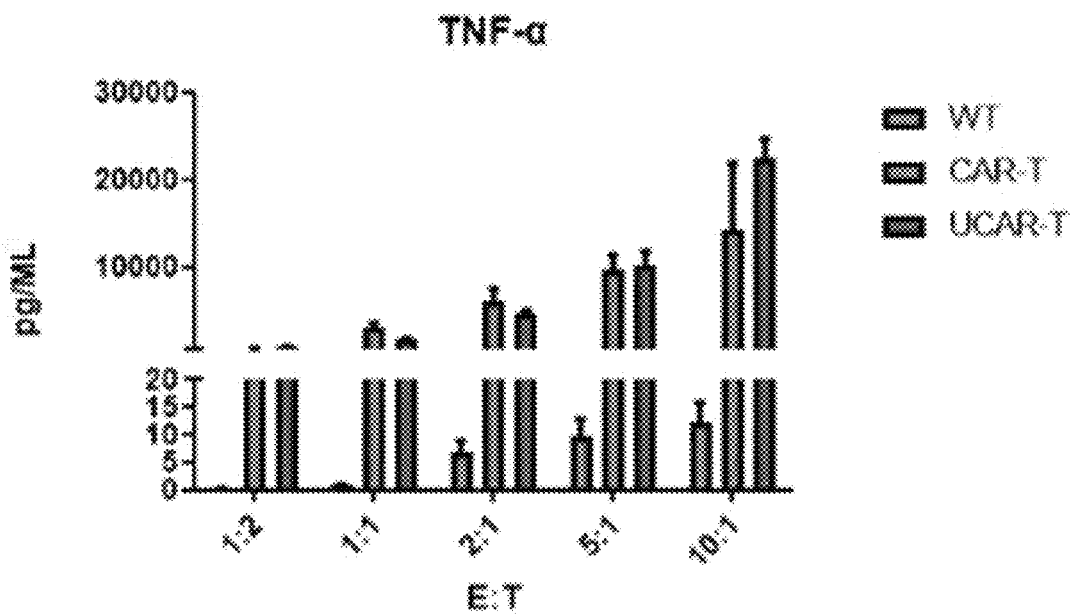

4.2 Cytokine Secretion Assay of Anti-B7H3 UCAR-T Cells Co-Cultured with Target Cells The supernatant of the co-culture system described above was collected, and the cytokine secretion level was assayed. Analysis of results (FIGS. 6A-6C): anti-B7H3 CAR-T and anti-B7H3 UCAR-T can be significantly activated and secrete IL-2, IFN-γ, and TNF-α cytokines in large quantities.

Example 5. In Vivo Anti-Tumor Effect of Anti-B7H3 UCAR-T Cells

NSG mice aged 8-10 weeks were injected subcutaneously with tumor cells PANC-I-Luciferase-GFP (5×106) and divided into three groups of 5 mice per group, and the tumor formation time was generally 2-4 weeks. 5E6 anti-B7H3 UCAR-T cells, anti-B7H3 CAR-T cells, and T cells without gene knockout were separately injected intratumorally into each group of mice by single-point injection with an injection volume of 50 µL. Tumor regression in mice was monitored by luciferase.

Figure 7:
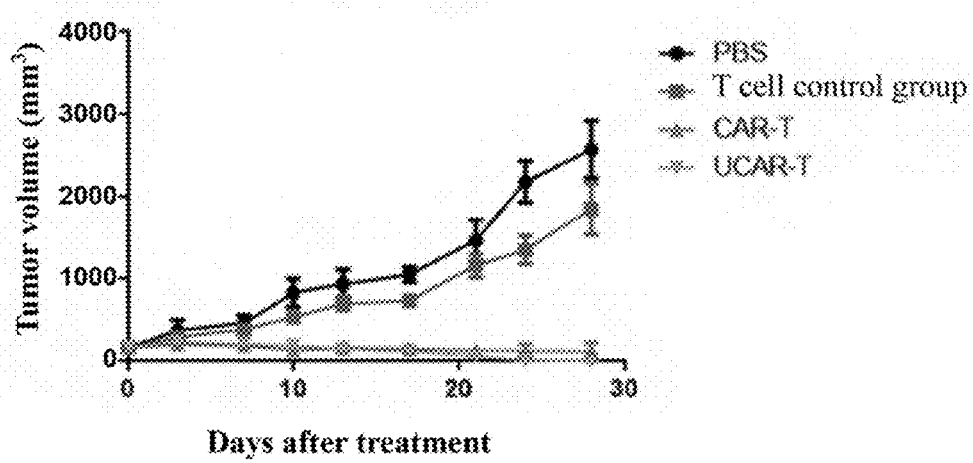
FIG. 7 shows an in vivo anti-tumor effect of the anti-B7H3 UCAR-T cells described in the present application.

Analysis of results (FIG. 7): the tumor growth rate of the mice reinfused with the anti-B7H3 UCAR-T cells was significantly slowed down, and both anti-B7H3 CAR-T and anti-B7H3 UCAR-T show excellent anti-tumor effects.

Example 6. In Vivo Half-Life Assay of Anti-B7H3 UCAR-T Cells 15 humanized immune system mice (hHSC-NCG) were prepared and divided into 3 groups. Cells were prepared as follows: an experimental group: anti-B7H3 UCAR-T cells (TRAC+HLA-A02 knocked out); control group 1: anti-B7H3 CAR-T; and control group 2: anti-B7H3 UCAR-T cells (TRAC+B2M knocked out). Each mouse was injected with 1×107 cells, and blood was collected at different time points: D0, 2 h, D3, D7, D14, D21, D28, D35, D42, D49, D56, and D60. Genomes in blood samples at different time points were extracted, and copy/ng genome DNA was calculated by QPCR absolute quantification method. UCAR-T cells harvested on day 14 were used as a positive control, and DEPC water was used as a negative control.

Analysis of results: the anti-B7H3 UCAR-T cells (TRAC+HLA-A02 knocked out) survive in mice for the longest time.

Example 7. In Vitro Safety Validation of Universal T Cells (1) GVHD response: T cells with double knockout of TRAC and HLA-A and T cells without gene knockout were prepared, allogeneic PBMCs were irradiated, 2 groups of prepared cells were stimulated separately, and IFN-γ levels were assayed.

Analysis of results: the T cell group with double knockout of TRAC and HLA-A had very low IFN-γ secretion level, indicating that the knockout of TRAC reduces the GVHD response.

(2) Allogeneic response: after the allogeneic PBMCs were stimulated and irradiated, 2 groups of cells were assayed for the IFN-γ level.

Analysis of results: the T cell group with double knockout of TRAC and HLA-A had very low IFN-γ secretion level, indicating that the knockout of HLA-A reduces the allogeneic response.

Example 8. In Vivo Safety Validation of Universal T Cells

Experimental group: $5×10^6$ TCR-HLA-A-double negative anti-B7H3 UCAR-T cells and $5×10^6$ allogeneic T cells were co-injected into NSG mice.

Control group: $5×10^6$ TCR-B7H3 UCAR-T cells and $5×10^6$ allogeneic T cells were injected into NSG mice.

Each group contained 5 NSG mice.

(1) GVHD response: according to clinical criteria, such as survival rate, coat texture, skin integrity, and the like, graft versus host response was observed. Assay of cytokines: peripheral blood serum was collected to assay the levels of cytokines such as IL6, IL-2, TNF-α, IFN-γ, and the like. The blood collection time points were as follows: 24 h, D3, D7, D14, D28, and 2 M before reinfusion. Assay of visceral lesion: at the end of the observation period (about 2 months), spleen, liver, skin, gastrointestinal tract, lung, and kidney of the mice were collected for HE section staining analysis.

Analysis of results: of 5 mice injected with untreated T cells, 4 mice developed lethal xenograft versus host disease (GVHD) within 2 months after injection. None of the mice receiving cells with double knockout of TRAC and HLA-A developed GVHD; the T cell group with double knockout of TRAC and HLA-A had very low secretion levels of cytokines such as IL6, IL-2, TNF-α, and IFN-γ; moreover, different organs in the mice were morphologically normal, indicating that the GVHD response in the T cell group with double knockout of TRAC and HLA-A is greatly reduced.

(2) Allogeneic response: CAR-T cells with double knockout of TRAC and HLA-A were prepared, and $1×10^7$ TCR-HLA-A-double-knockout CAR-T cells and $2×10^6$ allogeneic T cells were co-injected into NSG mice. Control group: $1×10^7$ TCR⁻CAR-T cells were injected into NSG mice.

Blood was collected at different time points to determine CAR copy number. The changes in the copy number were compared for both groups of CARs. The time points were as follows: D1, D5, D7, D10, D14, D21, and D28.

Figure 8A:
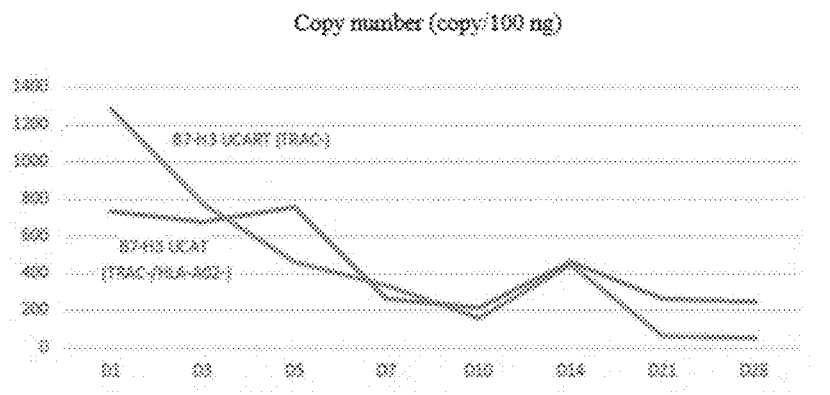
FIGS. 8A-8B show in vivo GVHD and rejection response results for targeting the anti-B7H3 UCAR-T cells described in the present application.
Figure 8B:
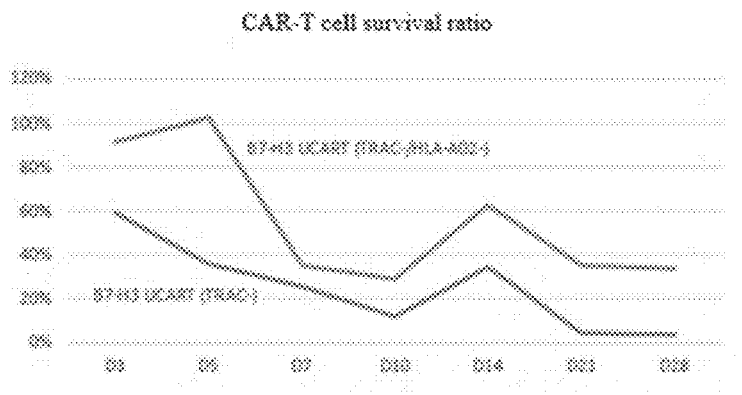

Conclusion: on D21, the rejection response of the mice in the control group was significant, and the copy number was basically undetectable. However, the copy number of the experimental group was still at a relatively stable level, indicating that the rejection response is significantly weakened; the survival time of the cells in the experimental group was prolonged in the mice, indicating that the rejection response in the CAR-T cell group with double knockout of TRAC and HLA-A is greatly reduced (see FIGS. 8A-8B).

Example 9. Safety Analysis of Gene Editing

T cells with double knockout of TRAC and HLA-A and T cells without gene knockout were prepared, and after the assay of knockout efficiency, the following analyses were performed:

(1) Off-target:

Control group: transgenic CAS9+ODN tag

Experimental group: transgenic CAS9+sgRNA (TRAC+HLA-A)+ODN tag

On-target and off-target-WGS (whole genome sequencing): on D14, $1×10^6$ of T cells without gene knockout and T cells with double knockout of TRAC and HLA-A were each collected and sent to Suzhou Genewiz Biological Technology Co., Ltd.

Figure 9:
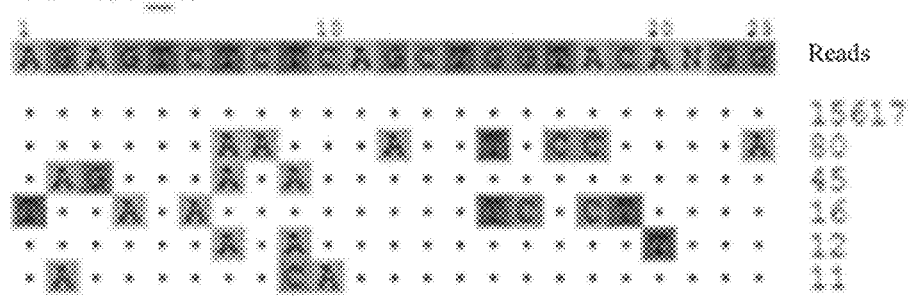
FIG. 9 shows off-target analysis of the anti-B7H3 UCAR-T cells described in the present application.
Figure 9:

Analysis of results: the off-target rate of the experimental group was very low, and the off-target was mainly concentrated among genes and on introns, so that the effect of the off-target on gene functions is not great (see FIG. 9).

(2) Chromosomal translocation: the qPCR method was used to quantify rearrangements that may occur when editing both TRAC and HLA loci simultaneously. The two translocations were labeled as TRAC:HLA and HLA:TRAC. Positive reference samples in the synthesized template plasmid were evaluated as assay controls. Amplified fragments on both sides of the target region of the HLA genome were used as internal controls. The genome DNA was extracted to perform real-time quantitative PCR, and the gene copy number of the genome DNA was calculated according to the standard curve and Cq value.

Figure 10:
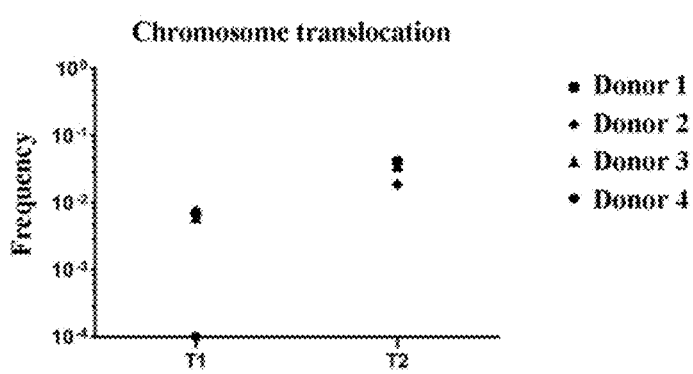
FIG. 10 shows chromosomal translocation analysis of the anti-B7H3 UCAR-T cells described in the present application.

Analysis of results: the T cells with double knockout (TRAC+HLA-A) were assayed for the occurrence of chromosomal translocation on D14 (harvest), and the assay results showed that the assay values for two types of translocation methods were closed to zero, suggesting that there is no rearrangement of the locus (see FIG. 10).

(3) Karyotyping: $1×10^6$ of T cells without gene knockout and T cells with double knockout of TRAC and HLA-A, which had a confluence of 70%-80%, were each put into two T25 bottles. The bottles were filled with a culture medium, covered with a fully sealed lid, wrapped with a sealing film, and sent to Zhejiang Ruyao Biotech Co., Ltd. for assay.

Figure 11:
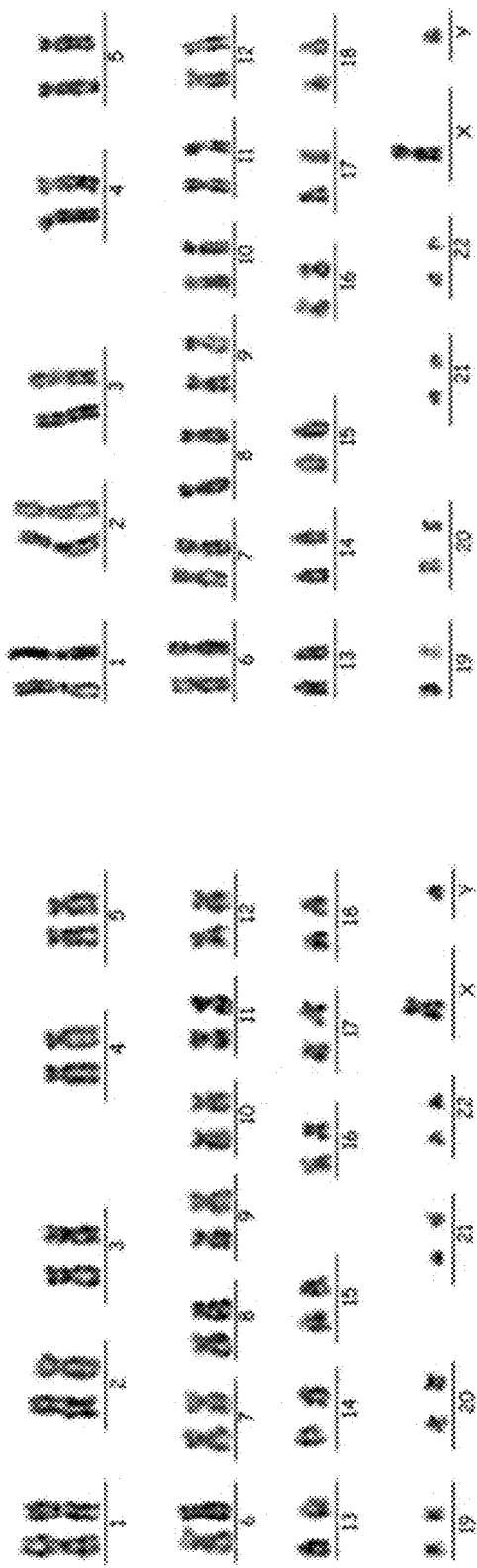
FIG. 11 shows karyotype analysis of the anti-B7H3 UCAR-T cells described in the present application.

Analysis of results: compared with the control group, the experimental group was normal in the karyotype (see FIG. 11).

(4) Cas9 protein residue: when the cells were prepared, 1×10⁶ cells at three time points, before knockout, after knockout, and before harvest, were separately collected for lysis, then a protein quantification kit (NOVATEINBIO, Catalog No. NB-E1372PR) was used for quantification, and each group of samples were adjusted to be 2 μg of the same sample loading amount and were assayed by a CRISPR/Cas9 protein ELISA kit according to the instruction. The Cas9 protein in the sample was firmly and stably attached to a test paper hole. The bound Cas9 protein was then recognized using an assay antibody and then developed with a developing agent. The Cas9 ratio was directly proportional to the absorbance, and absolute amounts of Cas9 protein were quantified by comparison to Cas9 control samples.

Figure 12:
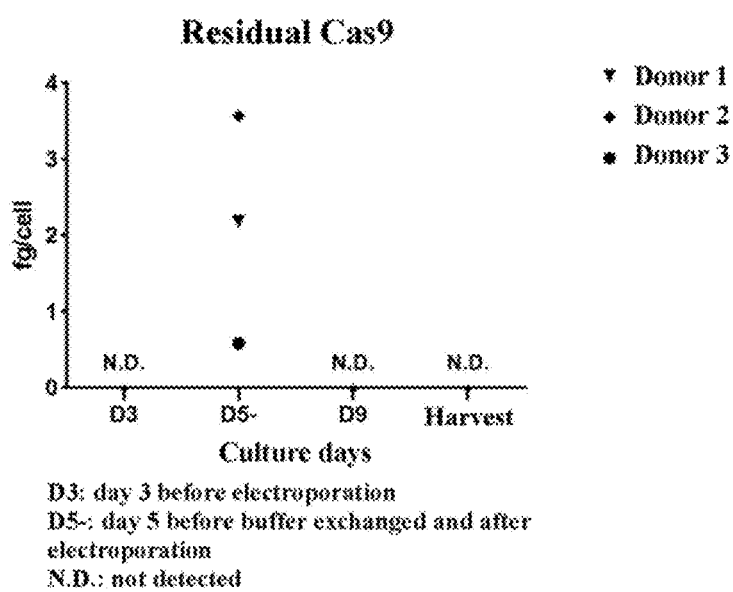
FIG. 12 shows residual Cas9 analysis of the anti-B7H3 UCAR-T cells described in the present application.

Analysis of results: the T cells with double knockout (TRAC+HLA-A) were assayed for the residue of spCas9 at four time points, before electroporation (D3), before buffer exchange and after electroporation (D5), D9, and D14 (harvest). The residues were not detected at all three time points except for the assay of trace residue before buffer exchange and after electroporation (D5) (see FIG. 12).

Example 10. Preparation of T Cells with Single-Gene Knockout

RNP complexes were transferred to the activated T cells prepared in Example 2 by electroporation using an electroporation kit (purchased from LONZA, Catalog No. V4XXP-3024). A culture medium (X-VIVO15 culture medium+10% FBS+IL2 (200 U/mL)+IL7 (10 ng/mL)+IL15 (5 ng/mL)) was pre-heated for 30 min in advance in a well plate. An electroporation buffer was prepared according to a ratio of Nucleofector Solution:Supplement=82:18. Preparation of RNP complexes: the sgRNA sequence of TRAC was Sg9 (set forth in SEQ ID NO: 157), and the sgRNA sequence of HLA-A was HLA-A02 Sg2 (set forth in SEQ ID NO: 173), HLA-A02 Sg5 (set forth in SEQ ID NO: 174), HLA-A11 Sg21 (set forth in SEQ ID NO: 204), or HLA-A11 Rsg2 (set forth in SEQ ID NO: 203). 20 μg of sgRNA was first added into a PCR tube (without RNase), 10 μg of Cas9 protein (purchased from Thermo, Catalog No. A36499) was then added, and after being mixed gently, the mixture was incubated at room temperature for 12 min. The activated T cells cultured in Example 2 were counted and centrifuged for 8 min at 300 g, and the supernatant was discarded. PBS was added to resuspend the cells, 1E7 cells were pipetted and centrifuged again for 8 min at 300 g, and the supernatant was discarded. The cells were resuspended in 100 μL of the prepared electroporation buffer. The incubated RNP complexes were added to the cell suspension described above. The mixture was gently mixed and gently transferred to an electroporation cuvette. The electroporation cuvette was placed on a Lonza-4D electroporation apparatus and subjected to electroporation using an EO-115 electroporation program. A pre-heated culture medium was added into the electroporation cuvette, and the cells were transferred into the pre-heated culture medium in the well plate by using a matched pipette and then placed in an incubator with 5% $CO_2$ at 37° C.

Example 11. Comparison of Gene Knockout Efficiency Assay Methods (1) Sanger Sequencing Assay The cells were counted. 3×10⁴ to 5×10⁴ cells were centrifuged for 5 min at 2000 r/min, and the supernatant was discarded as much as possible. 20 μL of DE lysis buffer was added into each tube. The lysed cells were added into a PCR tube, centrifuged instantaneously, and then placed into a PCR apparatus with the following conditions: 65° C. for 30 min, 4° C. for 30 s, 95° C. for 2 min, and 16° C. for infinite time. PCR was performed by using primer pairs TRAC-For/TRAC-Rev or HLA-A For/HLA-A Rev, and the lysed product was used as a template. The PCR product was sent to Genewiz for Sanger sequencing. After obtaining the Sanger sequencing results, the editing site and the editing efficiency were predicted with the EditR editor on the website: https://moriaritylab.shinyapps.io/editr_v10/.

(2) TA Cloning Sequencing Assay

The PCR product was purified using AxyPrep™ PCR product cleaning kit (purchased from AXYGEN), and then a sticky end was added to the purified PCR product using a kit (DNA A-Tailing Kit, purchased from TaKaRa). The product was ligated to T vector (pMDTM19-T Vector Cloning Kit, purchased from TaKaRa) by a DNA Ligation Kit Ver2.1 (purchased from TaKaRa), and the ligated product was transformed into competent cells (DH5 alpha). The cells were coated on an LB plate containing ampicillin resistance, and the plate was incubated in an incubator at 37° C. for about 12 h. Subsequently, a single colony was picked, and the single colony was sent to Genewiz for sequencing. Knockout efficiency=number of mutated clones/total clones.

(3) Cell Counting by Flow Cytometry

10E5 to 10E8 cells were centrifuged for 5 min at 2000 rpm, and the supernatant was discarded. 100 μL of PBS buffer was added to each tube to resuspend the cells, and 5 μL of anti-human AB TCR-APC antibody (purchased from eBioscience), 5 μL of HLA-A02 monoclonal antibody (BB7.2), APC, and eBioscince™ antibody (purchased from Invitrogen) were added. The mixture was mixed uniformly and incubated at room temperature for 10 min. After being centrifuged for 5 min at 2000 rpm, the cells were washed 2 times with the PBS buffer, resuspended, and assayed by a BD FACSAria flow cytometer. The positive expression rates of TCR and HLA-A02 on the cell surface could be obtained. Knockout efficiency=(A−B)/A×100%, wherein A was the positive expression rate of the control group; B was the positive expression rate of the knockout group.

Figure 13:
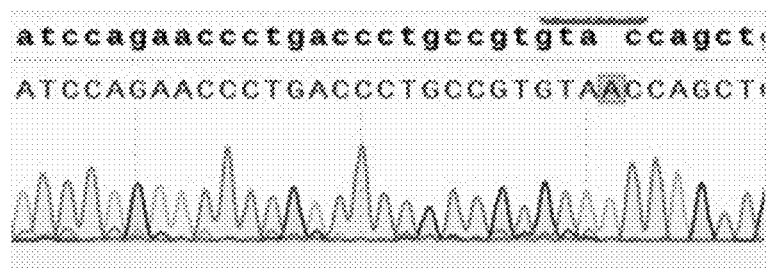
FIG. 13 shows Sanger sequencing results of TRAC gene after Sg9RNA editing in the present application, FIG.13 comprises nucleotide sequences set forth in SEQ ID NO: 217 (line 1) and SEQ ID NO: 218 (line 2)

Three assay results of TRAC single-gene knockout are shown in FIGS. 13 to 15, and calculation results of knockout efficiency are shown in Table 2. The three assay methods were basically the same, and the editing efficiency was assayed only by Sanger sequencing in subsequent experiments.

TABLE 2

Assay method results of gene knockout efficiency

| Target gene | sgRNA | Assay method | Knockout efficiency % |
|---|---|---|---|
| TRAC | Sg9 | Sanger sequencing | 90 |
|  |  | TA cloning sequencing | 95 |
|  |  | Flow cytometry | 93 |

The results of the Sanger sequencing method for HLA-A02 gene editing are shown in FIGS. 16-17, and the editing efficiencies are both 90%; the results of the Sanger sequencing method for HLA-All gene editing are shown in FIGS. 18-19.

Example 12. Preparation of T Cells with Double-Gene Knockout of TRAC Gene and HLA-A Gene RNP complexes were transferred to the activated T cells prepared in Example 2 by electroporation using an electroporation kit (purchased from LONZA, Catalog No. V4XXP-3024). A culture medium (X-VIVO15 culture medium+10% FBS+IL2 (200 U/mL)+IL7 (10 ng/mL)+IL15 (5 ng/mL)) was pre-heated for 30 min in advance in a well plate. An electroporation buffer was prepared according to a ratio of Nucleofector Solution: Supplement=82:18. Preparation of RNP complexes: 20 μg of TRAC sgRNA (TRAC Sg9) and 20 μg of HLA-A sgRNA (HLA-A02 Sg2, HLA-A02 Sg5, HLA-A11 sg21, or sgRNAs targeting HLA-A*24: 02:01, HLA-A*30:01:01:01, HLA-A*33:01:01:01, HLA-A*03:01:01:01, HLA-A*01:01:01:01, or HLA-A*26:01:01:01) were separately added to PCR tubes (without RNA), 10 μg of Cas9 protein (purchased from Thermo, Catalog No. A36499) were added to each tube, and the tubes were mixed gently and incubated at room temperature for 12 min. The activated T cells cultured in Example 2 were counted and centrifuged for 8 min at 300 g, and the supernatant was discarded. PBS was added to resuspend the cells, 1E7 cells were pipetted and centrifuged again for 8 min at 300 g, and the supernatant was discarded. The cells were resuspended in 100 μL of the prepared electroporation buffer. The incubated RNP complexes of TRAC and HLA-A were added to the cell suspension described above. The mixture was gently mixed and gently transferred to an electroporation cuvette. The electroporation cuvette was placed on a Lonza-4D electroporation apparatus and subjected to electroporation using an EO-115 electroporation program. A pre-heated culture medium was added into the electroporation cuvette, and the cells were transferred into the pre-heated culture medium in the well plate by using a matched pipette and then placed in an incubator with 5% $CO_2$ at 37° C.

Double-gene knockout efficiency was assayed by sequencing, and TRAC-negative and HLA-A-negative T cells with double-gene knockout efficiency of not less than 80% could be obtained. The results are shown in FIGS. 20-21. FIG. 20A shows the results of HLA-A02 knockout using HLA-A02 Sg5, wherein the upper row shows the results of the control group (i.e., HLA-A02 Sg5 was not used for knockout); the next row shows the results of simultaneous knockout of HLA-A02 and TRAC. FIG. 20B shows the results of TRAC knockout using TRAC Sg9, wherein the upper row shows the results of the control group (i.e., TRAC Sg9 was not used for knockout); the next row shows the results of simultaneous knockout of HLA-A02 and TRAC. FIGS. 21A-21B show the knockout at protein levels after the knockout of HLA-A02 and TRAC, wherein NEG refers to a negative control, WT refers to the absence of any knockouts, and TRAC+HLA-A double knockout refers to the results of simultaneous knockout of HLA-A02 and TRAC.

Example 13. Differences in Expression of TRAC, HLA-A, B2M, and CIITA Genes in T Cells with Double-Gene Knockout and Corresponding Genes in Corresponding Cells (1) The activated T cells prepared in Example 2 were used and divided into two groups. One was used as a control, and the other was prepared into T cells with double-gene knockout of TRAC gene and HLA-A gene according to the method in Example 5. Sanger sequencing was performed according to the method in step (1) of Example 4. The cells with double-gene knockout of TRAC and HLA-A were obtained according to the sequencing result. The prepared T cells with double-gene knockout were incubated with corresponding TRAC and HLA-A antibodies, and a cell strain with double-gene knockout was obtained by flow cytometry sorting or magnetic bead sorting.

(2) A change in mRNA expression level in the T cells with double-gene knockout was assayed compared to the control group. RNA was extracted using an RNA extraction kit (purchased from QIAGEN, Catalog No. 74004), and reverse transcription was performed on RNA using a reverse transcription kit (purchased from Applied Biosystems, Catalog No. 4368814) to obtain cDNA. Quantitative PCR assay was performed using the cDNA as a template.

(3) A change in protein expression level in the T cells with double-gene knockout was assayed compared to the control group. Proteins were extracted using a whole protein extraction reagent (purchased from Thermo Scientific, Catalog No. 87787), and the protein expression level was assayed by Western Blot method or flow cytometry using TRAC antibody (purchased from eBioscience, Catalog No. 17-9986-42), HLA-A antibody (purchased from Merck, Catalog No. 17-9876-41), B2M antibody (purchased from Invitrogen, Catalog No. A15770), and CIITA antibody (purchased from OriGene, Catalog No. CF812200).

The Sanger sequencing assay found that the nucleotide sequence of TRAC and/or HLA-A genes in the T cells with double-gene knockout is changed relative to the control group; the quantitative PCR showed that the mRNA expression level of TRAC and/or HLA-A genes is down-regulated in the T cells with double-gene knockout, but the mRNA expression level of B2M and/or CIITA genes is not down-regulated. FACS and Western Blot results showed that the protein expression amount in the T cells with double-gene knockout is down-regulated, and the protein expression amount of B2M and/or CIITA is not down-regulated.

The results are shown in FIGS. 22-23. FIG. 22 shows mRNA level determination of gene expression, and FIG. 22 shows mRNA levels of TRAC, HLA-A, B2M, and CIITA, wherein WT refers to a case without any knockout treatment, and the double-knockout group refers to a result of T cells with double-gene knockout of the TRAC gene and the HLA-A gene. FIG. 23 shows protein level determination of gene expression, wherein FIGS. 23A-23B show protein expression levels of B2M and CIITA, respectively; NEG refers to a negative control, WT refers to a case without any knockout treatment, and TRAC+HLA-A double knockout refers to the result of T cells with double-gene knockout of the TRAC gene and the HLA-A gene.

Example 14. Preparation of T Cells with Triple-Gene Knockout of TRAC Gene, HLA-A/B2M Gene, and CIITA Gene and Verification of Changes in Expression of Respective Three Genes (1) A control group, cells with triple-gene knockout of TRAC gene, HLA-A gene, and CIITA gene, and cells with triple-gene knockout of TRAC gene, B2M gene, and CIITA gene were prepared according to the method in step (1) of Example 13.

(2) Changes in protein expression levels were assayed by FACS and Western Blot methods according to the method in step (3) of Example 13.

The protein expression levels of TRAC, HLA-A, and CHITA genes in the T cells with triple-gene knockout of TRAC, HLA-A, and CHITA were down-regulated relative to the cells in the control group; the protein expression levels of TRAC, B2M, and CIITA genes in the T cells with triple-gene knockout of TRAC, B2M, and CIITA were down-regulated relative to the cells in the control group.

(3) The knockout efficiencies of the cells with double-gene knockout in Example 13 and the two cells with triple-gene knockout in this example were assayed by flow cytometry using TRAC antibody (purchased from eBioscience, Catalog No. 17-9986-42), HLA-A antibody (purchased from Merck, Catalog No. 17-9876-41), and B2M antibody (purchased from Invitrogen, Catalog No. A15770), and the results showed that the efficiency of multiple gene knockout was achieved simultaneously at the single cell level, and that the efficiency of the double-gene knockout was significantly higher than that of the triple-gene knockout.

Figure 24A:
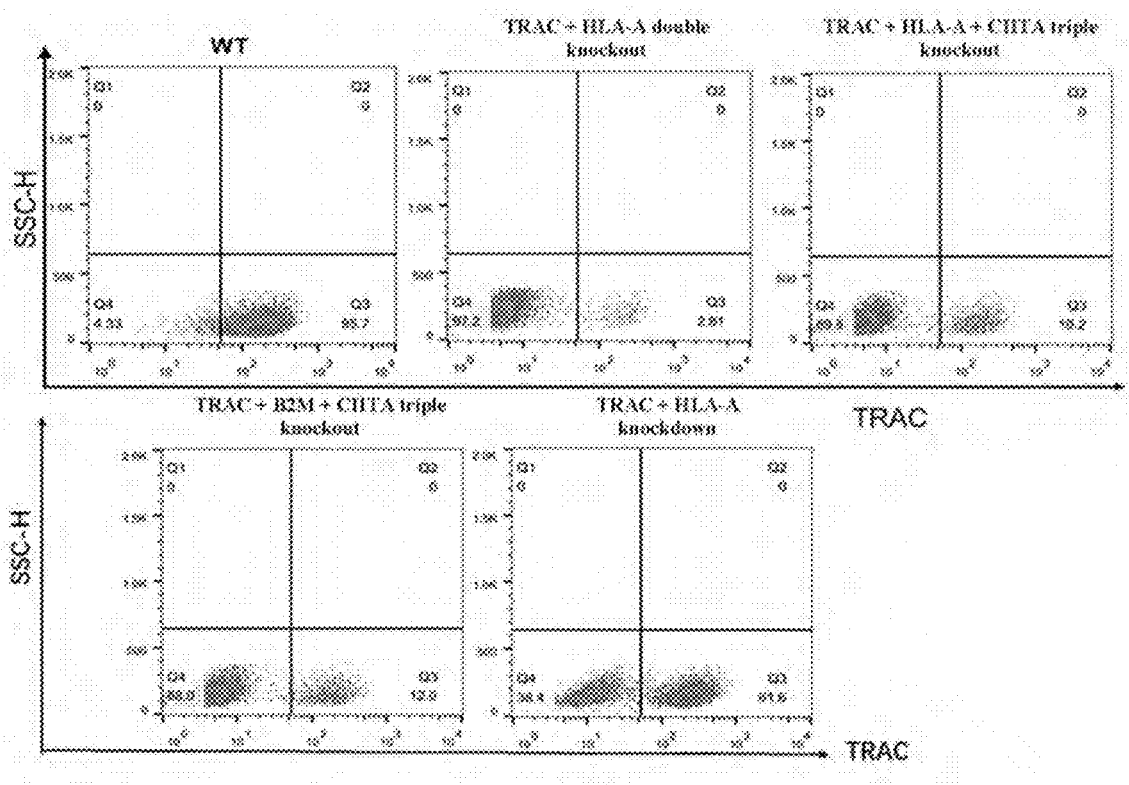
Figure 24B:
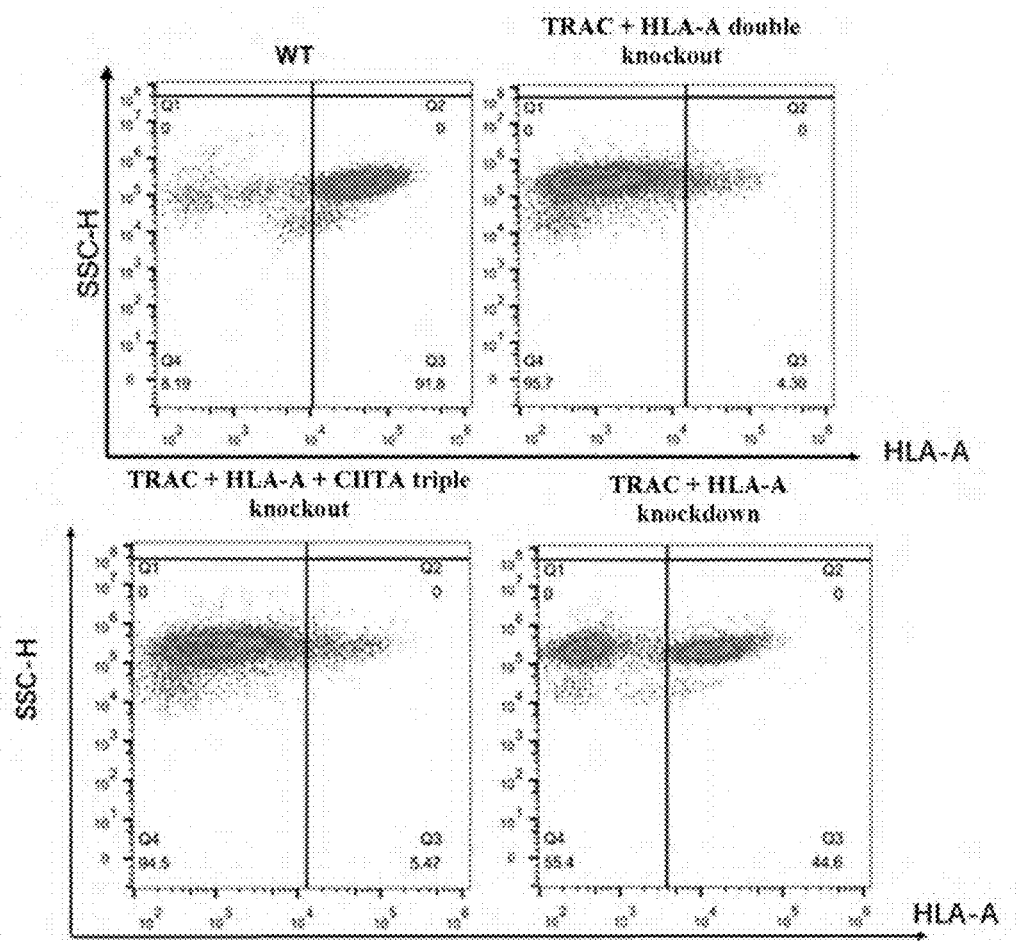
Figure 24C:
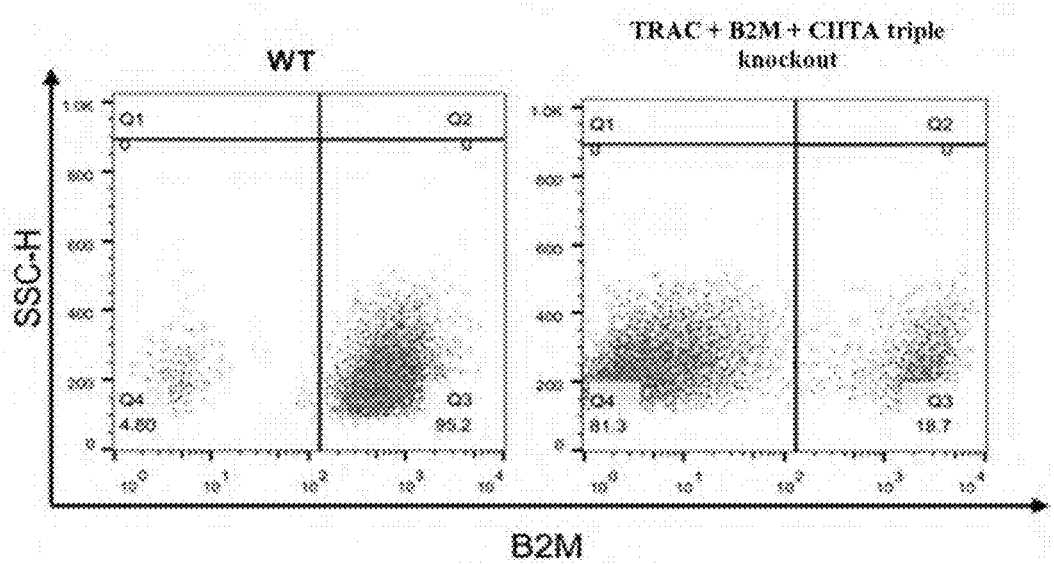
Figure 24D:
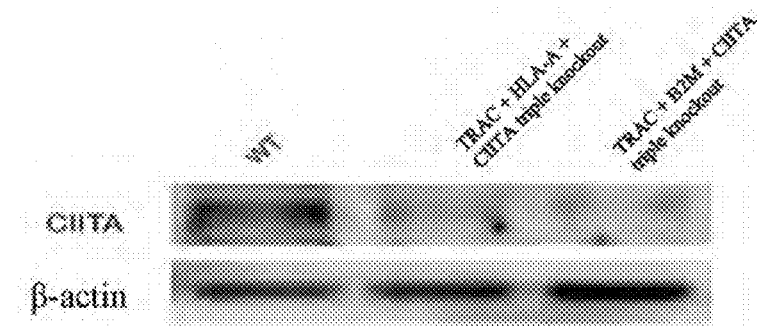

The results are shown in FIGS. 24A-24D. FIGS. 24A-24C show the knockout of TRAC, HLA-A and B2M at protein levels in sequence, wherein WT refers to a case without any knockout treatment, TRAC+HLA-A double knockout refers to the result of T cells with double-gene knockout of TRAC and HLA-A genes; TRAC+HLA-A+CIITA triple knockout refers to the result of T cells with triple-gene knockout of TRAC, HLA-A, and CIITA; TRAC+B2M+CIITA triple knockout refers to the result of T cells with triple-gene knockout of B2M, CIITA, and TRAC; and TRAC+HLA-A knockdown refers to the result of T cells with knockdown of TRAC and HLA-A genes prepared in Example 16. FIG. 24D shows the knockout of CIITA at the protein level.

The results in FIG. 24 showed that the protein levels of TRAC, HLA-A, CIITA, and B2M are down-regulated compared to the WT control group. Meanwhile, compared to TRAC+HLA-A+CIITA triple knockout or TRAC+B2M+CIITA triple knockout, the knockout efficiency of TRAC+HLA-A double knockout is higher.

Example 15. Design of Antisense RNA Sequence

The transcription RNA sequences of the corresponding genes (TRAC gene and HLA-A gene) were obtained by the database https://www.ncbi.nlm.nih.gov/ or www.ensembl.org/, and siRNA was designed with reference to the following principles:

Sequences of 50-100 nucleotides downstream of the start codon and 100 nucleotides upstream of the stop codon were avoided as possible; sequences with less than 30 nucleotides in length were selected; 4 or more consecutive identical bases were avoided; intron regions were avoided; repetitive sequences were avoided; single nucleotide polymorphism (SNP) sites were avoided; sequences had a GC content ranging 30% to 60%; sequence patterns AA ($N_{19}$), NA ($N_{21}$), or NAR ($N_{17}$) YNN were preferably selected, wherein A was adenosine, T was thymidine, R was adenosine or guanosine (purines), Y was thymidine or cytidine (pyrimidines), N was adenosine, thymidine, guanosine, or cytidine; homology comparison and analysis were performed on the selected sequences to avoid significant homology of the antisense RNA to other genes or sequences and the resulting off-target effects. The homology analysis was performed using NCBI Blast tool: Nucleotide-nucleotide BLAST (blastn), UCSC Blat tool, or Ensembl Blast.

The antisense RNA sequences obtained by design included HLA-A-homo-551, HLA-A-homo-NEG, TRAC-homo-375, and TRAC-homo-NEG.

Example 16. Preparation of T Cells with Knockdown of TRAC Gene and HLA-A Gene

Double-gene knockdown was performed using the antisense RNA designed in Example 15. A lentivirus comprising the antisense RNA sequences of the TRAC gene and HLA-A gene was prepared by a company (Genepharma). $CD3^+$ T cells were prepared according to the method in Example 2 (D0) and activated with CD3/CD28 antibody magnetic beads. The lentivirus carrying the antisense RNA sequences of the TRAC gene and HLA-A gene was transfected into the activated T cells (D1). On D2, the lentiviral vector was washed off, and the cells were continued to be cultured until D5. The T cells cultured until D5 were collected, and gene knockdown efficiency was assayed by quantitative PCR or Western Blot, etc. The obtained T cells were labeled with corresponding TRAC and HLA-A antibodies, and the T cells with knockdown of the TRAC gene and HLA-A gene could be obtained by flow cytometry sorting or magnetic bead sorting methods. The results showed that both the mRNA and protein expression levels of TRAC and HLA-A were down-regulated in the TRAC and HLA-A gene-knockdown group. FIGS. 25A-25B show the knockout of TRAC and HLA-A at mRNA levels in sequence, wherein WT refers to a case without any knockout treatment, and TRAC+HLA-A double knockout refers to the result of T cells with double-gene knockout of the TRAC gene and the HLA-A gene. Among these, the knockout level of TRAC and HLA-A at protein levels can be found in the results shown in FIG. 24.

Example 17. Difference in Activities of Different T Cells

The T cells without gene knockout, with double-gene knockout, with triple-gene knockout, and with double-gene knockdown in Examples 2, 12, 14, and 16 were prepared, and several T cell activities were compared. Each group of cells was counted and seeded in 24-well plates with $1 \times 10^6$ cells, and PHA (0.3 µg/mL) (ionomycin+) or 5 ng/mL PMA and 50 ng/mL ionomycin were added to the cells per well. The cells were cultured for another 5 h, and then the activation state of the cells were assayed using CD69 (early activated) (purchased from BD Biosciences, Catalog No. FN50) and CD137 (later stage) (purchased from BD Biosciences, Catalog No. 4B4-1) antibodies by flow cytometry. The results showed that the activities of the T cells with double-gene knockout and double-gene knockdown were superior to that of the T cells with triple-gene knockout.

The expression of CD69 and CD137 at protein levels is shown in FIGS. 26A-26B, respectively, wherein WT refers to a case without any knockout treatment, TRAC+HLA-A double knockout refers to the result of T cells with double-gene knockout of TRAC and HLA-A genes; TRAC+HLA-A+CIITA triple knockout refers to the result of T cells with triple-gene knockout of TRAC, HLA-A, and CIITA; TRAC+B2M+CIITA triple knockout refers to the result of T cells with triple-gene knockout of B2M, CIITA, and TRAC; and TRAC+HLA-A knockdown refers to the result of T cells with knockdown of TRAC and HLA-A genes prepared in Example 16.

Example 18. Difference in Reactivity of Different T Cells to Allogeneic NK Cells CFSE (Invitrogen, C34554) labeling was performed on the T cells without gene knockout, with double-gene knockout, with triple-gene knockout, and with double-gene knockdown in Examples 2, 12, 14, and 16. The cells were counted, and 1×10$^6$ cells were collected and co-cultured with NK cells (NK92MI) at a ratio of 1:1. After 24 h, the co-cultured cells were collected from each group, and the ratio of CFSE-positive cells in the mixed cells was determined by flow cytometry.

The results showed that the killing toxicity of the NK cells to the T cells with double-gene knockout and double-gene knockdown was lower than that of the T cells with triple-gene knockout. The results are shown in FIG. 27, wherein NK+T refers to a case where the NK cells were co-cultured with the T cells without any knockout treatment; NK+TRAC+HLA-A knockdown refers to a case where the NK cells were co-cultured with the resulting T cells with knockdown of the TRAC gene and HLA-A gene prepared in Example 16; NK+TRAC+HLA-A double knockout refers to a case where the NK cells were co-cultured with the T cells with double-gene knockout of the TRAC gene and HLA-A gene; NK+TRAC+HLA-A+CIITA triple knockout refers to a case where the NK cells were co-cultured with the T cells with triple-gene knockout of TRAC, HLA-A, and CIITA; NK+TRAC+B2M+CIITA triple knockout refers to a case where the NK cells were co-cultured with the T cells with triple-gene knockout of B2M, CIITA, and TRAC.

Example 19. Difference in Allogeneic Immune Rejection of Different T Cells

Peripheral blood originated from donor 1 was used to prepare T cells without gene knockout, with double-gene knockout, with triple-gene knockout, and with double-gene knockdown in Examples 2, 12, 14, and 16. Peripheral blood originated from donor 2 was used to prepare CD3$^+$ T cells. Each group of cells prepared from the peripheral blood of donor 1 was mixed with the CD3$^+$ T cells prepared from the peripheral blood of donor 2 according to Example 2 in an equal proportion. After 24 h, the expression level of IFN-γ in the cell mixture system was assayed. The results showed that the expression level of IFN-γ in the T-cell group with double-gene knockout was lower than that in the T-cell group with triple-gene knockout.

The results are shown in FIG. 28. WT refers to a case without any knockout treatment, TRAC+HLA-A double knockout refers to the result of T cells with double-gene knockout of TRAC and HLA-A genes; TRAC+HLA-A+CIITA triple knockout refers to the result of T cells with triple-gene knockout of TRAC, HLA-A, and CIITA; TRAC+B2M+CIITA triple knockout refers to the result of T cells with triple-gene knockout of B2M, CIITA, and TRAC; and TRAC+HLA-A knockdown refers to the result of T cells with knockdown of TRAC and HLA-A genes prepared in Example 16.

Example 20. Preparation of CAR-T Cells with Double-Gene Knockout of TRAC Gene and HLA-A Gene, CAR-T Cells with Triple-Gene Knockout of TRAC Gene, HLA-A Gene, and CIITA Gene, and CAR-T Cells with Knockout of TRAC Gene, B2M Gene, and CIITA Gene (1) CD3$^+$ T cells were obtained according to the method in Example 2 (D0) and activated with CD3/CD28 antibody magnetic beads. After activation, lentiviral vectors (lentiviruses comprising CD19-CAR, CD20-CAR, or BCMA-CAR) were transfected on D1, the lentiviral vectors were washed off on D2, CAR-positive T cells were sorted on D3, and the cells were continued to be cultured until D5.

(2) The CAR-T cells obtained on D5 were used as starting cells, and cells with double-gene knockout of the TRAC gene and HLA-A gene, CAR-T cells with triple-gene knockout of the TRAC gene, HLA-A gene, and CIITA gene, and CAR-T cells with triple-gene knockout of the TRAC gene, B2M gene, and CIITA gene were prepared according to the methods in Examples 12 and 14, respectively.

(3) The CAR-T cells with double-gene knockout and triple-gene knockout described above could be obtained by flow cytometry assay, wherein the yield of the CAR-T cells with double-gene knockout was higher than that of the CAR-T cells with triple-gene knockout.

Figure 29A:
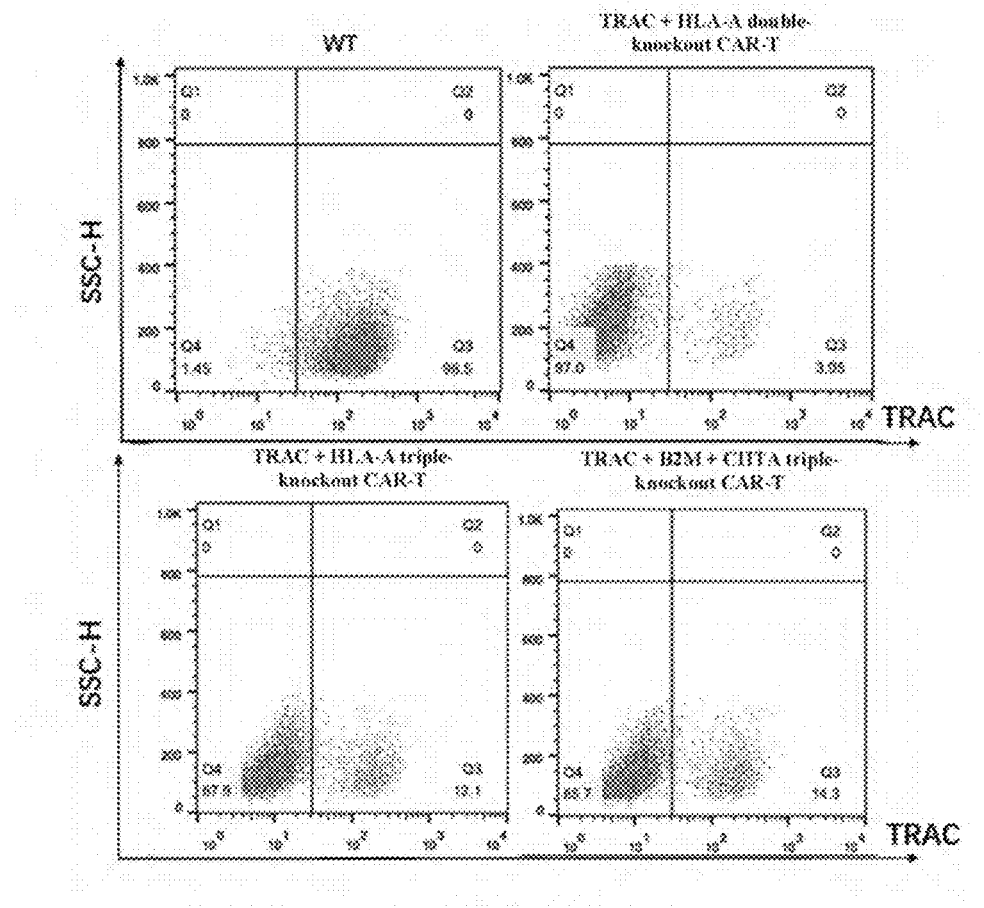
Figure 29B:
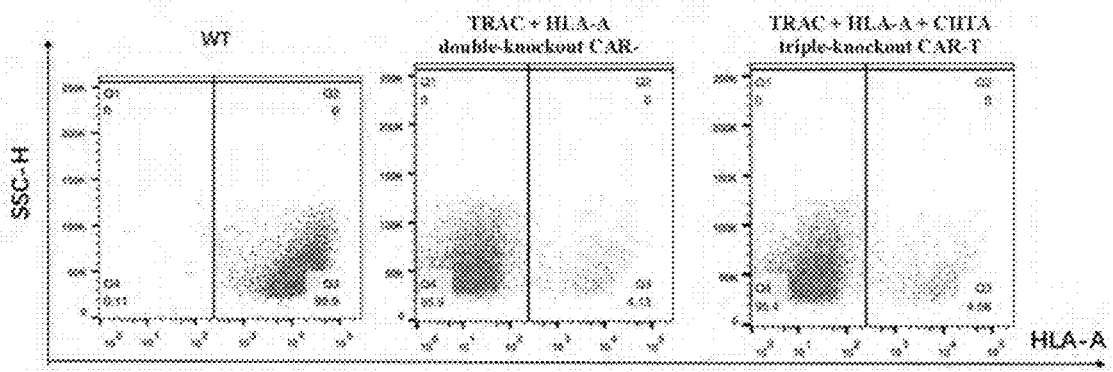
Figure 29C:
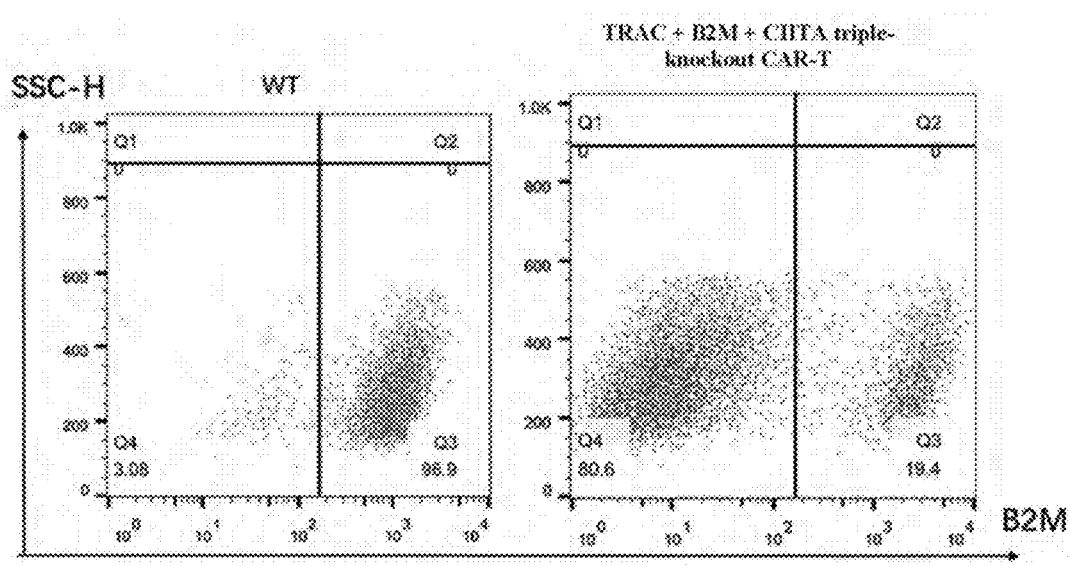
Figure 29D:
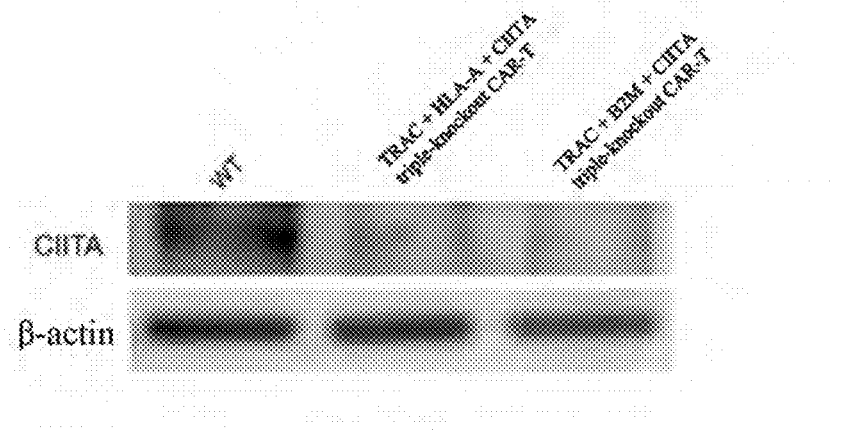

The results are shown in FIGS. 29A-29D. FIGS. 29A-29C show the knockout of TRAC, HLA-A and B2M at protein levels in sequence. FIG. 29D shows the knockout of CIITA at the protein level, wherein WT refers to a case without any knockout treatment, TRAC+HLA-A double knockout refers to the result of CAR-T cells with double-gene knockout of TRAC and HLA-A genes; TRAC+HLA-A+CIITA triple knockout refers to the result of CAR-T cells with triple-gene knockout of TRAC, HLA-A, and CIITA; TRAC+B2M+CIITA triple knockout refers to the result of CAR-T cells with triple-gene knockout of B2M, CIITA, and TRAC.

Among these, the transfection efficiency of CD19CAR is shown in FIGS. 30A-30B, wherein CAR30%+ represented the transfection efficiency of CD19 CAR.

FIG. 31 shows the amplification fold of different cells, wherein the CAR-T cells with double-gene knockout of the TRAC gene and HLA-A gene had the highest amplification fold.

Example 21. Anti-Tumor Effect of CAR-T Cells with Double-Gene Knockout of TRAC Gene and HLA-A Gene The CAR-T cells with double knockout of the TRAC gene and HLA-A gene (targeting CD19, CD20, or BCMA) were prepared in Example 21. Target cells expressing the luciferase gene (target gene-positive leukemia or lymphoma cell lines, such as Raji, Jurkat, MMIS, and the like) were seeded to a well plate. The CAR-T cells with double-gene knockout, CAR-T cells with triple-gene knockout, or T cells without gene knockout were added at different effector-to-target ratios (1:2.5, 1:1, 5:1, and 10:1), respectively. After 24 h of co-culture, the cells were transferred to an assay well plate, luciferase substrate was added, and fluorescence value was detected by a microplate reader. Killing efficiency=1−fluorescence value of T cells co-cultured with target cells/fluorescence value of target cells cultured alone.

The results showed that the CAR-T cells with double knockout of the TRAC gene and HLA-A gene had a significant killing effect on tumor cells.

FIG. 32 shows the killing effect on CD19 target cell Raji-Luciferase, wherein the CAR-T cells with double knockout of the TRAC gene and HLA-A gene exhibit the most significant killing effect. At each E/T ratio, the results corresponding to notes A-D were shown from left to right.

Example 22. Anti-Tumor Effect of CAR-T Cells with Double-Gene Knockout of TRAC Gene and HLA-A Gene NSG mice were injected with tumor cells intravenously. After the tumor was successfully established, the CAR-T cells with double-gene knockout of the TRAC gene and HLA-A gene, CAR-T cells with triple-gene knockout, and T cells without gene knockout were reinfused to the mice. The tumor volume of the mice was monitored.

The mice to which the CAR-T cells with double-gene knockout were reinfused exhibited a significantly slower growth rate of the tumor.

The results are shown in FIGS. 33-34, wherein FIG. 33 showed the administration mode in mice, i.v. represented intravenous injection, CAR-T cells represented CAR-T cells with double-gene knockout and CAR-T cells with triple-gene knockout expressing CD19 CAR. FIG. 34 showed the tumor volume in the mice after the CAR-T cells were administered, wherein FIG. 34 showed, from left column to right column, the tumor volume in the mice after normal saline, unmodified T cells, CD19 CAR-T cells with double-gene knockout of the TRAC gene and HLA-A gene, CD19 CAR-T cells with triple-gene knockout of TRAC, HLA-A, and CIITA, and CD19 CAR-T cells with triple-gene knockout of B2M, CIITA, and TRAC were separately administered in sequence. The results showed that the mice to which the CAR-T cells with double-gene knockout of the TRAC gene and HLA-A gene were reinfused exhibited a significantly slower growth rate of the tumor.

In summary:
1. The present application prepares a chimeric antigen receptor targeting B7H3, an antigen-binding domain of the recombinant receptor is derived from a nanoantibody, and the recombinant receptor has the characteristics of small molecular weight and stable structure.
2. The present application provides a lentiviral expression vector. pCDH-CMV-MCS-EF1-copGFP is used as a backbone, and an ampicillin resistance gene β-lactamase on the vector is replaced with aminoglycoside phosphotransferase derived from Tn5 to enable the vector to have kanamycin resistance; the CMV promoter and its adjacent downstream multiple cloning site, which are potentially threatening in vivo applications, are deleted; the copGFP gene that is started to express by the EF1 promoter in the original vector is deleted, a SalI enzyme digestion site is retained, and a SmaI enzyme digestion site is added to the 5' end of SalI for vector construction to form a final target vector.
3. The present application optimizes the protein-RNA complex electrotransfection technology. More than 90% of double-gene knockout efficiency in primary T cells is obtained.
4. In the present application, the donor source is based on HLA-B homozygotes that occur frequently in the population, and one of the alleles of HLA-B in the patient is consistent with the homozygotes in the donor, so that cells from these donors can cover a high number of patient populations, and the rejection response caused by HLA-B can be reduced.
5. According to the present application, HLA-A molecules highly related to rejection are screened out for knockout, and other HLA-I molecules are retained, so that the rejection of allogeneic cells is reduced, the complete knockout of HLA molecules and elimination of HLA molecules by NK cells are avoided, thereby greatly prolonging the half-life of allogeneic CAR-T cells in vivo.
6. The present application firstly constructs anti-B7H3-UCAR-T cells with highly efficient double knockout of TCR and HLA-A, achieves a safe shelf-ready-to-use therapeutic agent, improves the anti-tumor effect, and is used for treating diseases such as adrenocortical carcinoma, bladder cancer, breast cancer, cholangiocarcinoma, colorectal cancer, lymphoma, esophageal cancer, brain glioma, head and neck squamous cell carcinoma, kidney cancer, liver cancer, lung cancer, ovarian cancer, pancreatic cancer, prostate cancer, sarcoma, melanoma, gastric cancer, thymus cancer, and endometrial cancer.

The invention claimed is:

1. An antigen-binding polypeptide, binding B7H3, comprising an antibody heavy chain variable region (VH), wherein the VH comprises
   i) an HCDR1 comprising the amino acid sequence set forth in SEQ ID NO: 2, an HCDR2 comprising the amino acid sequence set forth in SEQ ID NO: 5, and an HCDR3 comprising the amino acid sequence set forth in SEQ ID NO: 8; or
   ii) an HCDR1 comprising the amino acid sequence set forth in SEQ ID NO: 3, an HCDR2comprising the amino acid sequence set forth in SEQ ID NO: 6, and an HCDR3 comprising the amino acid sequence set forth in SEQ ID NO: 9.

2. The antigen-binding polypeptide according to claim 1, wherein the VH comprises an amino acid sequence set forth in SEQ ID NO: 26, SEQ ID NO: 27, SEQ ID NO: 28, or SEQ ID NO: 29.

3. The antigen-binding polypeptide according to claim 1, wherein the antigen-binding polypeptide comprises an antibody or an antigen-binding fragment thereof.

4. The antigen-binding polypeptide according to claim 3, wherein the antibody is a single-domain antibody.

5. A chimeric antigen receptor (CAR) comprising a B7H3-targeting moiety, wherein the B7H3-targeting moiety comprises the antigen-binding polypeptide according to claim 1.

6. The chimeric antigen receptor according to claim 5, comprising a transmembrane domain, wherein the transmembrane domain comprises a transmembrane domain derived from one or more proteins selected from the group consisting of: CD8A, CD8B, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4 (CD244), FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, and SLAM.

7. The chimeric antigen receptor according to claim 5, comprising an intracellular co-stimulatory signaling domain, wherein the intracellular co-stimulatory signaling domain comprises an intracellular co-stimulatory signaling domain derived from one or more proteins selected from the group consisting of: CD28, CD137, CD27, CD2, CD7, CD8A, CD8B, OX40, CD226, DR3, SLAM, CDS, ICAM-1, NKG2D, NKG2C, B7H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, and MyD88.

8. The chimeric antigen receptor according to claim 5, comprising an intracellular signaling domain, wherein the intracellular signaling domain comprises an intracellular signaling domain derived from one or more proteins selected from the group consisting of: CD3ζ, CD3δ, CD3γ, CD3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

9. The chimeric antigen receptor according to claim 6, comprising a hinge region between the targeting moiety and the transmembrane domain, wherein the hinge region comprises a hinge region derived from one or more proteins selected from the group consisting of: CD28, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, and LIGHT.

10. The chimeric antigen receptor according to claim 5, wherein a non-targeting moiety of the chimeric antigen receptor comprises a transmembrane domain of CD8A molecule, a hinge region of CD8A, an intracellular co-stimulatory signaling domain of 4-1BB, and an intracellular signaling domain of CD3ζ.

11. An immune effector cell expressing the CAR according to claim 5.

12. The immune effector cell according to claim 11, wherein the immune effector cell is an autologous or immune effector cell.

13. The immune effector cell according to claim 11 wherein the immune effector cell is a modified immune effector cell, and wherein the modified immune effector cell comprises a cell that reduces immune rejection caused by allogeneic cell therapy.

14. The immune effector cell according to claim 13, wherein functions of a T cell antigen receptor (TCR) and major histocompatibility complexes (MHC) in the modified immune effector cell are inhibited in the T cell.

15. The immune effector cell according to claim 13, wherein a modification comprises down-regulation of an expression and/or activity of one or more of immune rejection-related genes, wherein the immune rejection-related gene is selected from one or more of the following groups: TRAC, TRBC, HLA-A, HLA-B, B2M, and CIITA.

16. The immune effector cell according to claim 15, wherein the expression and/or activity of the TRAC gene and the HLA-A gene in the modified immune effector cell is down-regulated as compared to a corresponding unmodified cell.

17. The immune effector cell according to claim 13, wherein a modification comprises administering to the immune effector cell one or more substances selected from the group consisting of: antisense RNA, siRNA, shRNA, and a CRISPR/Cas9 system.

18. The immune effector cell according to claim 17, wherein a modification further comprises administering to the immune effector cell sgRNA targeting an exon portion of the TRAC gene.

19. The immune effector cell according to claim 18, wherein the sgRNA targeting the exon portion of the TRAC gene comprises a nucleotide sequence set forth in any one of SEQ ID NO: 157 to SEQ ID NO: 171.

20. The immune effector cell according to claim 17, wherein a modification comprises administering to the immune effector cell sgRNA targeting an exon portion of the HLA-A gene.

21. The immune effector cell according to claim 20, wherein the sgRNA targeting the exon portion of the HLA-A gene comprises a nucleotide sequence set forth in any one of SEQ ID NO: 172 to SEQ ID NO: 212.

22. The immune effector cell according to claim 11, wherein the immune effector cell is an HLA-B homozygous cell.

23. The immune effector cell according to claim 11, wherein the immune effector cell is an HLA-A homozygous cell.

24. A pharmaceutical composition comprising the antigen-binding polypeptide according to claim 1, and optionally a pharmaceutically acceptable carrier.

25. A pharmaceutical composition comprising the chimeric antigen receptor according to claim 5 and optionally a pharmaceutically acceptable carrier.

26. A pharmaceutical composition comprising the immune effector cell according to claim 11, and optionally a pharmaceutically acceptable carrier.

* * * * *

```
                    SEQUENCE LISTING

<160> NUMBER OF SEQ ID NOS: 240

<210> SEQ ID NO 1
<211> LENGTH: 8
<212> TYPE: PRT
<213> ORGANISM: Artificial Sequence
<220> FEATURE:
<223> OTHER INFORMATION: 1A5 HCDR1, hu1A5 HCDR1; 1G7 HCDR1, hu1G7 HCDR1
<220> FEATURE:
<221> NAME/KEY: MISC_FEATURE
<222> LOCATION: (8)..(8)
<223> OTHER INFORMATION: Xaa = Ala or Ser
<220> FEATURE:
<221> NAME/KEY: MISC_FEATURE
<222> LOCATION: (8)..(8)
<223> OTHER INFORMATION: Xaa = Ala or Ser

<400> SEQUENCE: 1

Gly Arg Ile Phe Ser Asn Tyr Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: 1G7 HCDR1, hu1G7 HCDR1

<400> SEQUENCE: 2
```

```
Gly Arg Ile Phe Ser Asn Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: 1A5 HCDR1, hu1A5 HCDR1

<400> SEQUENCE: 3

Gly Arg Ile Phe Ser Asn Tyr Ser
1               5

<210> SEQ ID NO 4
<211> LENGTH: 8
<212> TYPE: PRT
<213> ORGANISM: Artificial Sequence
<220> FEATURE:
<223> OTHER INFORMATION: 1G7 HCDR2, hu1G7 HCDR2; 1A5 HCDR2, hu1A5 HCDR2
<220> FEATURE:
<221> NAME/KEY: MISC_FEATURE
<222> LOCATION: (3)..(3)
<223> OTHER INFORMATION: Xaa = Gly or Trp
<220> FEATURE:
<221> NAME/KEY: MISC_FEATURE
<222> LOCATION: (8)..(8)
<223> OTHER INFORMATION: Xaa = Thr or Val

<400> SEQUENCE: 4

Ile Ile Xaa Ser Thr Gly Thr Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: 1G7 HCDR2, hu1G7 HCDR2

<400> SEQUENCE: 5

Ile Ile Gly Ser Thr Gly Thr Val
1               5

<210> SEQ ID NO 6
<211> LENGTH: 8
<212> TYPE: PRT
<213> ORGANISM: Artificial Sequence
<220> FEATURE:
<223> OTHER INFORMATION: 1A5 HCDR2, hu1A5 HCDR2

<400> SEQUENCE: 6

Ile Ile Trp Ser Thr Gly Thr Thr
1               5

<210> SEQ ID NO 7
<211> LENGTH: 18
<212> TYPE: PRT
<213> ORGANISM: Artificial Sequence
<220> FEATURE:
<223> OTHER INFORMATION: 1G7 HCDR3, hu1G7 HCDR3; 1A5 HCDR3, hu1A5 HCDR3
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (17)..(17)
<223> OTHER INFORMATION: Xaa = Lys or Arg
```

```
<400> SEQUENCE: 7

Ala Ala Ser Phe Xaa Tyr Ser Gly Ile Tyr Gly Arg Glu Ala Asp Phe
1               5                   10                  15

Xaa Ser

<210> SEQ ID NO 8
<211> LENGTH: 18
<212> TYPE: PRT
<213> ORGANISM: Artificial Sequence
<220> FEATURE:
<223> OTHER INFORMATION: 1G7 HCDR3, hu1G7 HCDR3

<400> SEQUENCE: 8

Ala Ala Ser Phe Arg Tyr Ser Gly Ile Tyr Gly Arg Glu Ala Asp Phe
1               5                   10                  15

Val Ser

<210> SEQ ID NO 9
<211> LENGTH: 18
<212> TYPE: PRT
<213> ORGANISM: Artificial Sequence
<220> FEATURE:
<223> OTHER INFORMATION: 1A5 HCDR3, hu1A5 HCDR3

<400> SEQUENCE: 9

Ala Ala Ser Phe Lys Tyr Ser Gly Ile Tyr Gly Arg Glu Ala Asp Phe
1               5                   10                  15

Gly Ser

<210> SEQ ID NO 10
<211> LENGTH: 25
<212> TYPE: PRT
<213> ORGANISM: Artificial Sequence
<220> FEATURE:
<223> OTHER INFORMATION: 1G7 HFR1; hu1G7 HFR1; 1A5 HFR1; hu1A5 HFR1
<220> FEATURE:
<221> NAME/KEY: MISC_FEATURE
<222> LOCATION: (1)..(1)
<223> OTHER INFORMATION: Xaa = Ala or Gln
<220> FEATURE:
<221> NAME/KEY: MISC_FEATURE
<222> LOCATION: (2)..(2)
<223> OTHER INFORMATION: Xaa = Ala or Val
<220> FEATURE:
<221> NAME/KEY: MISC_FEATURE
<222> LOCATION: (14)..(14)
<223> OTHER INFORMATION: Xaa = Pro or Thr
<220> FEATURE:
<221> NAME/KEY: MISC_FEATURE
<222> LOCATION: (24)..(24)
<223> OTHER INFORMATION: Xaa = Ala or Asp

<400> SEQUENCE: 10

Xaa Xaa Gln Leu Val Glu Ser Gly Gly Gly Leu Val Gln Xaa Gly Gly
1               5                   10                  15

Ser Leu Arg Leu Ser Cys Ala Xaa Ser
            20                  25

<210> SEQ ID NO 11
<211> LENGTH: 25
<212> TYPE: PRT
<213> ORGANISM: Artificial Sequence
<220> FEATURE:
<223> OTHER INFORMATION: 1G7 HFR1

<400> SEQUENCE: 11
```

Ala Val Gln Leu Val Glu Ser Gly Gly Gly Leu Val Gln Thr Gly Gly
1               5                   10                  15

Ser Leu Arg Leu Ser Cys Ala Asp Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: hu1G7 HFR1

<400> SEQUENCE: 12

Ala Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 13
<211> LENGTH: 25
<212> TYPE: PRT
<213> ORGANISM: Artificial Sequence
<220> FEATURE:
<223> OTHER INFORMATION: 1A5 HFR1

<400> SEQUENCE: 13

Gln Ala Gln Leu Val Glu Ser Gly Gly Gly Leu Val Gln Thr Gly Gly
1               5                   10                  15

Ser Leu Arg Leu Ser Cys Ala Ala Ser
            20                  25

<210> SEQ ID NO 14
<211> LENGTH: 25
<212> TYPE: PRT
<213> ORGANISM: Artificial Sequence
<220> FEATURE:
<223> OTHER INFORMATION: hu1A5 HFR1

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 15
<211> LENGTH: 17
<212> TYPE: PRT
<213> ORGANISM: Artificial Sequence
<220> FEATURE:
<223> OTHER INFORMATION: 1G7 HFR2, hu1G7 HFR2; 1A5 HFR2, hu1A5 HFR2
<220> FEATURE:
<221> NAME/KEY: MISC_FEATURE
<222> LOCATION: (1)..(1)
<223> OTHER INFORMATION: Xaa = Met or Val

<400> SEQUENCE: 15

Xaa Gly Trp Phe Arg Gln Ala Pro Gly Lys Glu Arg Glu Phe Val Ala
1               5                   10                  15

Ala

<210> SEQ ID NO 16
<211> LENGTH: 17
<212> TYPE: PRT
<213> ORGANISM: Artificial Sequence
<220> FEATURE:

<223> OTHER INFORMATION: 1G7 HFR2, hu1G7 HFR2

<400> SEQUENCE: 16

Met Gly Trp Phe Arg Gln Ala Pro Gly Lys Glu Arg Glu Phe Val Ala
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: 1A5 HFR2, hu1A5 HFR2

<400> SEQUENCE: 17

Val Gly Trp Phe Arg Gln Ala Pro Gly Lys Glu Arg Glu Phe Val Ala
1               5                   10                  15

Ala

<210> SEQ ID NO 18
<211> LENGTH: 38
<212> TYPE: PRT
<213> ORGANISM: Artificial Sequence
<220> FEATURE:
<223> OTHER INFORMATION: 1G7 HFR3; hu1G7 HFR3; hu1A5 HFR3; 1A5 HFR3
<220> FEATURE:
<221> NAME/KEY: MISC_FEATURE
<222> LOCATION: (1)..(1)
<223> OTHER INFORMATION: Xaa = Asn or Tyr
<220> FEATURE:
<221> NAME/KEY: MISC_FEATURE
<222> LOCATION: (2)..(2)
<223> OTHER INFORMATION: Xaa = Leu or Tyr
<220> FEATURE:
<221> NAME/KEY: MISC_FEATURE
<222> LOCATION: (5)..(5)
<223> OTHER INFORMATION: Xaa = Pro or Ser
<220> FEATURE:
<221> NAME/KEY: MISC_FEATURE
<222> LOCATION: (6)..(6)
<223> OTHER INFORMATION: Xaa = Met or Val
<220> FEATURE:
<221> NAME/KEY: MISC_FEATURE
<222> LOCATION: (17)..(17)
<223> OTHER INFORMATION: Xaa = Ala or Ser
<220> FEATURE:
<221> NAME/KEY: MISC_FEATURE
<222> LOCATION: (21)..(21)
<223> OTHER INFORMATION: Xaa = Leu or Val
<220> FEATURE:
<221> NAME/KEY: MISC_FEATURE
<222> LOCATION: (22)..(22)
<223> OTHER INFORMATION: Xaa = Val or Tyr
<220> FEATURE:
<221> NAME/KEY: MISC_FEATURE
<222> LOCATION: (29)..(29)
<223> OTHER INFORMATION: Xaa = Lys or Arg
<220> FEATURE:
<221> NAME/KEY: MISC_FEATURE
<222> LOCATION: (30)..(30)
<223> OTHER INFORMATION: Xaa = Ala or Pro
<220> FEATURE:
<221> NAME/KEY: MISC_FEATURE
<222> LOCATION: (35)..(35)
<223> OTHER INFORMATION: Xaa = Ile or Val

<400> SEQUENCE: 18

Xaa Xaa Ala Asp Xaa Xaa Lys Gly Arg Phe Thr Ile Ser Arg Asp Asn
1               5                   10                  15

Xaa Lys Asn Thr Xaa Xaa Leu Gln Met Asn Ser Leu Xaa Xaa Glu Asp
            20                  25                  30

Thr Ala Xaa Tyr Tyr Cys
        35

<210> SEQ ID NO 19
<211> LENGTH: 38
<212> TYPE: PRT
<213> ORGANISM: Artificial Sequence
<220> FEATURE:
<223> OTHER INFORMATION: 1G7 HFR3

<400> SEQUENCE: 19

Asn Tyr Ala Asp Ser Met Lys Gly Arg Phe Thr Ile Ser Arg Asp Asn
1               5                   10                  15

Ala Lys Asn Thr Val Val Leu Gln Met Asn Ser Leu Lys Pro Glu Asp
            20                  25                  30

Thr Ala Ile Tyr Tyr Cys
        35

<210> SEQ ID NO 20
<211> LENGTH: 38
<212> TYPE: PRT
<213> ORGANISM: Artificial Sequence
<220> FEATURE:
<223> OTHER INFORMATION: hu1G7 HFR3; hu1A5 HFR3

<400> SEQUENCE: 20

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 21
<211> LENGTH: 38
<212> TYPE: PRT
<213> ORGANISM: Artificial Sequence
<220> FEATURE:
<223> OTHER INFORMATION: 1A5 HFR3

<400> SEQUENCE: 21

Asn Leu Ala Asp Pro Met Lys Gly Arg Phe Thr Ile Ser Arg Asp Asn
1               5                   10                  15

Ala Lys Asn Thr Val Val Leu Gln Met Asn Ser Leu Lys Pro Glu Asp
            20                  25                  30

Thr Ala Ile Tyr Tyr Cys
        35

<210> SEQ ID NO 22
<211> LENGTH: 11
<212> TYPE: PRT
<213> ORGANISM: Artificial Sequence
<220> FEATURE:
<223> OTHER INFORMATION: 1G7 HFR4; 1A5 HFR4; hu1G7 HFR4; hu1A5 HFR4
<220> FEATURE:
<221> NAME/KEY: MISC_FEATURE
<222> LOCATION: (6)..(6)
<223> OTHER INFORMATION: Xaa = Leu or Gln

<400> SEQUENCE: 22

Trp Gly Gln Gly Thr Xaa Val Thr Val Ser Ser
1               5                   10

```
<210> SEQ ID NO 23
<211> LENGTH: 11
<212> TYPE: PRT
<213> ORGANISM: Artificial Sequence
<220> FEATURE:
<223> OTHER INFORMATION: 1G7 HFR4; 1A5 HFR4

<400> SEQUENCE: 23

Trp Gly Gln Gly Thr Gln Val Thr Val Ser Ser
1               5                   10

<210> SEQ ID NO 24
<211> LENGTH: 11
<212> TYPE: PRT
<213> ORGANISM: Artificial Sequence
<220> FEATURE:
<223> OTHER INFORMATION: hu1G7 HFR4; hu1A5 HFR4

<400> SEQUENCE: 24

Trp Gly Gln Gly Thr Leu Val Thr Val Ser Ser
1               5                   10

<210> SEQ ID NO 25
<211> LENGTH: 125
<212> TYPE: PRT
<213> ORGANISM: Artificial Sequence
<220> FEATURE:
<223> OTHER INFORMATION: 1G7(antibody variable region); hu1G7(antibody
      variable region); 1A5(antibody variable region); hu1A5(antibody
      variable region)
<220> FEATURE:
<221> NAME/KEY: MISC_FEATURE
<222> LOCATION: (1)..(1)
<223> OTHER INFORMATION: Xaa = Ala or Gln
<220> FEATURE:
<221> NAME/KEY: MISC_FEATURE
<222> LOCATION: (2)..(2)
<223> OTHER INFORMATION: Xaa = Ala or Val
<220> FEATURE:
<221> NAME/KEY: MISC_FEATURE
<222> LOCATION: (14)..(14)
<223> OTHER INFORMATION: Xaa = Pro or Thr
<220> FEATURE:
<221> NAME/KEY: MISC_FEATURE
<222> LOCATION: (24)..(24)
<223> OTHER INFORMATION: Xaa = Ala or Asp
<220> FEATURE:
<221> NAME/KEY: MISC_FEATURE
<222> LOCATION: (33)..(33)
<223> OTHER INFORMATION: Xaa = Ala or Ser
<220> FEATURE:
<221> NAME/KEY: MISC_FEATURE
<222> LOCATION: (34)..(34)
<223> OTHER INFORMATION: Xaa = Met or Val
<220> FEATURE:
<221> NAME/KEY: MISC_FEATURE
<222> LOCATION: (53)..(53)
<223> OTHER INFORMATION: Xaa = Gly or Trp
<220> FEATURE:
<221> NAME/KEY: MISC_FEATURE
<222> LOCATION: (58)..(58)
<223> OTHER INFORMATION: Xaa = Thr or Val
<220> FEATURE:
<221> NAME/KEY: MISC_FEATURE
<222> LOCATION: (59)..(59)
<223> OTHER INFORMATION: Xaa = Asn or Tyr
<220> FEATURE:
<221> NAME/KEY: MISC_FEATURE
<222> LOCATION: (60)..(60)
<223> OTHER INFORMATION: Xaa = Leu or Tyr
<220> FEATURE:
<221> NAME/KEY: MISC_FEATURE
<222> LOCATION: (63)..(63)
<223> OTHER INFORMATION: Xaa = Pro or Ser
<220> FEATURE:
```

```
<221> NAME/KEY: MISC_FEATURE
<222> LOCATION: (64)..(64)
<223> OTHER INFORMATION: Xaa = Met or Val
<220> FEATURE:
<221> NAME/KEY: MISC_FEATURE
<222> LOCATION: (75)..(75)
<223> OTHER INFORMATION: Xaa = Ala or Ser
<220> FEATURE:
<221> NAME/KEY: MISC_FEATURE
<222> LOCATION: (79)..(79)
<223> OTHER INFORMATION: Xaa = Leu or Val
<220> FEATURE:
<221> NAME/KEY: MISC_FEATURE
<222> LOCATION: (80)..(80)
<223> OTHER INFORMATION: Xaa = Val or Tyr
<220> FEATURE:
<221> NAME/KEY: MISC_FEATURE
<222> LOCATION: (87)..(87)
<223> OTHER INFORMATION: Xaa = Lys or Arg
<220> FEATURE:
<221> NAME/KEY: MISC_FEATURE
<222> LOCATION: (88)..(88)
<223> OTHER INFORMATION: Xaa = Ala or Pro
<220> FEATURE:
<221> NAME/KEY: MISC_FEATURE
<222> LOCATION: (93)..(93)
<223> OTHER INFORMATION: Xaa = Ile or Val
<220> FEATURE:
<221> NAME/KEY: MISC_FEATURE
<222> LOCATION: (101)..(101)
<223> OTHER INFORMATION: Xaa = Lys or Arg
<220> FEATURE:
<221> NAME/KEY: MISC_FEATURE
<222> LOCATION: (113)..(113)
<223> OTHER INFORMATION: Xaa = Gly or Val
<220> FEATURE:
<221> NAME/KEY: MISC_FEATURE
<222> LOCATION: (120)..(120)
<223> OTHER INFORMATION: Xaa = Leu or Gln

<400> SEQUENCE: 25

Xaa Xaa Gln Leu Val Glu Ser Gly Gly Gly Leu Val Gln Xaa Gly Gly
1               5                   10                  15

Ser Leu Arg Leu Ser Cys Ala Xaa Ser Gly Arg Ile Phe Ser Asn Tyr
            20                  25                  30

Xaa Xaa Gly Trp Phe Arg Gln Ala Pro Gly Lys Glu Arg Glu Phe Val
        35                  40                  45

Ala Ala Ile Ile Xaa Ser Thr Gly Thr Xaa Xaa Xaa Ala Asp Xaa Xaa
    50                  55                  60

Lys Gly Arg Phe Thr Ile Ser Arg Asp Asn Xaa Lys Asn Thr Xaa Xaa
65                  70                  75                  80

Leu Gln Met Asn Ser Leu Xaa Xaa Glu Asp Thr Ala Xaa Tyr Tyr Cys
                85                  90                  95

Ala Ala Ser Phe Xaa Tyr Ser Gly Ile Tyr Gly Arg Glu Ala Asp Phe
            100                 105                 110

Xaa Ser Trp Gly Gln Gly Thr Xaa Val Thr Val Ser Ser
        115                 120                 125

<210> SEQ ID NO 26
<211> LENGTH: 125
<212> TYPE: PRT
<213> ORGANISM: Artificial Sequence
<220> FEATURE:
<223> OTHER INFORMATION: 1G7(antibody variable region)

<400> SEQUENCE: 26

Ala Val Gln Leu Val Glu Ser Gly Gly Gly Leu Val Gln Thr Gly Gly
1               5                   10                  15
```

```
Ser Leu Arg Leu Ser Cys Ala Asp Ser Gly Arg Ile Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ile Gly Ser Thr Gly Thr Val Asn Tyr Ala Asp Ser Met
    50                  55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Ile Tyr Tyr Cys
                85                  90                  95

Ala Ala Ser Phe Arg Tyr Ser Gly Ile Tyr Gly Arg Glu Ala Asp Phe
                100                 105                 110

Val Ser Trp Gly Gln Gly Thr Gln Val Thr Val Ser Ser
            115                 120                 125

<210> SEQ ID NO 27
<211> LENGTH: 125
<212> TYPE: PRT
<213> ORGANISM: Artificial Sequence
<220> FEATURE:
<223> OTHER INFORMATION: hu1G7(antibody variable region)

<400> SEQUENCE: 27

Ala Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ile Gly Ser Thr Gly Thr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Phe Arg Tyr Ser Gly Ile Tyr Gly Arg Glu Ala Asp Phe
                100                 105                 110

Val Ser Trp Gly Gln Gly Thr Leu Val Thr Val Ser Ser
            115                 120                 125

<210> SEQ ID NO 28
<211> LENGTH: 125
<212> TYPE: PRT
<213> ORGANISM: Artificial Sequence
<220> FEATURE:
<223> OTHER INFORMATION: 1A5(antibody variable region)

<400> SEQUENCE: 28

Gln Ala Gln Leu Val Glu Ser Gly Gly Gly Leu Val Gln Thr Gly Gly
1               5                   10                  15

Ser Leu Arg Leu Ser Cys Ala Ala Ser Gly Arg Ile Phe Ser Asn Tyr
            20                  25                  30

Ser Val Gly Trp Phe Arg Gln Ala Pro Gly Lys Glu Arg Glu Phe Val
        35                  40                  45

Ala Ala Ile Ile Trp Ser Thr Gly Thr Thr Asn Leu Ala Asp Pro Met
    50                  55                  60

Lys Gly Arg Phe Thr Ile Ser Arg Asp Asn Ala Lys Asn Thr Val Val
65                  70                  75                  80
```

```
Leu Gln Met Asn Ser Leu Lys Pro Glu Asp Thr Ala Ile Tyr Tyr Cys
                85                  90                  95

Ala Ala Ser Phe Lys Tyr Ser Gly Ile Tyr Gly Arg Glu Ala Asp Phe
            100                 105                 110

Gly Ser Trp Gly Gln Gly Thr Gln Val Thr Val Ser Ser
        115                 120                 125

<210> SEQ ID NO 29
<211> LENGTH: 125
<212> TYPE: PRT
<213> ORGANISM: Artificial Sequence
<220> FEATURE:
<223> OTHER INFORMATION: hu1A5(antibody variable region)

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Asn Tyr
            20                  25                  30

Ser Val Gly Trp Phe Arg Gln Ala Pro Gly Lys Glu Arg Glu Phe Val
        35                  40                  45

Ala Ala Ile Ile Trp Ser Thr Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Phe Lys Tyr Ser Gly Ile Tyr Gly Arg Glu Ala Asp Phe
            100                 105                 110

Gly Ser Trp Gly Gln Gly Thr Leu Val Thr Val Ser Ser
        115                 120                 125

<210> SEQ ID NO 30
<211> LENGTH: 237
<212> TYPE: PRT
<213> ORGANISM: Artificial Sequence
<220> FEATURE:
<223> OTHER INFORMATION: CAR Amino acid sequence of the non-antigen
      binding domain

<400> SEQUENCE: 30

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Lys Arg Gly Arg Lys Lys Leu Leu Tyr Ile Phe Lys Gln
                85                  90                  95

Pro Phe Met Arg Pro Val Gln Thr Thr Gln Glu Glu Asp Gly Cys Ser
            100                 105                 110

Cys Arg Phe Pro Glu Glu Glu Glu Gly Gly Cys Glu Leu Arg Val Lys
        115                 120                 125
```

```
Phe Ser Arg Ser Ala Asp Ala Pro Ala Tyr Gln Gln Gly Gln Asn Gln
        130                 135                 140

Leu Tyr Asn Glu Leu Asn Leu Gly Arg Arg Glu Glu Tyr Asp Val Leu
145                 150                 155                 160

Asp Lys Arg Arg Gly Arg Asp Pro Glu Met Gly Gly Lys Pro Arg Arg
                165                 170                 175

Lys Asn Pro Gln Glu Gly Leu Tyr Asn Glu Leu Gln Lys Asp Lys Met
            180                 185                 190

Ala Glu Ala Tyr Ser Glu Ile Gly Met Lys Gly Glu Arg Arg Arg Gly
                195                 200                 205

Lys Gly His Asp Gly Leu Tyr Gln Gly Leu Ser Thr Ala Thr Lys Asp
        210                 215                 220

Thr Tyr Asp Ala Leu His Met Gln Ala Leu Pro Pro Arg
225                 230                 235

<210> SEQ ID NO 31
<211> LENGTH: 21
<212> TYPE: PRT
<213> ORGANISM: Artificial Sequence
<220> FEATURE:
<223> OTHER INFORMATION: CD8A signal peptide amino acid sequence

<400> SEQUENCE: 31

Met Ala Leu Pro Val Thr Ala Leu Leu Leu Pro Leu Ala Leu Leu Leu
1               5                   10                  15

His Ala Ala Arg Pro
            20

<210> SEQ ID NO 32
<211> LENGTH: 383
<212> TYPE: PRT
<213> ORGANISM: Artificial Sequence
<220> FEATURE:
<223> OTHER INFORMATION: 1G7 CAR VHH

<400> SEQUENCE: 32

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Thr Gly Gly Ser Leu Arg Leu Ser Cys Ala Asp Ser Gly Arg
        35                  40                  45

Ile Phe Ser Asn Tyr Ala Met Gly Trp Phe Arg Gln Ala Pro Gly Lys
    50                  55                  60

Glu Arg Glu Phe Val Ala Ala Ile Ile Gly Ser Thr Gly Thr Val Asn
65                  70                  75                  80

Tyr Ala Asp Ser Met Lys Gly Arg Phe Thr Ile Ser Arg Asp Asn Ala
                85                  90                  95

Lys Asn Thr Val Val Leu Gln Met Asn Ser Leu Lys Pro Glu Asp Thr
            100                 105                 110

Ala Ile Tyr Tyr Cys Ala Ala Ser Phe Arg Tyr Ser Gly Ile Tyr Gly
        115                 120                 125

Arg Glu Ala Asp Phe Val Ser Trp Gly Gln Gly Thr Gln Val Thr Val
    130                 135                 140

Ser Ser Phe Val Pro Val Phe Leu Pro Ala Lys Pro Thr Thr Thr Pro
145                 150                 155                 160

Ala Pro Arg Pro Pro Thr Pro Ala Pro Thr Ile Ala Ser Gln Pro Leu
                165                 170                 175
```

```
Ser Leu Arg Pro Glu Ala Cys Arg Pro Ala Ala Gly Gly Ala Val His
        180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
        210                 215                 220

Cys Asn His Arg Asn Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
                245                 250                 255

Cys Ser Cys Arg Phe Pro Glu Glu Glu Glu Gly Gly Cys Glu Leu Arg
                260                 265                 270

Val Lys Phe Ser Arg Ser Ala Asp Ala Pro Ala Tyr Gln Gln Gly Gln
            275                 280                 285

Asn Gln Leu Tyr Asn Glu Leu Asn Leu Gly Arg Arg Glu Glu Tyr Asp
        290                 295                 300

Val Leu Asp Lys Arg Arg Gly Arg Asp Pro Glu Met Gly Gly Lys Pro
305                 310                 315                 320

Arg Arg Lys Asn Pro Gln Glu Gly Leu Tyr Asn Glu Leu Gln Lys Asp
                325                 330                 335

Lys Met Ala Glu Ala Tyr Ser Glu Ile Gly Met Lys Gly Glu Arg Arg
                340                 345                 350

Arg Gly Lys Gly His Asp Gly Leu Tyr Gln Gly Leu Ser Thr Ala Thr
            355                 360                 365

Lys Asp Thr Tyr Asp Ala Leu His Met Gln Ala Leu Pro Pro Arg
        370                 375                 380

<210> SEQ ID NO 33
<211> LENGTH: 383
<212> TYPE: PRT
<213> ORGANISM: Artificial Sequence
<220> FEATURE:
<223> OTHER INFORMATION: Hu1G7 CAR VHH

<400> SEQUENCE: 33

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Pro Gly Gly Ser Leu Arg Leu Ser Cys Ala Ala Ser Gly Arg
        35                  40                  45

Ile Phe Ser Asn Tyr Ala Met Gly Trp Phe Arg Gln Ala Pro Gly Lys
    50                  55                  60

Glu Arg Glu Phe Val Ala Ala Ile Ile Gly Ser Thr Gly Thr Val Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Ser Phe Arg Tyr Ser Gly Ile Tyr Gly
        115                 120                 125

Arg Glu Ala Asp Phe Val Ser Trp Gly Gln Gly Thr Leu Val Thr Val
    130                 135                 140

Ser Ser Phe Val Pro Val Phe Leu Pro Ala Lys Pro Thr Thr Thr Pro
145                 150                 155                 160
```

Ala Pro Arg Pro Pro Thr Pro Ala Pro Thr Ile Ala Ser Gln Pro Leu
            165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
            210                 215                 220

Cys Asn His Arg Asn Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
            245                 250                 255

Cys Ser Cys Arg Phe Pro Glu Glu Glu Glu Gly Gly Cys Glu Leu Arg
            260                 265                 270

Val Lys Phe Ser Arg Ser Ala Asp Ala Pro Ala Tyr Gln Gln Gly Gln
            275                 280                 285

Asn Gln Leu Tyr Asn Glu Leu Asn Leu Gly Arg Arg Glu Glu Tyr Asp
            290                 295                 300

Val Leu Asp Lys Arg Arg Gly Arg Asp Pro Glu Met Gly Gly Lys Pro
305                 310                 315                 320

Arg Arg Lys Asn Pro Gln Glu Gly Leu Tyr Asn Glu Leu Gln Lys Asp
            325                 330                 335

Lys Met Ala Glu Ala Tyr Ser Glu Ile Gly Met Lys Gly Glu Arg Arg
            340                 345                 350

Arg Gly Lys Gly His Asp Gly Leu Tyr Gln Gly Leu Ser Thr Ala Thr
            355                 360                 365

Lys Asp Thr Tyr Asp Ala Leu His Met Gln Ala Leu Pro Pro Arg
            370                 375                 380

<210> SEQ ID NO 34
<211> LENGTH: 383
<212> TYPE: PRT
<213> ORGANISM: Artificial Sequence
<220> FEATURE:
<223> OTHER INFORMATION: 1A5 CAR VHH

<400> SEQUENCE: 34

Met Ala Leu Pro Val Thr Ala Leu Leu Leu Pro Leu Ala Leu Leu Leu
1               5                   10                  15

His Ala Ala Arg Pro Gln Ala Gln Leu Val Glu Ser Gly Gly Gly Leu
            20                  25                  30

Val Gln Thr Gly Gly Ser Leu Arg Leu Ser Cys Ala Ala Ser Gly Arg
            35                  40                  45

Ile Phe Ser Asn Tyr Ser Val Gly Trp Phe Arg Gln Ala Pro Gly Lys
            50                  55                  60

Glu Arg Glu Phe Val Ala Ala Ile Ile Trp Ser Thr Gly Thr Thr Asn
65                  70                  75                  80

Leu Ala Asp Pro Met Lys Gly Arg Phe Thr Ile Ser Arg Asp Asn Ala
            85                  90                  95

Lys Asn Thr Val Val Leu Gln Met Asn Ser Leu Lys Pro Glu Asp Thr
            100                 105                 110

Ala Ile Tyr Tyr Cys Ala Ala Ser Phe Lys Tyr Ser Gly Ile Tyr Gly
            115                 120                 125

Arg Glu Ala Asp Phe Gly Ser Trp Gly Gln Gly Thr Gln Val Thr Val
            130                 135                 140

```
Ser Ser Phe Val Pro Val Phe Leu Pro Ala Lys Pro Thr Thr Thr Pro
145                 150                 155                 160

Ala Pro Arg Pro Pro Thr Pro Ala Pro Thr Ile Ala Ser Gln Pro Leu
            165                 170                 175

Ser Leu Arg Pro Glu Ala Cys Arg Pro Ala Ala Gly Gly Ala Val His
        180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Asn His Arg Asn Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
                245                 250                 255

Cys Ser Cys Arg Phe Pro Glu Glu Glu Glu Gly Gly Cys Glu Leu Arg
            260                 265                 270

Val Lys Phe Ser Arg Ser Ala Asp Ala Pro Ala Tyr Gln Gln Gly Gln
        275                 280                 285

Asn Gln Leu Tyr Asn Glu Leu Asn Leu Gly Arg Arg Glu Glu Tyr Asp
    290                 295                 300

Val Leu Asp Lys Arg Arg Gly Arg Asp Pro Glu Met Gly Gly Lys Pro
305                 310                 315                 320

Arg Arg Lys Asn Pro Gln Glu Gly Leu Tyr Asn Glu Leu Gln Lys Asp
                325                 330                 335

Lys Met Ala Glu Ala Tyr Ser Glu Ile Gly Met Lys Gly Glu Arg Arg
            340                 345                 350

Arg Gly Lys Gly His Asp Gly Leu Tyr Gln Gly Leu Ser Thr Ala Thr
        355                 360                 365

Lys Asp Thr Tyr Asp Ala Leu His Met Gln Ala Leu Pro Pro Arg
    370                 375                 380

<210> SEQ ID NO 35
<211> LENGTH: 383
<212> TYPE: PRT
<213> ORGANISM: Artificial Sequence
<220> FEATURE:
<223> OTHER INFORMATION: Hu1A5 CAR VHH

<400> SEQUENCE: 35

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Arg
        35                  40                  45

Ile Phe Ser Asn Tyr Ser Val Gly Trp Phe Arg Gln Ala Pro Gly Lys
    50                  55                  60

Glu Arg Glu Phe Val Ala Ala Ile Ile Trp Ser Thr Gly Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Ser Phe Lys Tyr Ser Gly Ile Tyr Gly
        115                 120                 125
```

```
Arg Glu Ala Asp Phe Gly Ser Trp Gly Gln Gly Thr Leu Val Thr Val
        130                 135                 140

Ser Ser Phe Val Pro Val Phe Leu Pro Ala Lys Pro Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
        210                 215                 220

Cys Asn His Arg Asn Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
                245                 250                 255

Cys Ser Cys Arg Phe Pro Glu Glu Glu Glu Gly Gly Cys Glu Leu Arg
            260                 265                 270

Val Lys Phe Ser Arg Ser Ala Asp Ala Pro Ala Tyr Gln Gln Gly Gln
        275                 280                 285

Asn Gln Leu Tyr Asn Glu Leu Asn Leu Gly Arg Arg Glu Glu Tyr Asp
290                 295                 300

Val Leu Asp Lys Arg Arg Gly Arg Asp Pro Glu Met Gly Gly Lys Pro
305                 310                 315                 320

Arg Arg Lys Asn Pro Gln Glu Gly Leu Tyr Asn Glu Leu Gln Lys Asp
                325                 330                 335

Lys Met Ala Glu Ala Tyr Ser Glu Ile Gly Met Lys Gly Glu Arg Arg
                340                 345                 350

Arg Gly Lys Gly His Asp Gly Leu Tyr Gln Gly Leu Ser Thr Ala Thr
            355                 360                 365

Lys Asp Thr Tyr Asp Ala Leu His Met Gln Ala Leu Pro Pro Arg
        370                 375                 380

<210> SEQ ID NO 36
<211> LENGTH: 375
<212> TYPE: DNA
<213> ORGANISM: Artificial Sequence
<220> FEATURE:
<223> OTHER INFORMATION: 1G7(antibody variable region) nucleotide
      sequence

<400> SEQUENCE: 36
gctgtccagc ttgtggagtc tgggggggc ctcgtccaga caggcggttc tctccgcctc      60
tcctgtgctg attctggcag aatcttttca aactacgcaa tgggctggtt caggcaggca     120
ccaggcaagg agcgggagtt cgtggctgct atcattggat ctactggcac cgttaactac     180
gcagacagca tgaaaggcag atttaccatc tcaagagata cgccaaaaa tactgtagtc     240 ctccagatga actctctgaa gcctgaggat accgctatat attattgtgc ggcgtcattc     300
aggtacagcg gcatctatgg ccgcgaagcg gattttgtta ttggggaca agggacccaa      360 gtgacagtgt cttca                                                     375

<210> SEQ ID NO 37
<211> LENGTH: 375
<212> TYPE: DNA
<213> ORGANISM: Artificial Sequence
```

```
<220> FEATURE:
<223> OTHER INFORMATION: hu1G7(antibody variable region) nucleotide
      sequence

<400> SEQUENCE: 37
gctgttcagc tggtggagtc tggtggcggg ctcgttcagc cgggcggcag cctcagactg    60
agctgtgcag cctccggaag gatcttttca aattacgcaa tggggtggtt taggcaggca   120
ccaggaaagg agcgagagtt tgtggcagca ataatcggtt ctaccggcac agtgtattac   180
gctgatagcg tgaaaggcag gttcaccatt tcaagggata acagtaaaaa cacactatac   240
ttacagatga actccttacg agccgaagac acggcggtgt actactgtgc cgcatccttt   300
agatactctg gaatttacgg acgcgaggcc gactttgtca gctgggtca ggggactctt    360 gttaccgtat cctct                                                     375

<210> SEQ ID NO 38
<211> LENGTH: 375
<212> TYPE: DNA
<213> ORGANISM: Artificial Sequence
<220> FEATURE:
<223> OTHER INFORMATION: 1A5(antibody variable region) nucleotide
      sequence

<400> SEQUENCE: 38
caggctcaac tggtggagtc gggaggtggc ttggtgcaga caggagggag cctgcgactc    60
tcctgtgcgg cttccggaag gatttttctct aattattctg tcggatggtt ccggcaggcc   120
ccaggcaaag agcgtgaatt cgttgcggcg ataatctggt cgaccggaac aacgaatctg   180
gccgatccca tgaaggggag attcaccatt agtagagaca acgcaaaaaa cacagtagtc   240
ctgcagatga acagcctcaa acccgaggat acagctatct attactgcgc agcttccttt   300
aaatattctg gcatatatgg cagagaagca gattttggga gttgggggca gggcacccag   360
gtgacagtca gttct                                                     375

<210> SEQ ID NO 39
<211> LENGTH: 375
<212> TYPE: DNA
<213> ORGANISM: Artificial Sequence
<220> FEATURE:
<223> OTHER INFORMATION: hu1A5(antibody variable region) nucleotide
      sequence

<400> SEQUENCE: 39
caggtccaat tagtggaaag tggtgggga ttagtgcaac cgggcggctc cctccgcctt     60
tcctgcgccg cttctggcag aatcttctcc aactactccg ttggatggtt tcgtcaggcc   120
ccaggaaaag agagagaatt cgtggctgct atcatatgga gcacgggac cacctactat     180 gccgatagcg tcaaaggcag gttcactatc agcagggata tagcaagaa tacactatac     240 ttgcaaatga actcgctgcg agccgaagac acagccgtct actactgtgc ggcgtcattt   300
aaatacagcg gcatttacgg ccgagaggca gatttcggaa gttgggggca gggaaccttg   360
gtgacagtct cctcg                                                     375

<210> SEQ ID NO 40
<211> LENGTH: 711
<212> TYPE: DNA
<213> ORGANISM: Artificial Sequence
<220> FEATURE:
<223> OTHER INFORMATION: CAR non-antigen-binding DNA sequence

<400> SEQUENCE: 40
```

```
ttcgtccccg tgttcctgcc tgccaagcca acaactaccc ctgctccacg accacctact    60
ccagcaccta ccatcgcaag tcagcccctg tcactgcgac ctgaggcttg ccggccagca   120
gctggaggag cagtgcacac ccgaggcctg gacttcgcat gcgatatcta catttgggca   180
ccactggctg gaacctgtgg ggtcctgctg ctgagcctgg tcatcaccct gtattgtaac   240
cacagaaata aaggggggcg caagaaactg ctgtacatct tcaagcagcc ttttatgcgc   300
ccagtgcaga caactcagga ggaagacgga tgctcttgtc ggttcccaga ggaggaggaa   360
ggaggctgcg agctgagagt gaagttcagc cggagcgccg atgcaccagc atatcagcag   420
ggacagaatc agctgtacaa cgagctgaat ctgggcaggc gcgaggaata tgacgtgctg   480
gataagcgac gaggacggga ccccgaaatg ggaggaaaac cagaaggaa gaaccctcag   540 gagggggctgt ataatgaact gcagaaagac aagatggctg aggcatacag cgaaattgga   600
atgaaaggag agcgccgacg ggggaaggga cacgatgggc tgtaccaggg actgtcaacc   660
gccactaaag atacctacga cgcactgcac atgcaggctc tgccccaag a             711
```

<210> SEQ ID NO 41
<211> LENGTH: 63
<212> TYPE: DNA
<213> ORGANISM: Artificial Sequence
<220> FEATURE:
<223> OTHER INFORMATION: CD8A signal peptide nucleic acid sequence

<400> SEQUENCE: 41

```
atggccttac cagtgaccgc cttgctcctg ccgctggcct tgctgctcca cgccgccagg    60
ccg                                                                  63
```

<210> SEQ ID NO 42
<211> LENGTH: 21
<212> TYPE: PRT
<213> ORGANISM: Artificial Sequence
<220> FEATURE:
<223> OTHER INFORMATION: CD8A transmembrane domain

<400> SEQUENCE: 42

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 43
<211> LENGTH: 21
<212> TYPE: PRT
<213> ORGANISM: Artificial Sequence
<220> FEATURE:
<223> OTHER INFORMATION: CD8B transmembrane domain

<400> SEQUENCE: 43

Ile Thr Leu Gly Leu Leu Val Ala Gly Val Leu Val Leu Leu Val Ser
1               5                   10                  15

Leu Gly Val Ala Ile
            20

<210> SEQ ID NO 44
<211> LENGTH: 27
<212> TYPE: PRT
<213> ORGANISM: Artificial Sequence
<220> FEATURE:
<223> OTHER INFORMATION: CD28 transmembrane domain

```
<400> SEQUENCE: 44

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 45
<211> LENGTH: 27
<212> TYPE: PRT
<213> ORGANISM: Artificial Sequence
<220> FEATURE:
<223> OTHER INFORMATION: 4-1BB transmembrane domain

<400> SEQUENCE: 45

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 46
<211> LENGTH: 22
<212> TYPE: PRT
<213> ORGANISM: Artificial Sequence
<220> FEATURE:
<223> OTHER INFORMATION: CD4 transmembrane domain

<400> SEQUENCE: 46

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 47
<211> LENGTH: 21
<212> TYPE: PRT
<213> ORGANISM: Artificial Sequence
<220> FEATURE:
<223> OTHER INFORMATION: CD27 transmembrane domain

<400> SEQUENCE: 47

Ile Leu Val Ile Phe Ser Gly Met Phe Leu Val Phe Thr Leu Ala Gly
1               5                   10                  15

Ala Leu Phe Leu His
            20

<210> SEQ ID NO 48
<211> LENGTH: 21
<212> TYPE: PRT
<213> ORGANISM: Artificial Sequence
<220> FEATURE:
<223> OTHER INFORMATION: CD7 transmembrane domain

<400> SEQUENCE: 48

Ala Ala Leu Ala Val Ile Ser Phe Leu Leu Gly Leu Gly Leu Gly Val
1               5                   10                  15

Ala Cys Val Leu Ala
            20

<210> SEQ ID NO 49
<211> LENGTH: 21
<212> TYPE: PRT
<213> ORGANISM: Artificial Sequence
<220> FEATURE:
<223> OTHER INFORMATION: PD-1 transmembrane domain
```

```
<400> SEQUENCE: 49

Val Gly Val Val Gly Gly Leu Leu Gly Ser Leu Val Leu Leu Val Trp
1               5                   10                  15

Val Leu Ala Val Ile
            20

<210> SEQ ID NO 50
<211> LENGTH: 23
<212> TYPE: PRT
<213> ORGANISM: Artificial Sequence
<220> FEATURE:
<223> OTHER INFORMATION: TRAC transmembrane domain

<400> SEQUENCE: 50

Val Ile Gly Phe Arg Ile Leu Leu Leu Lys Val Ala Gly Phe Asn Leu
1               5                   10                  15

Leu Met Thr Leu Arg Leu Trp
            20

<210> SEQ ID NO 51
<211> LENGTH: 21
<212> TYPE: PRT
<213> ORGANISM: Artificial Sequence
<220> FEATURE:
<223> OTHER INFORMATION: TRBC transmembrane domain

<400> SEQUENCE: 51

Ile Leu Leu Gly Lys Ala Thr Leu Tyr Ala Val Leu Val Ser Ala Leu
1               5                   10                  15

Val Leu Met Ala Met
            20

<210> SEQ ID NO 52
<211> LENGTH: 26
<212> TYPE: PRT
<213> ORGANISM: Artificial Sequence
<220> FEATURE:
<223> OTHER INFORMATION: CD3epsilon transmembrane domain

<400> SEQUENCE: 52

Val Met Ser Val Ala Thr Ile Val Ile Val Asp Ile Cys Ile Thr Gly
1               5                   10                  15

Gly Leu Leu Leu Leu Val Tyr Tyr Trp Ser
            20                  25

<210> SEQ ID NO 53
<211> LENGTH: 21
<212> TYPE: PRT
<213> ORGANISM: Artificial Sequence
<220> FEATURE:
<223> OTHER INFORMATION: CD3zeta transmembrane domain

<400> SEQUENCE: 53

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 54
<211> LENGTH: 21
<212> TYPE: PRT
<213> ORGANISM: Artificial Sequence
<220> FEATURE:
```

<223> OTHER INFORMATION: CTLA-4 transmembrane domain

<400> SEQUENCE: 54

Phe Leu Leu Trp Ile Leu Ala Ala Val Ser Ser Gly Leu Phe Phe Tyr
1               5                   10                  15

Ser Phe Leu Leu Thr
            20

<210> SEQ ID NO 55
<211> LENGTH: 21
<212> TYPE: PRT
<213> ORGANISM: Artificial Sequence
<220> FEATURE:
<223> OTHER INFORMATION: LAG-3 transmembrane domain

<400> SEQUENCE: 55

Leu Leu Phe Leu Ile Leu Gly Val Leu Ser Leu Leu Leu Leu Val Thr
1               5                   10                  15

Gly Ala Phe Gly Phe
            20

<210> SEQ ID NO 56
<211> LENGTH: 30
<212> TYPE: PRT
<213> ORGANISM: Artificial Sequence
<220> FEATURE:
<223> OTHER INFORMATION: CD5 transmembrane domain

<400> SEQUENCE: 56

Ala Gly Leu Ala Ala Gly Thr Val Ala Ser Ile Ile Leu Ala Leu Val
1               5                   10                  15

Leu Leu Val Val Leu Leu Val Val Cys Gly Pro Leu Ala Tyr
            20                  25                  30

<210> SEQ ID NO 57
<211> LENGTH: 21
<212> TYPE: PRT
<213> ORGANISM: Artificial Sequence
<220> FEATURE:
<223> OTHER INFORMATION: ICOS transmembrane domain

<400> SEQUENCE: 57

Phe Trp Leu Pro Ile Gly Cys Ala Ala Phe Val Val Cys Ile Leu
1               5                   10                  15

Gly Cys Ile Leu Ile
            20

<210> SEQ ID NO 58
<211> LENGTH: 21
<212> TYPE: PRT
<213> ORGANISM: Artificial Sequence
<220> FEATURE:
<223> OTHER INFORMATION: OX40 transmembrane domain

<400> SEQUENCE: 58

Val Ala Ala Ile Leu Gly Leu Gly Leu Val Leu Gly Leu Leu Gly Pro
1               5                   10                  15

Leu Ala Ile Leu Leu
            20

<210> SEQ ID NO 59
<211> LENGTH: 21
<212> TYPE: PRT
<213> ORGANISM: Artificial Sequence

```
<220> FEATURE:
<223> OTHER INFORMATION: NKG2D transmembrane domain

<400> SEQUENCE: 59

Pro Phe Phe Phe Cys Cys Phe Ile Ala Val Ala Met Gly Ile Arg Phe
1               5                   10                  15

Ile Ile Met Val Ala
            20

<210> SEQ ID NO 60
<211> LENGTH: 21
<212> TYPE: PRT
<213> ORGANISM: Artificial Sequence
<220> FEATURE:
<223> OTHER INFORMATION: 2B4 transmembrane domain

<400> SEQUENCE: 60

Phe Leu Val Ile Ile Val Ile Leu Ser Ala Leu Phe Leu Gly Thr Leu
1               5                   10                  15

Ala Cys Phe Cys Val
            20

<210> SEQ ID NO 61
<211> LENGTH: 21
<212> TYPE: PRT
<213> ORGANISM: Artificial Sequence
<220> FEATURE:
<223> OTHER INFORMATION: FcepsilonRIgamma transmembrane domain

<400> SEQUENCE: 61

Leu Cys Tyr Ile Leu Asp Ala Ile Leu Phe Leu Tyr Gly Ile Val Leu
1               5                   10                  15

Thr Leu Leu Tyr Cys
            20

<210> SEQ ID NO 62
<211> LENGTH: 21
<212> TYPE: PRT
<213> ORGANISM: Artificial Sequence
<220> FEATURE:
<223> OTHER INFORMATION: BTLA transmembrane domain

<400> SEQUENCE: 62

Leu Leu Pro Leu Gly Gly Leu Pro Leu Leu Ile Thr Thr Cys Phe Cys
1               5                   10                  15

Leu Phe Cys Cys Leu
            20

<210> SEQ ID NO 63
<211> LENGTH: 21
<212> TYPE: PRT
<213> ORGANISM: Artificial Sequence
<220> FEATURE:
<223> OTHER INFORMATION: CD30 transmembrane domain

<400> SEQUENCE: 63

Pro Val Leu Phe Trp Val Ile Leu Val Leu Val Val Val Val Gly Ser
1               5                   10                  15

Ser Ala Phe Leu Leu
            20

<210> SEQ ID NO 64
<211> LENGTH: 21
<212> TYPE: PRT
```

```
<213> ORGANISM: Artificial Sequence
<220> FEATURE:
<223> OTHER INFORMATION: GITR transmembrane domain

<400> SEQUENCE: 64

Leu Gly Trp Leu Thr Val Val Leu Ala Val Ala Ala Cys Val Leu
1               5                   10                  15

Leu Leu Thr Ser Ala
            20

<210> SEQ ID NO 65
<211> LENGTH: 21
<212> TYPE: PRT
<213> ORGANISM: Artificial Sequence
<220> FEATURE:
<223> OTHER INFORMATION: HVEM transmembrane domain

<400> SEQUENCE: 65

Trp Trp Phe Leu Ser Gly Ser Leu Val Ile Val Ile Val Cys Ser Thr
1               5                   10                  15

Val Gly Leu Ile Ile
            20

<210> SEQ ID NO 66
<211> LENGTH: 21
<212> TYPE: PRT
<213> ORGANISM: Artificial Sequence
<220> FEATURE:
<223> OTHER INFORMATION: DAP10 transmembrane domain

<400> SEQUENCE: 66

Leu Leu Ala Gly Leu Val Ala Ala Asp Ala Val Ala Ser Leu Leu Ile
1               5                   10                  15

Val Gly Ala Val Phe
            20

<210> SEQ ID NO 67
<211> LENGTH: 26
<212> TYPE: PRT
<213> ORGANISM: Artificial Sequence
<220> FEATURE:
<223> OTHER INFORMATION: CD2 transmembrane domain

<400> SEQUENCE: 67

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 68
<211> LENGTH: 23
<212> TYPE: PRT
<213> ORGANISM: Artificial Sequence
<220> FEATURE:
<223> OTHER INFORMATION: NKG2C transmembrane domain

<400> SEQUENCE: 68

Leu Thr Ala Glu Val Leu Gly Ile Ile Cys Ile Val Leu Met Ala Thr
1               5                   10                  15

Val Leu Lys Thr Ile Val Leu
            20

<210> SEQ ID NO 69
<211> LENGTH: 21
```

```
<212> TYPE: PRT
<213> ORGANISM: Artificial Sequence
<220> FEATURE:
<223> OTHER INFORMATION: LIGHT transmembrane domain

<400> SEQUENCE: 69

Val Gly Leu Gly Leu Leu Leu Leu Met Gly Ala Gly Leu Ala Val
1               5                   10                  15

Gln Gly Trp Phe Leu
            20

<210> SEQ ID NO 70
<211> LENGTH: 21
<212> TYPE: PRT
<213> ORGANISM: Artificial Sequence
<220> FEATURE:
<223> OTHER INFORMATION: DAP12 transmembrane domain

<400> SEQUENCE: 70

Gly Val Leu Ala Gly Ile Val Met Gly Asp Leu Val Leu Thr Val Leu
1               5                   10                  15

Ile Ala Leu Ala Val
            20

<210> SEQ ID NO 71
<211> LENGTH: 24
<212> TYPE: PRT
<213> ORGANISM: Artificial Sequence
<220> FEATURE:
<223> OTHER INFORMATION: CD40L transmembrane domain

<400> SEQUENCE: 71

Ile Phe Met Tyr Leu Leu Thr Val Phe Leu Ile Thr Gln Met Ile Gly
1               5                   10                  15

Ser Ala Leu Phe Ala Val Tyr Leu
            20

<210> SEQ ID NO 72
<211> LENGTH: 21
<212> TYPE: PRT
<213> ORGANISM: Artificial Sequence
<220> FEATURE:
<223> OTHER INFORMATION: TIM1 transmembrane domain

<400> SEQUENCE: 72

Ile Tyr Ala Gly Val Cys Ile Ser Val Leu Val Leu Leu Ala Leu Leu
1               5                   10                  15

Gly Val Ile Ile Ala
            20

<210> SEQ ID NO 73
<211> LENGTH: 21
<212> TYPE: PRT
<213> ORGANISM: Artificial Sequence
<220> FEATURE:
<223> OTHER INFORMATION: CD226 transmembrane domain

<400> SEQUENCE: 73

Gly Gly Thr Val Leu Leu Leu Leu Phe Val Ile Ser Ile Thr Thr Ile
1               5                   10                  15

Ile Val Ile Phe Leu
            20

<210> SEQ ID NO 74
```

```
<211> LENGTH: 21
<212> TYPE: PRT
<213> ORGANISM: Artificial Sequence
<220> FEATURE:
<223> OTHER INFORMATION: DR3 transmembrane domain

<400> SEQUENCE: 74

Met Phe Trp Val Gln Val Leu Leu Ala Gly Leu Val Val Pro Leu Leu
1               5                   10                  15

Leu Gly Ala Thr Leu
            20

<210> SEQ ID NO 75
<211> LENGTH: 21
<212> TYPE: PRT
<213> ORGANISM: Artificial Sequence
<220> FEATURE:
<223> OTHER INFORMATION: CD45 transmembrane domain

<400> SEQUENCE: 75

Ala Leu Ile Ala Phe Leu Ala Phe Leu Ile Ile Val Thr Ser Ile Ala
1               5                   10                  15

Leu Leu Val Val Leu
            20

<210> SEQ ID NO 76
<211> LENGTH: 21
<212> TYPE: PRT
<213> ORGANISM: Artificial Sequence
<220> FEATURE:
<223> OTHER INFORMATION: CD80 transmembrane domain

<400> SEQUENCE: 76

Leu Leu Pro Ser Trp Ala Ile Thr Leu Ile Ser Val Asn Gly Ile Phe
1               5                   10                  15

Val Ile Cys Cys Leu
            20

<210> SEQ ID NO 77
<211> LENGTH: 21
<212> TYPE: PRT
<213> ORGANISM: Artificial Sequence
<220> FEATURE:
<223> OTHER INFORMATION: CD86 transmembrane domain

<400> SEQUENCE: 77

Trp Ile Thr Ala Val Leu Pro Thr Val Ile Ile Cys Val Met Val Phe
1               5                   10                  15

Cys Leu Ile Leu Trp
            20

<210> SEQ ID NO 78
<211> LENGTH: 21
<212> TYPE: PRT
<213> ORGANISM: Artificial Sequence
<220> FEATURE:
<223> OTHER INFORMATION: CD9 transmembrane domain1

<400> SEQUENCE: 78

Leu Leu Phe Gly Phe Asn Phe Ile Phe Trp Leu Ala Gly Ile Ala Val
1               5                   10                  15

Leu Ala Ile Gly Leu
            20
```

```
<210> SEQ ID NO 79
<211> LENGTH: 21
<212> TYPE: PRT
<213> ORGANISM: Artificial Sequence
<220> FEATURE:
<223> OTHER INFORMATION: CD9 transmembrane domain2

<400> SEQUENCE: 79

Phe Tyr Thr Gly Val Tyr Ile Leu Ile Gly Ala Gly Ala Leu Met Met
1               5                   10                  15

Leu Val Gly Phe Leu
            20

<210> SEQ ID NO 80
<211> LENGTH: 24
<212> TYPE: PRT
<213> ORGANISM: Artificial Sequence
<220> FEATURE:
<223> OTHER INFORMATION: CD9 transmembrane domain3

<400> SEQUENCE: 80

Met Leu Gly Leu Phe Phe Gly Phe Leu Leu Val Ile Phe Ala Ile Glu
1               5                   10                  15

Ile Ala Ala Ala Ile Trp Gly Tyr
            20

<210> SEQ ID NO 81
<211> LENGTH: 26
<212> TYPE: PRT
<213> ORGANISM: Artificial Sequence
<220> FEATURE:
<223> OTHER INFORMATION: CD9 transmembrane domain4

<400> SEQUENCE: 81

Ile Gly Ala Val Gly Ile Gly Ile Ala Val Val Met Ile Phe Gly Met
1               5                   10                  15

Ile Phe Ser Met Ile Leu Cys Cys Ala Ile
            20                  25

<210> SEQ ID NO 82
<211> LENGTH: 21
<212> TYPE: PRT
<213> ORGANISM: Artificial Sequence
<220> FEATURE:
<223> OTHER INFORMATION: CD16 transmembrane domain

<400> SEQUENCE: 82

Val Ser Phe Cys Leu Val Met Val Leu Leu Phe Ala Val Asp Thr Gly
1               5                   10                  15

Leu Tyr Phe Ser Val
            20

<210> SEQ ID NO 83
<211> LENGTH: 19
<212> TYPE: PRT
<213> ORGANISM: Artificial Sequence
<220> FEATURE:
<223> OTHER INFORMATION: CD22 transmembrane domain

<400> SEQUENCE: 83

Val Ala Val Gly Leu Gly Ser Cys Leu Ala Ile Leu Ile Leu Ala Ile
1               5                   10                  15

Cys Gly Leu
```

```
<210> SEQ ID NO 84
<211> LENGTH: 23
<212> TYPE: PRT
<213> ORGANISM: Artificial Sequence
<220> FEATURE:
<223> OTHER INFORMATION: CD33 transmembrane domain

<400> SEQUENCE: 84

Gly Ala Ile Gly Gly Ala Gly Val Thr Ala Leu Leu Ala Leu Cys Leu
1               5                   10                  15

Cys Leu Ile Phe Phe Ile Val
            20

<210> SEQ ID NO 85
<211> LENGTH: 21
<212> TYPE: PRT
<213> ORGANISM: Artificial Sequence
<220> FEATURE:
<223> OTHER INFORMATION: CD37 transmembrane domain1

<400> SEQUENCE: 85

Phe Asn Leu Phe Phe Phe Val Leu Gly Ser Leu Ile Phe Cys Phe Gly
1               5                   10                  15

Ile Trp Ile Leu Ile
            20

<210> SEQ ID NO 86
<211> LENGTH: 15
<212> TYPE: PRT
<213> ORGANISM: Artificial Sequence
<220> FEATURE:
<223> OTHER INFORMATION: CD37 transmembrane domain2

<400> SEQUENCE: 86

Val Leu Ala Ile Ser Gly Ile Phe Thr Met Gly Ile Ala Leu Leu
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: CD37 transmembrane domain3

<400> SEQUENCE: 87

Leu Leu Gly Leu Tyr Phe Gly Met Leu Leu Leu Leu Phe Ala Thr Gln
1               5                   10                  15

<210> SEQ ID NO 88
<211> LENGTH: 25
<212> TYPE: PRT
<213> ORGANISM: Artificial Sequence
<220> FEATURE:
<223> OTHER INFORMATION: CD37 transmembrane domain4

<400> SEQUENCE: 88

Leu Ile Ser Ile Val Gly Ile Cys Leu Gly Val Gly Leu Leu Glu Leu
1               5                   10                  15

Gly Phe Met Thr Leu Ser Ile Phe Leu
            20                  25

<210> SEQ ID NO 89
<211> LENGTH: 21
<212> TYPE: PRT
<213> ORGANISM: Artificial Sequence
<220> FEATURE:
```

<223> OTHER INFORMATION: CD64 transmembrane domain

<400> SEQUENCE: 89

Val Leu Phe Tyr Leu Ala Val Gly Ile Met Phe Leu Val Asn Thr Val
1               5                   10                  15

Leu Trp Val Thr Ile
            20

<210> SEQ ID NO 90
<211> LENGTH: 21
<212> TYPE: PRT
<213> ORGANISM: Artificial Sequence
<220> FEATURE:
<223> OTHER INFORMATION: SLAM transmembrane domain

<400> SEQUENCE: 90

Trp Ala Val Tyr Ala Gly Leu Leu Gly Gly Val Ile Met Ile Leu Ile
1               5                   10                  15

Met Val Val Ile Leu
            20

<210> SEQ ID NO 91
<211> LENGTH: 41
<212> TYPE: PRT
<213> ORGANISM: Artificial Sequence
<220> FEATURE:
<223> OTHER INFORMATION: CD28 intracellular co-stimulatory signaling
      domain

<400> SEQUENCE: 91

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 92
<211> LENGTH: 42
<212> TYPE: PRT
<213> ORGANISM: Artificial Sequence
<220> FEATURE:
<223> OTHER INFORMATION: CD137 intracellular co-stimulatory signaling
      domain

<400> SEQUENCE: 92

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 93
<211> LENGTH: 48
<212> TYPE: PRT
<213> ORGANISM: Artificial Sequence
<220> FEATURE:
<223> OTHER INFORMATION: CD27 intracellular co-stimulatory signaling
      domain

<400> SEQUENCE: 93

Gln Arg Arg Lys Tyr Arg Ser Asn Lys Gly Glu Ser Pro Val Glu Pro
1               5                   10                  15

```
Ala Glu Pro Cys His Tyr Ser Cys Pro Arg Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 94
<211> LENGTH: 116
<212> TYPE: PRT
<213> ORGANISM: Artificial Sequence
<220> FEATURE:
<223> OTHER INFORMATION: CD2 intracellular co-stimulatory signaling
      domain

<400> SEQUENCE: 94

```
Lys Arg Lys Lys Gln Arg Ser Arg Arg Asn Asp Glu Glu Leu Glu Thr
1               5                   10                  15

Arg Ala His Arg Val Ala Thr Glu Glu Arg Gly Arg Lys Pro His Gln
            20                  25                  30

Ile Pro Ala Ser Thr Pro Gln Asn Pro Ala Thr Ser Gln His Pro Pro
        35                  40                  45

Pro Pro Pro Gly His Arg Ser Gln Ala Pro Ser His Arg Pro Pro Pro
50                  55                  60

Pro Gly His Arg Val Gln His Gln Pro Gln Lys Arg Pro Pro Ala Pro
65                  70                  75                  80

Ser Gly Thr Gln Val His Gln Gln Lys Gly Pro Pro Leu Pro Arg Pro
                85                  90                  95

Arg Val Gln Pro Lys Pro Pro His Gly Ala Ala Glu Asn Ser Leu Ser
            100                 105                 110

Pro Ser Ser Asn
        115
```

<210> SEQ ID NO 95
<211> LENGTH: 39
<212> TYPE: PRT
<213> ORGANISM: Artificial Sequence
<220> FEATURE:
<223> OTHER INFORMATION: CD7 intracellular co-stimulatory signaling
      domain

<400> SEQUENCE: 95

```
Arg Thr Gln Ile Lys Lys Leu Cys Ser Trp Arg Asp Lys Asn Ser Ala
1               5                   10                  15

Ala Cys Val Val Tyr Glu Asp Met Ser His Ser Arg Cys Asn Thr Leu
            20                  25                  30

Ser Ser Pro Asn Gln Tyr Gln
        35
```

<210> SEQ ID NO 96
<211> LENGTH: 32
<212> TYPE: PRT
<213> ORGANISM: Artificial Sequence
<220> FEATURE:
<223> OTHER INFORMATION: CD8A intracellular co-stimulatory signaling
      domain

<400> SEQUENCE: 96

```
Leu Tyr Cys Asn His Arg Asn Arg Arg Arg Val Cys Lys Cys Pro Arg
1               5                   10                  15

Pro Val Val Lys Ser Gly Asp Lys Pro Ser Leu Ser Ala Arg Tyr Val
            20                  25                  30
```

-continued

```
<210> SEQ ID NO 97
<211> LENGTH: 19
<212> TYPE: PRT
<213> ORGANISM: Artificial Sequence
<220> FEATURE:
<223> OTHER INFORMATION: CD8B intracellular co-stimulatory signaling
      domain

<400> SEQUENCE: 97

His Leu Cys Cys Arg Arg Arg Ala Arg Leu Arg Phe Met Lys Gln
1               5                   10                  15

Phe Tyr Lys

<210> SEQ ID NO 98
<211> LENGTH: 42
<212> TYPE: PRT
<213> ORGANISM: Artificial Sequence
<220> FEATURE:
<223> OTHER INFORMATION: OX40 intracellular co-stimulatory signaling
      domain

<400> SEQUENCE: 98

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 99
<211> LENGTH: 61
<212> TYPE: PRT
<213> ORGANISM: Artificial Sequence
<220> FEATURE:
<223> OTHER INFORMATION: CD226 intracellular co-stimulatory signaling
      domain

<400> SEQUENCE: 99

Asn Arg Arg Arg Arg Glu Arg Arg Asp Leu Phe Thr Glu Ser Trp
1               5                   10                  15

Asp Thr Gln Lys Ala Pro Asn Asn Tyr Arg Ser Pro Ile Ser Thr Ser
            20                  25                  30

Gln Pro Thr Asn Gln Ser Met Asp Asp Thr Arg Glu Asp Ile Tyr Val
        35                  40                  45

Asn Tyr Pro Thr Phe Ser Arg Arg Pro Lys Thr Arg Val
    50                  55                  60

<210> SEQ ID NO 100
<211> LENGTH: 197
<212> TYPE: PRT
<213> ORGANISM: Artificial Sequence
<220> FEATURE:
<223> OTHER INFORMATION: DR3 intracellular co-stimulatory signaling
      domain

<400> SEQUENCE: 100

Thr Tyr Thr Tyr Arg His Cys Trp Pro His Lys Pro Leu Val Thr Ala
1               5                   10                  15

Asp Glu Ala Gly Met Glu Ala Leu Thr Pro Pro Ala Thr His Leu
            20                  25                  30

Ser Pro Leu Asp Ser Ala His Thr Leu Leu Ala Pro Pro Asp Ser Ser
        35                  40                  45
```

```
Glu Lys Ile Cys Thr Val Gln Leu Val Gly Asn Ser Trp Thr Pro Gly
    50                  55                  60

Tyr Pro Glu Thr Gln Glu Ala Leu Cys Pro Val Thr Trp Ser Trp
65                  70                  75                  80

Asp Gln Leu Pro Ser Arg Ala Leu Gly Pro Ala Ala Pro Thr Leu
                85                  90                  95

Ser Pro Glu Ser Pro Ala Gly Ser Pro Ala Met Met Leu Gln Pro Gly
            100                 105                 110

Pro Gln Leu Tyr Asp Val Met Asp Ala Val Pro Ala Arg Arg Trp Lys
            115                 120                 125

Glu Phe Val Arg Thr Leu Gly Leu Arg Glu Ala Glu Ile Glu Ala Val
        130                 135                 140

Glu Val Glu Ile Gly Arg Phe Arg Asp Gln Gln Tyr Glu Met Leu Lys
145                 150                 155                 160

Arg Trp Arg Gln Gln Gln Pro Ala Gly Leu Gly Ala Val Tyr Ala Ala
                165                 170                 175

Leu Glu Arg Met Gly Leu Asp Gly Cys Val Glu Asp Leu Arg Ser Arg
            180                 185                 190

Leu Gln Arg Gly Pro
            195

<210> SEQ ID NO 101
<211> LENGTH: 77
<212> TYPE: PRT
<213> ORGANISM: Artificial Sequence
<220> FEATURE:
<223> OTHER INFORMATION: SLAM intracellular co-stimulatory signaling
      domain

<400> SEQUENCE: 101

Gln Leu Arg Arg Arg Gly Lys Thr Asn His Tyr Gln Thr Thr Val Glu
1               5                   10                  15

Lys Lys Ser Leu Thr Ile Tyr Ala Gln Val Gln Lys Pro Gly Pro Leu
            20                  25                  30

Gln Lys Lys Leu Asp Ser Phe Pro Ala Gln Asp Pro Cys Thr Thr Ile
        35                  40                  45

Tyr Val Ala Ala Thr Glu Pro Val Pro Glu Ser Val Gln Glu Thr Asn
    50                  55                  60

Ser Ile Thr Val Tyr Ala Ser Val Thr Leu Pro Glu Ser
65                  70                  75

<210> SEQ ID NO 102
<211> LENGTH: 29
<212> TYPE: PRT
<213> ORGANISM: Artificial Sequence
<220> FEATURE:
<223> OTHER INFORMATION: ICAM-1 intracellular co-stimulatory signaling
      domain

<400> SEQUENCE: 102

Asn Arg Gln Arg Lys Ile Lys Lys Tyr Arg Leu Gln Gln Ala Gln Lys
1               5                   10                  15

Gly Thr Pro Met Lys Pro Asn Thr Gln Ala Thr Pro Pro
            20                  25

<210> SEQ ID NO 103
<211> LENGTH: 51
<212> TYPE: PRT
<213> ORGANISM: Artificial Sequence
<220> FEATURE:
```

<223> OTHER INFORMATION: NKG2D intracellular co-stimulatory signaling domain

<400> SEQUENCE: 103

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser
    50

<210> SEQ ID NO 104
<211> LENGTH: 70
<212> TYPE: PRT
<213> ORGANISM: Artificial Sequence
<220> FEATURE:
<223> OTHER INFORMATION: NKG2C intracellular co-stimulatory signaling domain

<400> SEQUENCE: 104

Met Ser Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
                20                  25                  30

Gly Thr Glu Gln Glu Ile Phe Gln Val Glu Leu Asn Leu Gln Asn Pro
            35                  40                  45

Ser Leu Asn His Gln Gly Ile Asp Lys Ile Tyr Asp Cys Gln Gly Leu
    50                  55                  60

Leu Pro Pro Pro Glu Lys
65                  70

<210> SEQ ID NO 105
<211> LENGTH: 47
<212> TYPE: PRT
<213> ORGANISM: Artificial Sequence
<220> FEATURE:
<223> OTHER INFORMATION: B7-H3 intracellular co-stimulatory signaling domain

<400> SEQUENCE: 105

Cys Trp Arg Lys Ile Lys Gln Ser Cys Glu Glu Glu Asn Ala Gly Ala
1               5                   10                  15

Glu Asp Gln Asp Gly Glu Gly Glu Gly Ser Lys Thr Ala Leu Gln Pro
                20                  25                  30

Leu Lys His Ser Asp Ser Lys Glu Asp Asp Gly Gln Glu Ile Ala
            35                  40                  45

<210> SEQ ID NO 106
<211> LENGTH: 120
<212> TYPE: PRT
<213> ORGANISM: Artificial Sequence
<220> FEATURE:
<223> OTHER INFORMATION: 2B4 intracellular co-stimulatory signaling domain

<400> SEQUENCE: 106

Trp Arg Arg Lys Arg Lys Glu Lys Gln Ser Glu Thr Ser Pro Lys Glu
1               5                   10                  15

Phe Leu Thr Ile Tyr Glu Asp Val Lys Asp Leu Lys Thr Arg Arg Asn
                20                  25                  30

```
His Gln Glu Gln Thr Phe Pro Gly Gly Gly Ser Thr Ile Tyr Ser
        35                  40                  45

Met Ile Gln Ser Gln Ser Ser Ala Pro Thr Ser Gln Glu Pro Ala Tyr
    50                  55                  60

Thr Leu Tyr Ser Leu Ile Gln Pro Ser Arg Lys Ser Gly Ser Arg Lys
65                  70                  75                  80

Arg Asn His Ser Pro Ser Phe Asn Ser Thr Ile Tyr Glu Val Ile Gly
                85                  90                  95

Lys Ser Gln Pro Lys Ala Gln Asn Pro Ala Arg Leu Ser Arg Lys Glu
                100                 105                 110

Leu Glu Asn Phe Asp Val Tyr Ser
                115                 120

<210> SEQ ID NO 107
<211> LENGTH: 42
<212> TYPE: PRT
<213> ORGANISM: Artificial Sequence
<220> FEATURE:
<223> OTHER INFORMATION: FcepsilonRIgamma intracellular co-stimulatory
      signaling domain; FcepsilonRIgamma intracellular signaling domain

<400> SEQUENCE: 107

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
                20                  25                  30

Glu Thr Leu Lys His Glu Lys Pro Pro Gln
                35                  40

<210> SEQ ID NO 108
<211> LENGTH: 111
<212> TYPE: PRT
<213> ORGANISM: Artificial Sequence
<220> FEATURE:
<223> OTHER INFORMATION: BTLA intracellular co-stimulatory signaling
      domain

<400> SEQUENCE: 108

Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
                20                  25                  30

Ser Thr Arg Gln Asn Ser Gln Val Leu Leu Ser Glu Thr Gly Ile Tyr
                35                  40                  45

Asp Asn Asp Pro Asp Leu Cys Phe Arg Met Gln Glu Gly Ser Glu Val
    50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
                100                 105                 110

<210> SEQ ID NO 109
<211> LENGTH: 58
<212> TYPE: PRT
<213> ORGANISM: Artificial Sequence
<220> FEATURE:
<223> OTHER INFORMATION: GITR intracellular co-stimulatory signaling
      domain
```

<400> SEQUENCE: 109

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55

<210> SEQ ID NO 110
<211> LENGTH: 60
<212> TYPE: PRT
<213> ORGANISM: Artificial Sequence
<220> FEATURE:
<223> OTHER INFORMATION: HVEM intracellular co-stimulatory signaling
      domain

<400> SEQUENCE: 110

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 111
<211> LENGTH: 24
<212> TYPE: PRT
<213> ORGANISM: Artificial Sequence
<220> FEATURE:
<223> OTHER INFORMATION: DAP10 intracellular co-stimulatory signaling
      domain; DAP10 intracellular signaling domain

<400> SEQUENCE: 111

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 112
<211> LENGTH: 52
<212> TYPE: PRT
<213> ORGANISM: Artificial Sequence
<220> FEATURE:
<223> OTHER INFORMATION: DAP12 intracellular co-stimulatory signaling
      domain; DAP-12 intracellular signaling domain

<400> SEQUENCE: 112

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

-continued

```
<210> SEQ ID NO 113
<211> LENGTH: 189
<212> TYPE: PRT
<213> ORGANISM: Artificial Sequence
<220> FEATURE:
<223> OTHER INFORMATION: CD30 intracellular co-stimulatory signaling
      domain

<400> SEQUENCE: 113

Cys His Arg Arg Ala Cys Arg Lys Arg Ile Arg Gln Lys Leu His Leu
1               5                   10                  15

Cys Tyr Pro Val Gln Thr Ser Gln Pro Lys Leu Glu Leu Val Asp Ser
                20                  25                  30

Arg Pro Arg Arg Ser Ser Thr Gln Leu Arg Ser Gly Ala Ser Val Thr
            35                  40                  45

Glu Pro Val Ala Glu Glu Arg Gly Leu Met Ser Gln Pro Leu Met Glu
    50                  55                  60

Thr Cys His Ser Val Gly Ala Ala Tyr Leu Glu Ser Leu Pro Leu Gln
65                  70                  75                  80

Asp Ala Ser Pro Ala Gly Gly Pro Ser Ser Pro Arg Asp Leu Pro Glu
                85                  90                  95

Pro Arg Val Ser Thr Glu His Thr Asn Asn Lys Ile Glu Lys Ile Tyr
            100                 105                 110

Ile Met Lys Ala Asp Thr Val Ile Val Gly Thr Val Lys Ala Glu Leu
        115                 120                 125

Pro Glu Gly Arg Gly Leu Ala Gly Pro Ala Glu Pro Glu Leu Glu Glu
    130                 135                 140

Glu Leu Glu Ala Asp His Thr Pro His Tyr Pro Glu Gln Glu Thr Glu
145                 150                 155                 160

Pro Pro Leu Gly Ser Cys Ser Asp Val Met Leu Ser Val Glu Glu Glu
                165                 170                 175

Gly Lys Glu Asp Pro Leu Pro Thr Ala Ala Ser Gly Lys
            180                 185

<210> SEQ ID NO 114
<211> LENGTH: 62
<212> TYPE: PRT
<213> ORGANISM: Artificial Sequence
<220> FEATURE:
<223> OTHER INFORMATION: CD40 intracellular co-stimulatory signaling
      domain

<400> SEQUENCE: 114

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
            35                  40                  45

Glu Asp Gly Lys Glu Ser Arg Ile Ser Val Gln Glu Arg Gln
    50                  55                  60

<210> SEQ ID NO 115
<211> LENGTH: 22
<212> TYPE: PRT
<213> ORGANISM: Artificial Sequence
<220> FEATURE:
<223> OTHER INFORMATION: CD40L intracellular co-stimulatory signaling
      domain

<400> SEQUENCE: 115
```

```
Met Ile Glu Thr Tyr Asn Gln Thr Ser Pro Arg Ser Ala Ala Thr Gly
1               5                   10                  15

Leu Pro Ile Ser Met Lys
            20
```

<210> SEQ ID NO 116
<211> LENGTH: 48
<212> TYPE: PRT
<213> ORGANISM: Artificial Sequence
<220> FEATURE:
<223> OTHER INFORMATION: TIM1 intracellular co-stimulatory signaling domain

<400> SEQUENCE: 116

```
Lys Lys Tyr Phe Phe Lys Lys Glu Val Gln Gln Leu Ser Val Ser Phe
1               5                   10                  15

Ser Ser Leu Gln Ile Lys Ala Leu Gln Asn Ala Val Glu Lys Glu Val
            20                  25                  30

Gln Ala Glu Asp Asn Ile Tyr Ile Glu Asn Ser Leu Tyr Ala Thr Asp
        35                  40                  45
```

<210> SEQ ID NO 117
<211> LENGTH: 96
<212> TYPE: PRT
<213> ORGANISM: Artificial Sequence
<220> FEATURE:
<223> OTHER INFORMATION: PD-1 intracellular co-stimulatory signaling domain

<400> SEQUENCE: 117

```
Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95
```

<210> SEQ ID NO 118
<211> LENGTH: 59
<212> TYPE: PRT
<213> ORGANISM: Artificial Sequence
<220> FEATURE:
<223> OTHER INFORMATION: LFA-1 intracellular co-stimulatory signaling domain

<400> SEQUENCE: 118

```
Tyr Lys Val Gly Phe Phe Lys Arg Asn Leu Lys Glu Lys Met Glu Ala
1               5                   10                  15

Gly Arg Gly Val Pro Asn Gly Ile Pro Ala Glu Asp Ser Glu Gln Leu
            20                  25                  30

Ala Ser Gly Gln Glu Ala Gly Asp Pro Gly Cys Leu Lys Pro Leu His
        35                  40                  45

Glu Lys Asp Ser Glu Ser Gly Gly Gly Lys Asp
    50                  55
```

-continued

```
<210> SEQ ID NO 119
<211> LENGTH: 182
<212> TYPE: PRT
<213> ORGANISM: Artificial Sequence
<220> FEATURE:
<223> OTHER INFORMATION: LIGHT intracellular co-stimulatory signaling
      domain

<400> SEQUENCE: 119

Leu Gln Leu His Trp Arg Leu Gly Glu Met Val Thr Arg Leu Pro Asp
1               5                   10                  15

Gly Pro Ala Gly Ser Trp Glu Gln Leu Ile Gln Glu Arg Arg Ser His
            20                  25                  30

Glu Val Asn Pro Ala Ala His Leu Thr Gly Ala Asn Ser Ser Leu Thr
        35                  40                  45

Gly Ser Gly Gly Pro Leu Leu Trp Glu Thr Gln Leu Gly Leu Ala Phe
    50                  55                  60

Leu Arg Gly Leu Ser Tyr His Asp Gly Ala Leu Val Val Thr Lys Ala
65                  70                  75                  80

Gly Tyr Tyr Tyr Ile Tyr Ser Lys Val Gln Leu Gly Gly Val Gly Cys
                85                  90                  95

Pro Leu Gly Leu Ala Ser Thr Ile Thr His Gly Leu Tyr Lys Arg Thr
            100                 105                 110

Pro Arg Tyr Pro Glu Glu Leu Glu Leu Leu Val Ser Gln Gln Ser Pro
        115                 120                 125

Cys Gly Arg Ala Thr Ser Ser Ser Arg Val Trp Trp Asp Ser Ser Phe
    130                 135                 140

Leu Gly Gly Val Val His Leu Glu Ala Gly Glu Lys Val Val Val Arg
145                 150                 155                 160

Val Leu Asp Glu Arg Leu Val Arg Leu Arg Asp Gly Thr Arg Ser Tyr
                165                 170                 175

Phe Gly Ala Phe Met Val
            180

<210> SEQ ID NO 120
<211> LENGTH: 82
<212> TYPE: PRT
<213> ORGANISM: Artificial Sequence
<220> FEATURE:
<223> OTHER INFORMATION: JAML intracellular co-stimulatory signaling
      domain

<400> SEQUENCE: 120

Lys Lys Thr Cys Gly Asn Lys Ser Ser Val Asn Ser Thr Val Leu Val
1               5                   10                  15

Phe Glu Arg Cys Glu Gly Glu Lys His Ile Tyr Ser Pro Ile Ile Val
            20                  25                  30

Arg Glu Val Ile Glu Glu Glu Pro Ser Glu Lys Ser Glu Ala Thr
        35                  40                  45

Tyr Met Thr Met His Pro Val Trp Pro Ser Leu Arg Ser Asp Arg Asn
    50                  55                  60

Asn Ser Leu Glu Lys Lys Ser Gly Gly Gly Met Pro Lys Thr Gln Gln
65                  70                  75                  80

Ala Phe

<210> SEQ ID NO 121
<211> LENGTH: 107
<212> TYPE: PRT
```

```
<213> ORGANISM: Artificial Sequence
<220> FEATURE:
<223> OTHER INFORMATION: CD100 intracellular co-stimulatory signaling
      domain

<400> SEQUENCE: 121

Tyr Lys Gly Tyr Leu Pro Arg Gln Cys Leu Lys Phe Arg Ser Ala Leu
1               5                   10                  15

Leu Ile Gly Lys Lys Pro Lys Ser Asp Phe Cys Asp Arg Glu Gln
            20                  25                  30

Ser Leu Lys Glu Thr Leu Val Glu Pro Gly Ser Phe Ser Gln Gln Asn
            35                  40                  45

Gly Glu His Pro Lys Pro Ala Leu Asp Thr Gly Tyr Glu Thr Glu Gln
        50                  55                  60

Asp Thr Ile Thr Ser Lys Val Pro Thr Asp Arg Glu Asp Ser Gln Arg
65                  70                  75                  80

Ile Asp Asp Leu Ser Ala Arg Asp Lys Pro Phe Asp Val Lys Cys Glu
                85                  90                  95

Leu Lys Phe Ala Asp Ser Asp Ala Asp Gly Asp
            100                 105

<210> SEQ ID NO 122
<211> LENGTH: 38
<212> TYPE: PRT
<213> ORGANISM: Artificial Sequence
<220> FEATURE:
<223> OTHER INFORMATION: ICOS intracellular co-stimulatory signaling
      domain

<400> SEQUENCE: 122

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
            35

<210> SEQ ID NO 123
<211> LENGTH: 296
<212> TYPE: PRT
<213> ORGANISM: Artificial Sequence
<220> FEATURE:
<223> OTHER INFORMATION: MyD88 intracellular co-stimulatory signaling
      domain

<400> SEQUENCE: 123

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110
```

```
Cys Gln Lys Tyr Ile Leu Lys Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
    290                 295

<210> SEQ ID NO 124
<211> LENGTH: 112
<212> TYPE: PRT
<213> ORGANISM: Artificial Sequence
<220> FEATURE:
<223> OTHER INFORMATION: CD3zeta intracellular signaling domain

<400> SEQUENCE: 124

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

<210> SEQ ID NO 125
<211> LENGTH: 45
<212> TYPE: PRT
<213> ORGANISM: Artificial Sequence
<220> FEATURE:
<223> OTHER INFORMATION: CD3delta intracellular signaling domain

<400> SEQUENCE: 125

Gly His Glu Thr Gly Arg Leu Ser Gly Ala Ala Asp Thr Gln Ala Leu
```

```
                1               5                  10                  15
Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys
        35                  40                  45
```

<210> SEQ ID NO 126
<211> LENGTH: 45
<212> TYPE: PRT
<213> ORGANISM: Artificial Sequence
<220> FEATURE:
<223> OTHER INFORMATION: CD3gamma intracellular signaling domain

<400> SEQUENCE: 126

```
Gly Gln Asp Gly Val Arg Gln Ser Arg Ala Ser Asp Lys Gln Thr Leu
1               5                   10                  15

Leu Pro Asn Asp Gln Leu Tyr Gln Pro Leu Lys Asp Arg Glu Asp Asp
            20                  25                  30

Gln Tyr Ser His Leu Gln Gly Asn Gln Leu Arg Arg Asn
        35                  40                  45
```

<210> SEQ ID NO 127
<211> LENGTH: 55
<212> TYPE: PRT
<213> ORGANISM: Artificial Sequence
<220> FEATURE:
<223> OTHER INFORMATION: CD3epsilon intracellular signaling domain

<400> SEQUENCE: 127

```
Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55
```

<210> SEQ ID NO 128
<211> LENGTH: 61
<212> TYPE: PRT
<213> ORGANISM: Artificial Sequence
<220> FEATURE:
<223> OTHER INFORMATION: CD79a intracellular signaling domain

<400> SEQUENCE: 128

```
Arg Lys Arg Trp Gln Asn Glu Lys Leu Gly Leu Asp Ala Gly Asp Glu
1               5                   10                  15

Tyr Glu Asp Glu Asn Leu Tyr Glu Gly Leu Asn Leu Asp Asp Cys Ser
            20                  25                  30

Met Tyr Glu Asp Ile Ser Arg Gly Leu Gln Gly Thr Tyr Gln Asp Val
        35                  40                  45

Gly Ser Leu Asn Ile Gly Asp Val Gln Leu Glu Lys Pro
    50                  55                  60
```

<210> SEQ ID NO 129
<211> LENGTH: 49
<212> TYPE: PRT
<213> ORGANISM: Artificial Sequence
<220> FEATURE:
<223> OTHER INFORMATION: CD79b intracellular signaling domain

```
<400> SEQUENCE: 129

Leu Asp Lys Asp Asp Ser Lys Ala Gly Met Glu Glu Asp His Thr Tyr
1               5                   10                  15

Glu Gly Leu Asp Ile Asp Gln Thr Ala Thr Tyr Glu Asp Ile Val Thr
            20                  25                  30

Leu Arg Thr Gly Glu Val Lys Trp Ser Val Gly Glu His Pro Gly Gln
        35                  40                  45

Glu

<210> SEQ ID NO 130
<211> LENGTH: 44
<212> TYPE: PRT
<213> ORGANISM: Artificial Sequence
<220> FEATURE:
<223> OTHER INFORMATION: FcepsilonRIbeta intracellular signaling domain

<400> SEQUENCE: 130

Ile Cys Gly Ala Gly Glu Glu Leu Lys Gly Asn Lys Val Pro Glu Asp
1               5                   10                  15

Arg Val Tyr Glu Glu Leu Asn Ile Tyr Ser Ala Thr Tyr Ser Glu Leu
            20                  25                  30

Glu Asp Pro Gly Glu Met Ser Pro Pro Ile Asp Leu
        35                  40

<210> SEQ ID NO 131
<211> LENGTH: 77
<212> TYPE: PRT
<213> ORGANISM: Artificial Sequence
<220> FEATURE:
<223> OTHER INFORMATION: Fc?RIIa intracellular signaling domain

<400> SEQUENCE: 131

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Leu Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75

<210> SEQ ID NO 132
<211> LENGTH: 58
<212> TYPE: PRT
<213> ORGANISM: Artificial Sequence
<220> FEATURE:
<223> OTHER INFORMATION: bovine leukemia virus gp30 intracellular
      signaling domain

<400> SEQUENCE: 132

Lys Cys Leu Thr Ser Arg Leu Leu Lys Leu Leu Arg Gln Ala Pro His
1               5                   10                  15

Phe Pro Glu Ile Ser Phe Pro Pro Lys Pro Asp Ser Asp Tyr Gln Ala
            20                  25                  30

Leu Leu Pro Ser Ala Pro Glu Ile Tyr Ser His Leu Ser Pro Thr Lys
        35                  40                  45

Pro Asp Tyr Ile Asn Leu Arg Pro Cys Pro
    50                  55
```

<210> SEQ ID NO 133
<211> LENGTH: 112
<212> TYPE: PRT
<213> ORGANISM: Artificial Sequence
<220> FEATURE:
<223> OTHER INFORMATION: Epstein-Barr Virus (EBV) LMP2A intracellular
     signaling domain

<400> SEQUENCE: 133

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

<210> SEQ ID NO 134
<211> LENGTH: 260
<212> TYPE: PRT
<213> ORGANISM: Artificial Sequence
<220> FEATURE:
<223> OTHER INFORMATION: Simian immunodeficiency virus PBj14 Nef
     intracellular signaling domain

<400> SEQUENCE: 134

Gly Gly Val Thr Ser Lys Lys Gln Arg Arg Gly Gly Asn Leu Tyr
1               5                   10                  15

Glu Arg Leu Leu Gln Ala Arg Gly Glu Thr Tyr Gly Arg Leu Trp Glu
            20                  25                  30

Gly Leu Glu Gly Glu Tyr Ser Gln Ser Gln Asp Ala Ser Gly Lys Gly
        35                  40                  45

Leu Ser Ser Leu Ser Cys Glu Pro Gln Lys Tyr Cys Glu Gly Gln Phe
    50                  55                  60

Met Asn Thr Pro Trp Arg Asn Pro Ala Thr Glu Arg Ala Lys Leu Asp
65                  70                  75                  80

Tyr Arg Gln Gln Asn Met Asp Asp Val Asp Ser Ala Asp Leu Val Gly
                85                  90                  95

Cys Pro Val Ser Pro Arg Val Pro Val Arg Ile Met Thr Tyr Lys Leu
            100                 105                 110

Ala Ile Asp Met Ser His Phe Ile Lys Glu Lys Gly Gly Leu Glu Gly
        115                 120                 125

Ile Tyr Tyr Ser Asp Arg Arg His Lys Ile Leu Asp Leu Tyr Leu Glu
    130                 135                 140

Lys Glu Glu Gly Ile Ile Pro Asp Trp Gln Asn Tyr Thr Ala Gly Pro
145                 150                 155                 160

Gly Ile Arg Tyr Pro Met Phe Phe Gly Trp Leu Trp Lys Leu Val Pro
                165                 170                 175

Val Asn Val Ser Asp Glu Ala Gln Glu Asp Glu Thr His Tyr Leu Met
            180                 185                 190

```
His Pro Ala Gln Thr Ser Gln Trp Asp Asp Pro Trp Gly Glu Val Leu
            195                 200                 205

Ala Trp Lys Phe Asp Pro Lys Leu Ala Tyr Asn Tyr Lys Ala Phe Val
        210                 215                 220

Glu His Pro Glu Glu Phe Gly Ser Gln Ser Gly Leu Ser Lys Glu Glu
225                 230                 235                 240

Val Gln Arg Arg Leu Thr Ala Arg Gly Leu Leu Lys Met Ala Asp Lys
                245                 250                 255

Lys Lys Thr Ser
            260

<210> SEQ ID NO 135
<211> LENGTH: 134
<212> TYPE: PRT
<213> ORGANISM: Artificial Sequence
<220> FEATURE:
<223> OTHER INFORMATION: CD28 hinge region

<400> SEQUENCE: 135

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 136
<211> LENGTH: 220
<212> TYPE: PRT
<213> ORGANISM: Artificial Sequence
<220> FEATURE:
<223> OTHER INFORMATION: IgG1 hinge region

<400> SEQUENCE: 136

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
```

```
                    85                  90                  95
Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
        210                 215                 220

<210> SEQ ID NO 137
<211> LENGTH: 217
<212> TYPE: PRT
<213> ORGANISM: Artificial Sequence
<220> FEATURE:
<223> OTHER INFORMATION: IgG4 hinge region

<400> SEQUENCE: 137

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

```
<210> SEQ ID NO 138
<211> LENGTH: 223
<212> TYPE: PRT
<213> ORGANISM: Artificial Sequence
<220> FEATURE:
<223> OTHER INFORMATION: IgD hinge region

<400> SEQUENCE: 138

Cys Pro Ser His Thr Gln Pro Leu Gly Val Tyr Leu Leu Thr Pro Ala
1               5                   10                  15

Val Gln Asp Leu Trp Leu Arg Asp Lys Ala Thr Phe Thr Cys Phe Val
            20                  25                  30

Val Gly Ser Asp Leu Lys Asp Ala His Leu Thr Trp Glu Val Ala Gly
        35                  40                  45

Lys Val Pro Thr Gly Gly Val Glu Glu Gly Leu Leu Glu Arg His Ser
    50                  55                  60

Asn Gly Ser Gln Ser Gln His Ser Arg Leu Thr Leu Pro Arg Ser Leu
65                  70                  75                  80

Trp Asn Ala Gly Thr Ser Val Thr Cys Thr Leu Asn His Pro Ser Leu
                85                  90                  95

Pro Pro Gln Arg Leu Met Ala Leu Arg Glu Pro Ala Gln Ala Pro Val
            100                 105                 110

Lys Leu Ser Leu Asn Leu Leu Ala Ser Ser Asp Pro Pro Glu Ala Ala
        115                 120                 125

Ser Trp Leu Leu Cys Glu Val Ser Gly Phe Ser Pro Pro Asn Ile Leu
    130                 135                 140

Leu Met Trp Leu Glu Asp Gln Arg Glu Val Asn Thr Ser Gly Phe Ala
145                 150                 155                 160

Pro Ala Arg Pro Pro Pro Gln Pro Arg Ser Thr Thr Phe Trp Ala Trp
                165                 170                 175

Ser Val Leu Arg Val Pro Ala Pro Pro Ser Pro Gln Pro Ala Thr Tyr
            180                 185                 190

Thr Cys Val Val Ser His Glu Asp Ser Arg Thr Leu Leu Asn Ala Ser
        195                 200                 205

Arg Ser Leu Glu Val Ser Tyr Val Thr Asp His Gly Pro Met Lys
    210                 215                 220

<210> SEQ ID NO 139
<211> LENGTH: 163
<212> TYPE: PRT
<213> ORGANISM: Artificial Sequence
<220> FEATURE:
<223> OTHER INFORMATION: 4-1BB hinge region

<400> SEQUENCE: 139

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95
```

```
Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
        130                 135                 140

Gly Ala Ser Ser Val Thr Pro Pro Ala Pro Ala Arg Glu Pro Gly His
145                 150                 155                 160

Ser Pro Gln

<210> SEQ ID NO 140
<211> LENGTH: 371
<212> TYPE: PRT
<213> ORGANISM: Artificial Sequence
<220> FEATURE:
<223> OTHER INFORMATION: CD4 hinge region

<400> SEQUENCE: 140

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
            195                 200                 205

Gly Ser Gly Glu Leu Trp Trp Gln Ala Glu Arg Ala Ser Ser Ser Lys
        210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
            275                 280                 285

Leu Val Val Met Arg Ala Thr Gln Leu Gln Lys Asn Leu Thr Cys Glu
```

```
                290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
                340                 345                 350

Val Leu Leu Glu Ser Asn Ile Lys Val Leu Pro Thr Trp Ser Thr Pro
            355                 360                 365

Val Gln Pro
    370

<210> SEQ ID NO 141
<211> LENGTH: 172
<212> TYPE: PRT
<213> ORGANISM: Artificial Sequence
<220> FEATURE:
<223> OTHER INFORMATION: CD27 hinge region

<400> SEQUENCE: 141

Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg
                165                 170

<210> SEQ ID NO 142
<211> LENGTH: 155
<212> TYPE: PRT
<213> ORGANISM: Artificial Sequence
<220> FEATURE:
<223> OTHER INFORMATION: CD7 hinge region

<400> SEQUENCE: 142

Ala Gln Glu Val Gln Gln Ser Pro His Cys Thr Thr Val Pro Val Gly
1               5                   10                  15

Ala Ser Val Asn Ile Thr Cys Ser Thr Ser Gly Gly Leu Arg Gly Ile
            20                  25                  30

Tyr Leu Arg Gln Leu Gly Pro Gln Pro Gln Asp Ile Ile Tyr Tyr Glu
        35                  40                  45
```

```
Asp Gly Val Val Pro Thr Thr Asp Arg Arg Phe Arg Gly Arg Ile Asp
 50                  55                  60
Phe Ser Gly Ser Gln Asp Asn Leu Thr Ile Thr Met His Arg Leu Gln
 65                  70                  75                  80
Leu Ser Asp Thr Gly Thr Tyr Thr Cys Gln Ala Ile Thr Glu Val Asn
                 85                  90                  95
Val Tyr Gly Ser Gly Thr Leu Val Leu Val Thr Glu Glu Gln Ser Gln
                100                 105                 110
Gly Trp His Arg Cys Ser Asp Ala Pro Arg Ala Ser Ala Leu Pro
            115                 120                 125
Ala Pro Pro Thr Gly Ser Ala Leu Pro Asp Pro Gln Thr Ala Ser Ala
    130                 135                 140
Leu Pro Asp Pro Pro Ala Ala Ser Ala Leu Pro
145                 150                 155
```

<210> SEQ ID NO 143
<211> LENGTH: 161
<212> TYPE: PRT
<213> ORGANISM: Artificial Sequence
<220> FEATURE:
<223> OTHER INFORMATION: CD8A hinge region

<400> SEQUENCE: 143

```
Ser Gln Phe Arg Val Ser Pro Leu Asp Arg Thr Trp Asn Leu Gly Glu
  1               5                  10                  15
Thr Val Glu Leu Lys Cys Gln Val Leu Leu Ser Asn Pro Thr Ser Gly
                 20                  25                  30
Cys Ser Trp Leu Phe Gln Pro Arg Gly Ala Ala Ala Ser Pro Thr Phe
             35                  40                  45
Leu Leu Tyr Leu Ser Gln Asn Lys Pro Lys Ala Ala Glu Gly Leu Asp
     50                  55                  60
Thr Gln Arg Phe Ser Gly Lys Arg Leu Gly Asp Thr Phe Val Leu Thr
 65                  70                  75                  80
Leu Ser Asp Phe Arg Arg Glu Asn Glu Gly Tyr Tyr Phe Cys Ser Ala
                 85                  90                  95
Leu Ser Asn Ser Ile Met Tyr Phe Ser His Phe Val Pro Val Phe Leu
                100                 105                 110
Pro Ala Lys Pro Thr Thr Thr Pro Ala Pro Arg Pro Pro Thr Pro Ala
            115                 120                 125
Pro Thr Ile Ala Ser Gln Pro Leu Ser Leu Arg Pro Glu Ala Cys Arg
    130                 135                 140
Pro Ala Ala Gly Gly Ala Val His Thr Arg Gly Leu Asp Phe Ala Cys
145                 150                 155                 160
Asp
```

<210> SEQ ID NO 144
<211> LENGTH: 147
<212> TYPE: PRT
<213> ORGANISM: Artificial Sequence
<220> FEATURE:
<223> OTHER INFORMATION: PD-1 hinge region

<400> SEQUENCE: 144

```
Phe Leu Asp Ser Pro Asp Arg Pro Trp Asn Pro Pro Thr Phe Ser Pro
  1               5                  10                  15
Ala Leu Leu Val Val Thr Glu Gly Asp Asn Ala Thr Phe Thr Cys Ser
                 20                  25                  30
```

```
Phe Ser Asn Thr Ser Glu Ser Phe Val Leu Asn Trp Tyr Arg Met Ser
         35                  40                  45

Pro Ser Asn Gln Thr Asp Lys Leu Ala Ala Phe Pro Glu Asp Arg Ser
 50                  55                  60

Gln Pro Gly Gln Asp Cys Arg Phe Arg Val Thr Gln Leu Pro Asn Gly
 65                  70                  75                  80

Arg Asp Phe His Met Ser Val Val Arg Ala Arg Arg Asn Asp Ser Gly
                 85                  90                  95

Thr Tyr Leu Cys Gly Ala Ile Ser Leu Ala Pro Lys Ala Gln Ile Lys
            100                 105                 110

Glu Ser Leu Arg Ala Glu Leu Arg Val Thr Glu Arg Arg Ala Glu Val
            115                 120                 125

Pro Thr Ala His Pro Ser Pro Ser Pro Arg Pro Ala Gly Gln Phe Gln
            130                 135                 140

Thr Leu Val
145

<210> SEQ ID NO 145
<211> LENGTH: 120
<212> TYPE: PRT
<213> ORGANISM: Artificial Sequence
<220> FEATURE:
<223> OTHER INFORMATION: ICOS hinge region

<400> SEQUENCE: 145

Glu Ile Asn Gly Ser Ala Asn Tyr Glu Met Phe Ile Phe His Asn Gly
 1               5                  10                  15

Gly Val Gln Ile Leu Cys Lys Tyr Pro Asp Ile Val Gln Gln Phe Lys
                 20                  25                  30

Met Gln Leu Leu Lys Gly Gly Gln Ile Leu Cys Asp Leu Thr Lys Thr
             35                  40                  45

Lys Gly Ser Gly Asn Thr Val Ser Ile Lys Ser Leu Lys Phe Cys His
 50                  55                  60

Ser Gln Leu Ser Asn Asn Ser Val Ser Phe Phe Leu Tyr Asn Leu Asp
 65                  70                  75                  80

His Ser His Ala Asn Tyr Tyr Phe Cys Asn Leu Ser Ile Phe Asp Pro
                 85                  90                  95

Pro Pro Phe Lys Val Thr Leu Thr Gly Gly Tyr Leu His Ile Tyr Glu
            100                 105                 110

Ser Gln Leu Cys Cys Gln Leu Lys
            115                 120

<210> SEQ ID NO 146
<211> LENGTH: 133
<212> TYPE: PRT
<213> ORGANISM: Artificial Sequence
<220> FEATURE:
<223> OTHER INFORMATION: OX40 hinge region

<400> SEQUENCE: 146

Gln Val Ser His Arg Tyr Pro Arg Ile Gln Ser Ile Lys Val Gln Phe
 1               5                  10                  15

Thr Glu Tyr Lys Lys Glu Lys Gly Phe Ile Leu Thr Ser Gln Lys Glu
                 20                  25                  30

Asp Glu Ile Met Lys Val Gln Asn Asn Ser Val Ile Ile Asn Cys Asp
             35                  40                  45

Gly Phe Tyr Leu Ile Ser Leu Lys Gly Tyr Phe Ser Gln Glu Val Asn
 50                  55                  60
```

```
Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 147
<211> LENGTH: 144
<212> TYPE: PRT
<213> ORGANISM: Artificial Sequence
<220> FEATURE:
<223> OTHER INFORMATION: NKG2D hinge region

<400> SEQUENCE: 147

Ile Trp Ser Ala Val Phe Leu Asn Ser Leu Phe Asn Gln Glu Val Gln
1               5                   10                  15

Ile Pro Leu Thr Glu Ser Tyr Cys Gly Pro Cys Pro Lys Asn Trp Ile
            20                  25                  30

Cys Tyr Lys Asn Asn Cys Tyr Gln Phe Phe Asp Glu Ser Lys Asn Trp
        35                  40                  45

Tyr Glu Ser Gln Ala Ser Cys Met Ser Gln Asn Ala Ser Leu Leu Lys
    50                  55                  60

Val Tyr Ser Lys Glu Asp Gln Asp Leu Leu Lys Leu Val Lys Ser Tyr
65                  70                  75                  80

His Trp Met Gly Leu Val His Ile Pro Thr Asn Gly Ser Trp Gln Trp
                85                  90                  95

Glu Asp Gly Ser Ile Leu Ser Pro Asn Leu Leu Thr Ile Ile Glu Met
            100                 105                 110

Gln Lys Gly Asp Cys Ala Leu Tyr Ala Ser Ser Phe Lys Gly Tyr Ile
        115                 120                 125

Glu Asn Cys Ser Thr Pro Asn Thr Tyr Ile Cys Met Gln Arg Thr Val
    130                 135                 140

<210> SEQ ID NO 148
<211> LENGTH: 138
<212> TYPE: PRT
<213> ORGANISM: Artificial Sequence
<220> FEATURE:
<223> OTHER INFORMATION: NKG2C hinge region

<400> SEQUENCE: 148

Ile Pro Phe Leu Glu Gln Asn Asn Ser Ser Pro Asn Thr Arg Thr Gln
1               5                   10                  15

Lys Ala Arg His Cys Gly His Cys Pro Glu Glu Trp Ile Thr Tyr Ser
            20                  25                  30

Asn Ser Cys Tyr Tyr Ile Gly Lys Glu Arg Arg Thr Trp Glu Glu Ser
        35                  40                  45

Leu Leu Ala Cys Thr Ser Lys Asn Ser Ser Leu Leu Ser Ile Asp Asn
    50                  55                  60

Glu Glu Glu Met Lys Phe Leu Ala Ser Ile Leu Pro Ser Ser Trp Ile
65                  70                  75                  80

Gly Val Phe Arg Asn Ser Ser His His Pro Trp Val Thr Ile Asn Gly
```

```
                    85                  90                  95

Leu Ala Phe Lys His Lys Ile Lys Asp Ser Asp Asn Ala Glu Leu Asn
                   100                 105                 110

Cys Ala Val Leu Gln Val Asn Arg Leu Lys Ser Ala Gln Cys Gly Ser
            115                 120                 125

Ser Met Ile Tyr His Cys Lys His Lys Leu
    130                 135

<210> SEQ ID NO 149
<211> LENGTH: 5
<212> TYPE: PRT
<213> ORGANISM: Artificial Sequence
<220> FEATURE:
<223> OTHER INFORMATION: FcepsilonRIgamma hinge region

<400> SEQUENCE: 149

Leu Gly Glu Pro Gln
1               5

<210> SEQ ID NO 150
<211> LENGTH: 127
<212> TYPE: PRT
<213> ORGANISM: Artificial Sequence
<220> FEATURE:
<223> OTHER INFORMATION: BTLA hinge region

<400> SEQUENCE: 150

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
                20                  25                  30

Cys Ala Asn Arg Pro His Val Thr Trp Cys Lys Leu Asn Gly Thr Thr
            35                  40                  45

Cys Val Lys Leu Glu Asp Arg Gln Thr Ser Trp Lys Glu Glu Lys Asn
        50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
                100                 105                 110

Pro Ser Lys Asp Glu Met Ala Ser Arg Pro Trp Leu Leu Tyr Arg
            115                 120                 125

<210> SEQ ID NO 151
<211> LENGTH: 137
<212> TYPE: PRT
<213> ORGANISM: Artificial Sequence
<220> FEATURE:
<223> OTHER INFORMATION: GITR hinge region

<400> SEQUENCE: 151

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
        50                  55                  60
```

```
Arg His His Pro Cys Pro Gly Gln Gly Val Gln Ser Gln Gly Lys
 65                  70                  75                  80

Phe Ser Phe Gly Phe Gln Cys Ile Asp Cys Ala Ser Gly Thr Phe Ser
                 85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro
    130                 135

<210> SEQ ID NO 152
<211> LENGTH: 30
<212> TYPE: PRT
<213> ORGANISM: Artificial Sequence
<220> FEATURE:
<223> OTHER INFORMATION: DAP10 hinge region

<400> SEQUENCE: 152

Gln Thr Thr Pro Gly Glu Arg Ser Ser Leu Pro Ala Phe Tyr Pro Gly
  1               5                  10                  15

Thr Ser Gly Ser Cys Ser Gly Cys Gly Ser Leu Ser Leu Pro
             20                  25                  30

<210> SEQ ID NO 153
<211> LENGTH: 275
<212> TYPE: PRT
<213> ORGANISM: Artificial Sequence
<220> FEATURE:
<223> OTHER INFORMATION: TIM1 hinge region

<400> SEQUENCE: 153

Ser Val Lys Val Gly Gly Glu Ala Gly Pro Ser Val Thr Leu Pro Cys
  1               5                  10                  15

His Tyr Ser Gly Ala Val Thr Ser Met Cys Trp Asn Arg Gly Ser Cys
             20                  25                  30

Ser Leu Phe Thr Cys Gln Asn Gly Ile Val Trp Thr Asn Gly Thr His
         35                  40                  45

Val Thr Tyr Arg Lys Asp Thr Arg Tyr Lys Leu Leu Gly Asp Leu Ser
 50                  55                  60

Arg Arg Asp Val Ser Leu Thr Ile Glu Asn Thr Ala Val Ser Asp Ser
 65                  70                  75                  80

Gly Val Tyr Cys Cys Arg Val Glu His Arg Gly Trp Phe Asn Asp Met
                 85                  90                  95

Lys Ile Thr Val Ser Leu Glu Ile Val Pro Pro Lys Val Thr Thr Thr
            100                 105                 110

Pro Ile Val Thr Thr Val Pro Thr Val Thr Val Arg Thr Ser Thr
        115                 120                 125

Thr Val Pro Thr Thr Thr Thr Val Pro Met Thr Thr Val Pro Thr Thr
        130                 135                 140

Thr Val Pro Thr Thr Met Ser Ile Pro Thr Thr Thr Thr Val Leu Thr
145                 150                 155                 160

Thr Met Thr Val Ser Thr Thr Thr Ser Val Pro Thr Thr Thr Ser Ile
                165                 170                 175

Pro Thr Thr Thr Ser Val Pro Val Thr Thr Thr Val Ser Thr Phe Val
                180                 185                 190

Pro Pro Met Pro Leu Pro Arg Gln Asn His Glu Pro Val Ala Thr Ser
```

```
                195                 200                 205
Pro Ser Ser Pro Gln Pro Ala Glu Thr His Pro Thr Thr Leu Gln Gly
    210                 215                 220

Ala Ile Arg Arg Glu Pro Thr Ser Ser Pro Leu Tyr Ser Tyr Thr Thr
225                 230                 235                 240

Asp Gly Asn Asp Thr Val Thr Glu Ser Ser Asp Gly Leu Trp Asn Asn
                245                 250                 255

Asn Gln Thr Gln Leu Phe Leu Glu His Ser Leu Leu Thr Ala Asn Thr
    260                 265                 270

Thr Lys Gly
    275

<210> SEQ ID NO 154
<211> LENGTH: 217
<212> TYPE: PRT
<213> ORGANISM: Artificial Sequence
<220> FEATURE:
<223> OTHER INFORMATION: SLAM hinge region

<400> SEQUENCE: 154

Ala Ser Tyr Gly Thr Gly Gly Arg Met Met Asn Cys Pro Lys Ile Leu
1               5                   10                  15

Arg Gln Leu Gly Ser Lys Val Leu Leu Pro Leu Thr Tyr Glu Arg Ile
            20                  25                  30

Asn Lys Ser Met Asn Lys Ser Ile His Ile Val Val Thr Met Ala Lys
        35                  40                  45

Ser Leu Glu Asn Ser Val Glu Asn Lys Ile Val Ser Leu Asp Pro Ser
    50                  55                  60

Glu Ala Gly Pro Pro Arg Tyr Leu Gly Asp Arg Tyr Lys Phe Tyr Leu
65                  70                  75                  80

Glu Asn Leu Thr Leu Gly Ile Arg Glu Ser Arg Lys Glu Asp Glu Gly
            85                  90                  95

Trp Tyr Leu Met Thr Leu Glu Lys Asn Val Ser Val Gln Arg Phe Cys
        100                 105                 110

Leu Gln Leu Arg Leu Tyr Glu Gln Val Ser Thr Pro Glu Ile Lys Val
    115                 120                 125

Leu Asn Lys Thr Gln Glu Asn Gly Thr Cys Thr Leu Ile Leu Gly Cys
130                 135                 140

Thr Val Glu Lys Gly Asp His Val Ala Tyr Ser Trp Ser Glu Lys Ala
145                 150                 155                 160

Gly Thr His Pro Leu Asn Pro Ala Asn Ser Ser His Leu Leu Ser Leu
            165                 170                 175

Thr Leu Gly Pro Gln His Ala Asp Asn Ile Tyr Ile Cys Thr Val Ser
        180                 185                 190

Asn Pro Ile Ser Asn Asn Ser Gln Thr Phe Ser Pro Trp Pro Gly Cys
    195                 200                 205

Arg Thr Asp Pro Ser Glu Thr Lys Pro
    210                 215

<210> SEQ ID NO 155
<211> LENGTH: 367
<212> TYPE: PRT
<213> ORGANISM: Artificial Sequence
<220> FEATURE:
<223> OTHER INFORMATION: CD30 hinge region

<400> SEQUENCE: 155
```

Phe Pro Gln Asp Arg Pro Phe Glu Asp Thr Cys His Gly Asn Pro Ser
1               5                   10                  15

His Tyr Tyr Asp Lys Ala Val Arg Arg Cys Cys Tyr Arg Cys Pro Met
            20                  25                  30

Gly Leu Phe Pro Thr Gln Gln Cys Pro Gln Arg Pro Thr Asp Cys Arg
        35                  40                  45

Lys Gln Cys Glu Pro Asp Tyr Tyr Leu Asp Glu Ala Asp Arg Cys Thr
    50                  55                  60

Ala Cys Val Thr Cys Ser Arg Asp Asp Leu Val Glu Lys Thr Pro Cys
65                  70                  75                  80

Ala Trp Asn Ser Ser Arg Val Cys Glu Cys Arg Pro Gly Met Phe Cys
                85                  90                  95

Ser Thr Ser Ala Val Asn Ser Cys Ala Arg Cys Phe Phe His Ser Val
            100                 105                 110

Cys Pro Ala Gly Met Ile Val Lys Phe Pro Gly Thr Ala Gln Lys Asn
        115                 120                 125

Thr Val Cys Glu Pro Ala Ser Pro Gly Val Ser Pro Ala Cys Ala Ser
    130                 135                 140

Pro Glu Asn Cys Lys Glu Pro Ser Ser Gly Thr Ile Pro Gln Ala Lys
145                 150                 155                 160

Pro Thr Pro Val Ser Pro Ala Thr Ser Ser Ala Ser Thr Met Pro Val
                165                 170                 175

Arg Gly Gly Thr Arg Leu Ala Gln Glu Ala Ala Ser Lys Leu Thr Arg
            180                 185                 190

Ala Pro Asp Ser Pro Ser Ser Val Gly Arg Pro Ser Ser Asp Pro Gly
        195                 200                 205

Leu Ser Pro Thr Gln Pro Cys Pro Glu Gly Ser Gly Asp Cys Arg Lys
210                 215                 220

Gln Cys Glu Pro Asp Tyr Tyr Leu Asp Glu Ala Gly Arg Cys Thr Ala
225                 230                 235                 240

Cys Val Ser Cys Ser Arg Asp Asp Leu Val Glu Lys Thr Pro Cys Ala
                245                 250                 255

Trp Asn Ser Ser Arg Thr Cys Glu Cys Arg Pro Gly Met Ile Cys Ala
            260                 265                 270

Thr Ser Ala Thr Asn Ser Cys Ala Arg Cys Val Pro Tyr Pro Ile Cys
        275                 280                 285

Ala Ala Glu Thr Val Thr Lys Pro Gln Asp Met Ala Glu Lys Asp Thr
        290                 295                 300

Thr Phe Glu Ala Pro Pro Leu Gly Thr Gln Pro Asp Cys Asn Pro Thr
305                 310                 315                 320

Pro Glu Asn Gly Glu Ala Pro Ala Ser Thr Ser Pro Thr Gln Ser Leu
                325                 330                 335

Leu Val Asp Ser Gln Ala Ser Lys Thr Leu Pro Ile Pro Thr Ser Ala
            340                 345                 350

Pro Val Ala Leu Ser Ser Thr Gly Lys Pro Val Leu Asp Ala Gly
        355                 360                 365

<210> SEQ ID NO 156
<211> LENGTH: 37
<212> TYPE: PRT
<213> ORGANISM: Artificial Sequence
<220> FEATURE:
<223> OTHER INFORMATION: LIGHT hinge region

<400> SEQUENCE: 156

Met Glu Glu Ser Val Val Arg Pro Ser Val Phe Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg
            35

<210> SEQ ID NO 157
<211> LENGTH: 20
<212> TYPE: RNA
<213> ORGANISM: Artificial Sequence
<220> FEATURE:
<223> OTHER INFORMATION: TRAC sg9

<400> SEQUENCE: 157
agagucucuc agcugguaca                                          20

<210> SEQ ID NO 158
<211> LENGTH: 20
<212> TYPE: RNA
<213> ORGANISM: Artificial Sequence
<220> FEATURE:
<223> OTHER INFORMATION: TRAC sg10

<400> SEQUENCE: 158
ugugcuagac augaggucua                                          20

<210> SEQ ID NO 159
<211> LENGTH: 20
<212> TYPE: RNA
<213> ORGANISM: Artificial Sequence
<220> FEATURE:
<223> OTHER INFORMATION: TRAC sg11

<400> SEQUENCE: 159
cucucagcug guacacggca                                          20

<210> SEQ ID NO 160
<211> LENGTH: 20
<212> TYPE: RNA
<213> ORGANISM: Artificial Sequence
<220> FEATURE:
<223> OTHER INFORMATION: TRAC sg12

<400> SEQUENCE: 160
acacggcagg gucagggurc                                          20

<210> SEQ ID NO 161
<211> LENGTH: 20
<212> TYPE: RNA
<213> ORGANISM: Artificial Sequence
<220> FEATURE:
<223> OTHER INFORMATION: TRAC sg13

<400> SEQUENCE: 161
agcugguaca cggcagggurc                                         20

<210> SEQ ID NO 162
<211> LENGTH: 20
<212> TYPE: RNA
<213> ORGANISM: Artificial Sequence
<220> FEATURE:
<223> OTHER INFORMATION: TRAC sg14

<400> SEQUENCE: 162
gagaaucaaa aucggugaau                                              20

<210> SEQ ID NO 163
<211> LENGTH: 20
<212> TYPE: RNA
<213> ORGANISM: Artificial Sequence
<220> FEATURE:
<223> OTHER INFORMATION: TRAC sg15

<400> SEQUENCE: 163
gacaccuucu uccccagccc                                              20

<210> SEQ ID NO 164
<211> LENGTH: 20
<212> TYPE: RNA
<213> ORGANISM: Artificial Sequence
<220> FEATURE:
<223> OTHER INFORMATION: TRAC sg16

<400> SEQUENCE: 164
ucucucagcu gguacacggc                                              20

<210> SEQ ID NO 165
<211> LENGTH: 20
<212> TYPE: RNA
<213> ORGANISM: Artificial Sequence
<220> FEATURE:
<223> OTHER INFORMATION: TRAC sg17

<400> SEQUENCE: 165
gcugguacac ggcaggguca                                              20

<210> SEQ ID NO 166
<211> LENGTH: 20
<212> TYPE: RNA
<213> ORGANISM: Artificial Sequence
<220> FEATURE:
<223> OTHER INFORMATION: TRAC sg18

<400> SEQUENCE: 166
aaagucagau uuguugcucc                                              20

<210> SEQ ID NO 167
<211> LENGTH: 20
<212> TYPE: RNA
<213> ORGANISM: Artificial Sequence
<220> FEATURE:
<223> OTHER INFORMATION: TRAC sg19

<400> SEQUENCE: 167
cuggggaaga aggugucuuc                                              20

<210> SEQ ID NO 168
<211> LENGTH: 20
<212> TYPE: RNA
<213> ORGANISM: Artificial Sequence
<220> FEATURE:
<223> OTHER INFORMATION: TRAC sg20

<400> SEQUENCE: 168
uggauuuaga gucucucagc                                              20

<210> SEQ ID NO 169
<211> LENGTH: 20
<212> TYPE: RNA
<213> ORGANISM: Artificial Sequence
<220> FEATURE:
<223> OTHER INFORMATION: TRAC sg21

<400> SEQUENCE: 169
agagcaacag ugcuguggcc                                           20

<210> SEQ ID NO 170
<211> LENGTH: 20
<212> TYPE: RNA
<213> ORGANISM: Artificial Sequence
<220> FEATURE:
<223> OTHER INFORMATION: TRAC sg22

<400> SEQUENCE: 170
cuucaagagc aacagugcug                                           20

<210> SEQ ID NO 171
<211> LENGTH: 20
<212> TYPE: RNA
<213> ORGANISM: Artificial Sequence
<220> FEATURE:
<223> OTHER INFORMATION: TRAC sg23

<400> SEQUENCE: 171
auuuguuuga gaaucaaaau                                           20

<210> SEQ ID NO 172
<211> LENGTH: 20
<212> TYPE: RNA
<213> ORGANISM: Artificial Sequence
<220> FEATURE:
<223> OTHER INFORMATION: HLA-A02 sg10

<400> SEQUENCE: 172
cccucguccu gcuacucucg                                           20

<210> SEQ ID NO 173
<211> LENGTH: 20
<212> TYPE: RNA
<213> ORGANISM: Artificial Sequence
<220> FEATURE:
<223> OTHER INFORMATION: HLA-A02 sg2

<400> SEQUENCE: 173
cguacuggug guacccgcgg                                           20

<210> SEQ ID NO 174
<211> LENGTH: 20
<212> TYPE: RNA
<213> ORGANISM: Artificial Sequence
<220> FEATURE:
<223> OTHER INFORMATION: HLA-A02 sg5

<400> SEQUENCE: 174
cugaccauga agccacccug                                           20

<210> SEQ ID NO 175
<211> LENGTH: 20
<212> TYPE: RNA
<213> ORGANISM: Artificial Sequence
<220> FEATURE:
<223> OTHER INFORMATION: HLA-A02 sg14

<400> SEQUENCE: 175
agacucaccg aguggaccug                                           20

```
<210> SEQ ID NO 176
<211> LENGTH: 20
<212> TYPE: RNA
<213> ORGANISM: Artificial Sequence
<220> FEATURE:
<223> OTHER INFORMATION: HLA-A02 sg21

<400> SEQUENCE: 176
ggacccuccu gcucuaucca                                               20

<210> SEQ ID NO 177
<211> LENGTH: 20
<212> TYPE: RNA
<213> ORGANISM: Artificial Sequence
<220> FEATURE:
<223> OTHER INFORMATION: HLA-A02 sg23

<400> SEQUENCE: 177
gauguaaucc uugccgucgu                                               20

<210> SEQ ID NO 178
<211> LENGTH: 20
<212> TYPE: RNA
<213> ORGANISM: Artificial Sequence
<220> FEATURE:
<223> OTHER INFORMATION: HLA-A02 sg26

<400> SEQUENCE: 178
ccugcgcucu uggaccgcgg                                               20

<210> SEQ ID NO 179
<211> LENGTH: 20
<212> TYPE: RNA
<213> ORGANISM: Artificial Sequence
<220> FEATURE:
<223> OTHER INFORMATION: HLA-A02 sg29

<400> SEQUENCE: 179
ccucguccug cuacucucgg                                               20

<210> SEQ ID NO 180
<211> LENGTH: 20
<212> TYPE: RNA
<213> ORGANISM: Artificial Sequence
<220> FEATURE:
<223> OTHER INFORMATION: HLA-A02 sg30

<400> SEQUENCE: 180
aacccucguc cugcuacucu                                               20

<210> SEQ ID NO 181
<211> LENGTH: 20
<212> TYPE: RNA
<213> ORGANISM: Artificial Sequence
<220> FEATURE:
<223> OTHER INFORMATION: HLA-A02 sg31

<400> SEQUENCE: 181
gaggguucgg ggcgccauga                                               20

<210> SEQ ID NO 182
<211> LENGTH: 20
<212> TYPE: RNA
<213> ORGANISM: Artificial Sequence
<220> FEATURE:
<223> OTHER INFORMATION: HLA-A02 sg32
```

```
<400> SEQUENCE: 182
ccugcuacuc ucgggggcuc                                              20

<210> SEQ ID NO 183
<211> LENGTH: 20
<212> TYPE: RNA
<213> ORGANISM: Artificial Sequence
<220> FEATURE:
<223> OTHER INFORMATION: HLA-A02 sg33

<400> SEQUENCE: 183
cugguuguag uagccgcgca                                              20

<210> SEQ ID NO 184
<211> LENGTH: 20
<212> TYPE: RNA
<213> ORGANISM: Artificial Sequence
<220> FEATURE:
<223> OTHER INFORMATION: HLA-A02 sg34

<400> SEQUENCE: 184
uagcccacug cgaugaagcg                                              20

<210> SEQ ID NO 185
<211> LENGTH: 20
<212> TYPE: RNA
<213> ORGANISM: Artificial Sequence
<220> FEATURE:
<223> OTHER INFORMATION: HLA-A02 sg35

<400> SEQUENCE: 185
guggaccugg ggacccugcg                                              20

<210> SEQ ID NO 186
<211> LENGTH: 20
<212> TYPE: RNA
<213> ORGANISM: Artificial Sequence
<220> FEATURE:
<223> OTHER INFORMATION: HLA-A02 sg36

<400> SEQUENCE: 186
uggacgacac gcaguucgug                                              20

<210> SEQ ID NO 187
<211> LENGTH: 20
<212> TYPE: RNA
<213> ORGANISM: Artificial Sequence
<220> FEATURE:
<223> OTHER INFORMATION: HLA-A02 sg37

<400> SEQUENCE: 187
acagacucac cgaguggacc                                              20

<210> SEQ ID NO 188
<211> LENGTH: 20
<212> TYPE: RNA
<213> ORGANISM: Artificial Sequence
<220> FEATURE:
<223> OTHER INFORMATION: HLA-A02 sg38

<400> SEQUENCE: 188
gcaggagggu ccggaguauu                                              20

<210> SEQ ID NO 189
```

```
<211> LENGTH: 20
<212> TYPE: RNA
<213> ORGANISM: Artificial Sequence
<220> FEATURE:
<223> OTHER INFORMATION: HLA-A02 sg39

<400> SEQUENCE: 189
aguauuggga cggggagaca                                                    20

<210> SEQ ID NO 190
<211> LENGTH: 20
<212> TYPE: RNA
<213> ORGANISM: Artificial Sequence
<220> FEATURE:
<223> OTHER INFORMATION: HLA-A02 sg40

<400> SEQUENCE: 190
cucagaccac caagcacaag                                                    20

<210> SEQ ID NO 191
<211> LENGTH: 20
<212> TYPE: RNA
<213> ORGANISM: Artificial Sequence
<220> FEATURE:
<223> OTHER INFORMATION: HLA-A02 sg41

<400> SEQUENCE: 191
ccgccgcggu ccaagagcgc                                                    20

<210> SEQ ID NO 192
<211> LENGTH: 20
<212> TYPE: RNA
<213> ORGANISM: Artificial Sequence
<220> FEATURE:
<223> OTHER INFORMATION: HLA-A02 sg42

<400> SEQUENCE: 192
cucuuggacc gcggcggaca                                                    20

<210> SEQ ID NO 193
<211> LENGTH: 20
<212> TYPE: RNA
<213> ORGANISM: Artificial Sequence
<220> FEATURE:
<223> OTHER INFORMATION: HLA-A02 sg43

<400> SEQUENCE: 193
ggauuacauc gcccugaaag                                                    20

<210> SEQ ID NO 194
<211> LENGTH: 20
<212> TYPE: RNA
<213> ORGANISM: Artificial Sequence
<220> FEATURE:
<223> OTHER INFORMATION: HLA-A11 sg8-3

<400> SEQUENCE: 194
cccccgagag uagcaggagg                                                    20

<210> SEQ ID NO 195
<211> LENGTH: 20
<212> TYPE: RNA
<213> ORGANISM: Artificial Sequence
<220> FEATURE:
<223> OTHER INFORMATION: HLA-A11 sg9-3

<400> SEQUENCE: 195
```
aguagcagga ggaggguucg                                               20

<210> SEQ ID NO 196
<211> LENGTH: 20
<212> TYPE: RNA
<213> ORGANISM: Artificial Sequence
<220> FEATURE:
<223> OTHER INFORMATION: HLA-A11 sg10-3

<400> SEQUENCE: 196
cccuccuccu gcuacucucg                                               20

<210> SEQ ID NO 197
<211> LENGTH: 20
<212> TYPE: RNA
<213> ORGANISM: Artificial Sequence
<220> FEATURE:
<223> OTHER INFORMATION: HLA-A11 sg11-3

<400> SEQUENCE: 197
ccccgagagu agcaggagga                                               20

<210> SEQ ID NO 198
<211> LENGTH: 20
<212> TYPE: RNA
<213> ORGANISM: Artificial Sequence
<220> FEATURE:
<223> OTHER INFORMATION: HLA-A11 sg14-3

<400> SEQUENCE: 198
agacugaccg aguggaccug                                               20

<210> SEQ ID NO 199
<211> LENGTH: 20
<212> TYPE: RNA
<213> ORGANISM: Artificial Sequence
<220> FEATURE:
<223> OTHER INFORMATION: HLA-A11 sg16-3

<400> SEQUENCE: 199
ggggccggag uauugggacc                                               20

<210> SEQ ID NO 200
<211> LENGTH: 20
<212> TYPE: RNA
<213> ORGANISM: Artificial Sequence
<220> FEATURE:
<223> OTHER INFORMATION: HLA-A11 sg20-3

<400> SEQUENCE: 200
ccacucgguc agucugugac                                               20

<210> SEQ ID NO 201
<211> LENGTH: 20
<212> TYPE: RNA
<213> ORGANISM: Artificial Sequence
<220> FEATURE:
<223> OTHER INFORMATION: HLA-A11 sg21-3

<400> SEQUENCE: 201
uggauagagc aggaggggcc                                               20

<210> SEQ ID NO 202
<211> LENGTH: 20
<212> TYPE: RNA

```
<213> ORGANISM: Artificial Sequence
<220> FEATURE:
<223> OTHER INFORMATION: HLA-A11 sg28-3

<400> SEQUENCE: 202
ugccgucgua ggcguccugc                                                  20

<210> SEQ ID NO 203
<211> LENGTH: 20
<212> TYPE: RNA
<213> ORGANISM: Artificial Sequence
<220> FEATURE:
<223> OTHER INFORMATION: HLA-A11 Rsg2

<400> SEQUENCE: 203
cguccugccg guacccgcgg                                                  20

<210> SEQ ID NO 204
<211> LENGTH: 20
<212> TYPE: RNA
<213> ORGANISM: Artificial Sequence
<220> FEATURE:
<223> OTHER INFORMATION: HLA-A11 sg21

<400> SEQUENCE: 204
ggccccuccu gcucuaucca                                                  20

<210> SEQ ID NO 205
<211> LENGTH: 20
<212> TYPE: RNA
<213> ORGANISM: Artificial Sequence
<220> FEATURE:
<223> OTHER INFORMATION: HLA-A24 sg12-2

<400> SEQUENCE: 205
ccuggcccug acccagaccu                                                  20

<210> SEQ ID NO 206
<211> LENGTH: 20
<212> TYPE: RNA
<213> ORGANISM: Artificial Sequence
<220> FEATURE:
<223> OTHER INFORMATION: HLA-A24 sg13-2

<400> SEQUENCE: 206
cccuggcccu gacccagacc                                                  20

<210> SEQ ID NO 207
<211> LENGTH: 20
<212> TYPE: RNA
<213> ORGANISM: Artificial Sequence
<220> FEATURE:
<223> OTHER INFORMATION: HLA-A24 sg14-2

<400> SEQUENCE: 207
agacugaccg agagaaccug                                                  20

<210> SEQ ID NO 208
<211> LENGTH: 20
<212> TYPE: RNA
<213> ORGANISM: Artificial Sequence
<220> FEATURE:
<223> OTHER INFORMATION: HLA-A24 sg16-2

<400> SEQUENCE: 208
ggggccggag uauugggacg                                                  20
```

<210> SEQ ID NO 209
<211> LENGTH: 20
<212> TYPE: RNA
<213> ORGANISM: Artificial Sequence
<220> FEATURE:
<223> OTHER INFORMATION: HLA-A24 sg20-2

<400> SEQUENCE: 209
ucucucgguc agucugugag                                               20

<210> SEQ ID NO 210
<211> LENGTH: 20
<212> TYPE: RNA
<213> ORGANISM: Artificial Sequence
<220> FEATURE:
<223> OTHER INFORMATION: HLA-A24 sg21-2

<400> SEQUENCE: 210
ggccccuccu gcucuaucca                                               20

<210> SEQ ID NO 211
<211> LENGTH: 20
<212> TYPE: RNA
<213> ORGANISM: Artificial Sequence
<220> FEATURE:
<223> OTHER INFORMATION: HLA-A24 sg22-2

<400> SEQUENCE: 211
aggcguacug gugguacccg                                               20

<210> SEQ ID NO 212
<211> LENGTH: 20
<212> TYPE: RNA
<213> ORGANISM: Artificial Sequence
<220> FEATURE:
<223> OTHER INFORMATION: HLA-A24 sg25-2

<400> SEQUENCE: 212
cugagccgcc auguccgccg                                               20

<210> SEQ ID NO 213
<211> LENGTH: 21
<212> TYPE: RNA
<213> ORGANISM: Artificial Sequence
<220> FEATURE:
<223> OTHER INFORMATION: HLA-A-homo-551

<400> SEQUENCE: 213
gcggagcagu ugagagccua c                                             21

<210> SEQ ID NO 214
<211> LENGTH: 21
<212> TYPE: RNA
<213> ORGANISM: Artificial Sequence
<220> FEATURE:
<223> OTHER INFORMATION: HLA-A-homo-NEG

<400> SEQUENCE: 214
gcucagauca ccaagcgcaa g                                             21

<210> SEQ ID NO 215
<211> LENGTH: 21
<212> TYPE: RNA
<213> ORGANISM: Artificial Sequence
<220> FEATURE:

<223> OTHER INFORMATION: TRAC-homo-375

<400> SEQUENCE: 215
gaaaguggcc ggguuuaauc u                                              21

<210> SEQ ID NO 216
<211> LENGTH: 21
<212> TYPE: RNA
<213> ORGANISM: Artificial Sequence
<220> FEATURE:
<223> OTHER INFORMATION: TRAC-homo-NEG

<400> SEQUENCE: 216
gaaacagaua cgaaccuaaa c                                              21

<210> SEQ ID NO 217
<211> LENGTH: 33
<212> TYPE: DNA
<213> ORGANISM: Artificial Sequence
<220> FEATURE:
<223> OTHER INFORMATION: fig. 13 line 1

<400> SEQUENCE: 217
atccagaacc ctgaccctgc cgtgtaacca gct                                 33

<210> SEQ ID NO 218
<211> LENGTH: 32
<212> TYPE: DNA
<213> ORGANISM: Artificial Sequence
<220> FEATURE:
<223> OTHER INFORMATION: fig. 13 line 2

<400> SEQUENCE: 218
atccagaacc ctgaccctgc cgtgtaccag ct                                  32

<210> SEQ ID NO 219
<211> LENGTH: 51
<212> TYPE: DNA
<213> ORGANISM: Artificial Sequence
<220> FEATURE:
<223> OTHER INFORMATION: fig. 14 line 1 and line 3

<400> SEQUENCE: 219
ccagaacccT gaccctgccg tgtaccagct gagagactct aaatccagtg a              51

<210> SEQ ID NO 220
<211> LENGTH: 51
<212> TYPE: DNA
<213> ORGANISM: Artificial Sequence
<220> FEATURE:
<223> OTHER INFORMATION: fig. 14 line 2

<400> SEQUENCE: 220
ggtcttggga ctgggacggc acatggtcga ctctctgaga tttaggtcac t              51

<210> SEQ ID NO 221
<211> LENGTH: 52
<212> TYPE: DNA
<213> ORGANISM: Artificial Sequence
<220> FEATURE:
<223> OTHER INFORMATION: fig. 14 line 4

<400> SEQUENCE: 221
ccagaacccT gaccctgccg tctaaccagc tgagagactc taaatccagt ga             52

-continued

```
<210> SEQ ID NO 222
<211> LENGTH: 52
<212> TYPE: DNA
<213> ORGANISM: Artificial Sequence
<220> FEATURE:
<223> OTHER INFORMATION: fig. 14 line 5

<400> SEQUENCE: 222
ccagaaccct gaccctgccg tgtaaccagc tgagagactc taaatccagt ga        52

<210> SEQ ID NO 223
<211> LENGTH: 45
<212> TYPE: DNA
<213> ORGANISM: Artificial Sequence
<220> FEATURE:
<223> OTHER INFORMATION: fig. 14 line 6

<400> SEQUENCE: 223
ccagaaccct gaccctggcc agctgagaga ctctaaatcc agtga                45

<210> SEQ ID NO 224
<211> LENGTH: 46
<212> TYPE: DNA
<213> ORGANISM: Artificial Sequence
<220> FEATURE:
<223> OTHER INFORMATION: fig. 14 line 8

<400> SEQUENCE: 224
ccagaaccct gaccctgccg tgtcactctc tgacagagtc taattc               46

<210> SEQ ID NO 225
<211> LENGTH: 49
<212> TYPE: DNA
<213> ORGANISM: Artificial Sequence
<220> FEATURE:
<223> OTHER INFORMATION: fig. 14 line 10

<400> SEQUENCE: 225
ccagaaccct gaccctgccg tgtcagctga gagactctaa atccagtga             49

<210> SEQ ID NO 226
<211> LENGTH: 48
<212> TYPE: DNA
<213> ORGANISM: Artificial Sequence
<220> FEATURE:
<223> OTHER INFORMATION: fig. 14 line 12

<400> SEQUENCE: 226
ccagaaccct gaccctgccg tgtagctgag agactctaaa tccagtga              48

<210> SEQ ID NO 227
<211> LENGTH: 34
<212> TYPE: DNA
<213> ORGANISM: Artificial Sequence
<220> FEATURE:
<223> OTHER INFORMATION: fig. 14 line 14

<400> SEQUENCE: 227
ccagaaccct gaccctgccg tgtaaatcca gtga                             34

<210> SEQ ID NO 228
<211> LENGTH: 44
<212> TYPE: DNA
<213> ORGANISM: Artificial Sequence
<220> FEATURE:
<223> OTHER INFORMATION: fig. 14 line 15
```

```
<400> SEQUENCE: 228
ccagaaccct gaccctgcca gctgagagac tctaaatcca gtga                    44

<210> SEQ ID NO 229
<211> LENGTH: 62
<212> TYPE: DNA
<213> ORGANISM: Artificial Sequence
<220> FEATURE:
<223> OTHER INFORMATION: fig. 16 line 1

<400> SEQUENCE: 229
gggtcggact ggcgcttcct ccgcgggtac caccagtacg cctacgacgg caaggattac   60
at                                                                  62

<210> SEQ ID NO 230
<211> LENGTH: 59
<212> TYPE: DNA
<213> ORGANISM: Artificial Sequence
<220> FEATURE:
<223> OTHER INFORMATION: fig. 16 line 2
<220> FEATURE:
<221> NAME/KEY: misc_feature
<222> LOCATION: (3)..(3)
<223> OTHER INFORMATION: n = a or g or c or t
<220> FEATURE:
<221> NAME/KEY: misc_feature
<222> LOCATION: (8)..(9)
<223> OTHER INFORMATION: n = a or g or c or t
<220> FEATURE:
<221> NAME/KEY: misc_feature
<222> LOCATION: (31)..(31)
<223> OTHER INFORMATION: n = a or g or c or t
<220> FEATURE:
<221> NAME/KEY: misc_feature
<222> LOCATION: (33)..(34)
<223> OTHER INFORMATION: n = a or g or c or t

<400> SEQUENCE: 230
gtntgggnng ggcttttttct ccgggtacca ncnntacgcc tacgacggca aggattaca   59

<210> SEQ ID NO 231
<211> LENGTH: 55
<212> TYPE: DNA
<213> ORGANISM: Artificial Sequence
<220> FEATURE:
<223> OTHER INFORMATION: fig. 17 line 1

<400> SEQUENCE: 231
tatgactcac cacgctgtct ctgaccatga agccaccctg aggtgctggg ccctg        55

<210> SEQ ID NO 232
<211> LENGTH: 54
<212> TYPE: DNA
<213> ORGANISM: Artificial Sequence
<220> FEATURE:
<223> OTHER INFORMATION: fig. 17 line 2

<400> SEQUENCE: 232
tatgactcac cacgctgtct ctgaccatga agccacctga ggtgctgggc cctg         54

<210> SEQ ID NO 233
<211> LENGTH: 55
<212> TYPE: DNA
<213> ORGANISM: Artificial Sequence
<220> FEATURE:
<223> OTHER INFORMATION: fig. 18 line 1

<400> SEQUENCE: 233
```

```
acgccgcgag ccagaggatg gagccgcggg cgccgtggat agagcaggag gggcc        55
```

<210> SEQ ID NO 234
<211> LENGTH: 55
<212> TYPE: DNA
<213> ORGANISM: Artificial Sequence
<220> FEATURE:
<223> OTHER INFORMATION: fig. 18 line 2
<220> FEATURE:
<221> NAME/KEY: misc_feature
<222> LOCATION: (3)..(3)
<223> OTHER INFORMATION: n = a or g or c or t
<220> FEATURE:
<221> NAME/KEY: misc_feature
<222> LOCATION: (6)..(6)
<223> OTHER INFORMATION: n = a or g or c or t
<220> FEATURE:
<221> NAME/KEY: misc_feature
<222> LOCATION: (10)..(10)
<223> OTHER INFORMATION: n = a or g or c or t
<220> FEATURE:
<221> NAME/KEY: misc_feature
<222> LOCATION: (19)..(19)
<223> OTHER INFORMATION: n = a or g or c or t

<400> SEQUENCE: 234

```
acnccncgan ccagaggang gagccgcggg ccccgtggat agagcaggag gggcc        55
```

<210> SEQ ID NO 235
<211> LENGTH: 51
<212> TYPE: DNA
<213> ORGANISM: Artificial Sequence
<220> FEATURE:
<223> OTHER INFORMATION: fig. 19 line 1

<400> SEQUENCE: 235

```
gggccggacg ggcgcttcct ccgcgggtac cggcaggacg cctacgacgg c            51
```

<210> SEQ ID NO 236
<211> LENGTH: 51
<212> TYPE: DNA
<213> ORGANISM: Artificial Sequence
<220> FEATURE:
<223> OTHER INFORMATION: fig. 19 line 2

<400> SEQUENCE: 236

```
gggccggacg ggcgcttcct ccggggtac caccgggacc cttacaacgg c             51
```

<210> SEQ ID NO 237
<211> LENGTH: 35
<212> TYPE: DNA
<213> ORGANISM: Artificial Sequence
<220> FEATURE:
<223> OTHER INFORMATION: fig. 20A line1 and line2

<400> SEQUENCE: 237

```
tctgaccatg aagccaccct gaggtgctgg gccct                              35
```

<210> SEQ ID NO 238
<211> LENGTH: 19
<212> TYPE: DNA
<213> ORGANISM: Artificial Sequence
<220> FEATURE:
<223> OTHER INFORMATION: fig. 20A line 3

<400> SEQUENCE: 238

```
ccctgaggtg ctgggccct                                                19
```

```
<210> SEQ ID NO 239
<211> LENGTH: 40
<212> TYPE: DNA
<213> ORGANISM: Artificial Sequence
<220> FEATURE:
<223> OTHER INFORMATION: fig. 20B line1 and line2

<400> SEQUENCE: 239
accctgccgt gtaccagctg agagactcta aatccagtga                         40

<210> SEQ ID NO 240
<211> LENGTH: 41
<212> TYPE: DNA
<213> ORGANISM: Artificial Sequence
<220> FEATURE:
<223> OTHER INFORMATION: fig. 20B line3

<400> SEQUENCE: 240
accctgccgt gtaaccagct gagagactct aaatccagtg a                       41
```